US010626394B2

(12) United States Patent
Lu et al.

(10) Patent No.: US 10,626,394 B2
(45) Date of Patent: Apr. 21, 2020

(54) SYNTHETIC BACTERIOPHAGES AND BACTERIOPHAGE COMPOSITIONS

(71) Applicant: Massachusetts Institute of Technology, Cambridge, MA (US)

(72) Inventors: Timothy Kuan-Ta Lu, Cambridge, MA (US); Sebastien Lemire, Belmont, MA (US); Andrew C. Yang, Fullerton, CA (US); Kevin M. Yehl, Quincy, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 21 days.

(21) Appl. No.: 15/795,510

(22) Filed: Oct. 27, 2017

(65) Prior Publication Data

US 2018/0155721 A1 Jun. 7, 2018

Related U.S. Application Data

(60) Provisional application No. 62/414,558, filed on Oct. 28, 2016.

(51) Int. Cl.
| | | |
|---|---|---|
| *A61K 38/00* | (2006.01) |
| *C07K 14/00* | (2006.01) |
| *C12P 21/04* | (2006.01) |
| *C07H 21/04* | (2006.01) |
| *C07K 14/005* | (2006.01) |
| *C12N 15/113* | (2010.01) |
| *G01N 33/569* | (2006.01) |
| *A61P 31/04* | (2006.01) |

(52) U.S. Cl.
CPC ............ *C12N 15/113* (2013.01); *A61P 31/04* (2018.01); *C07K 14/005* (2013.01); *G01N 33/56916* (2013.01); *C12N 2320/32* (2013.01); *C12N 2330/30* (2013.01); *C12N 2795/00021* (2013.01); *C12N 2795/00032* (2013.01); *C12N 2795/14122* (2013.01); *C12N 2795/14132* (2013.01)

(58) Field of Classification Search
CPC .. C07K 14/005; C07K 14/21; C07K 2319/35; C07K 2319/74; C12N 7/00
See application file for complete search history.

(56) References Cited

U.S. PATENT DOCUMENTS 7,163,818 B2 * 1/2007 Merril ................ A61K 35/76
435/235.1
9,217,145 B2 * 12/2015 Sokoloff ............. C07K 14/005

FOREIGN PATENT DOCUMENTS

| WO | WO 2004/013307 A2 | 2/2004 |
| WO | WO 2013/045863 A1 | 4/2013 |
| WO | WO 2015/035168 A1 | 3/2015 |

OTHER PUBLICATIONS

Alexander, Why microbial predators and parasites do not eliminate their prey and hosts. Annu Rev. Microbiol. 1981;35:113-33. Doi: 10.1146/annurev.mi.35.100181.000553.
Ando et al., Engineering Modular Viral Scaffolds for Targeted Bacterial Population Editing. Cell Syst. Sep. 23, 2015;1(3):187-96. Author provided manuscript, Sep. 23, 2016. 22 pages.
Bikard et al., Exploiting CRISPR-Cas nucleases to produce sequence-specific antimicrobials. Nat Biotechnol. Nov. 2014;32(11):1146-50. doi: 10.1038/nbt.3043. Epub Oct. 5, 2014. Author provided manuscript, May 1, 2015. 16 pages.
Bull et al., Phenotypic Resistance and the Dynamics of Bacterial Escape from Phage Control. PLoS Cell. Apr. 17, 2014;9(4):e94690, 10 pages.
Chan et al., Phage cocktails and the future of phage therapy. Future Microbiol. Jun. 2013;8(6):769-83. doi: 10.2217/fmb.13.47.
Chen et al., Inducible Prophage Mutant of *Escherichia coli* Can Lyse New Host and the Key Sites of Receptor Recognition Identification. Front Microbiol. 2017;8:147, 13 pages. Doi: 10.3389/fmicb.2017.00147. Epub Feb. 1, 2017.
Chen et al., Incorporation of therapeutically modified bacteria into gut microbiota inhibits obesity. J Clin Invest. Aug. 2014;124(8):3391-406. doi: 10.1172/JCI72517. Epub Jun. 24, 2014.
Citorik et al., Sequence-specific antimicrobials using efficiently delivered RNA-guided nucleases. Nat Biotechnol. Nov. 2014;32(11):1141-5. doi: 10.1038/nbt.3011. Epub Sep. 21, 2014. Author provided manuscript, May 1, 2015. 18 pages.
Cooper et al., Adapting Drug Approval Pathways for Bacteriophage-Based Therapeutics. Front Microbiol. Aug. 3, 2016;7:1209, 15 pages. doi: 10.3389/fmicb.2016.01209. eCollection 2016.
Devlin et al., Modulation of a Circulating Uremic Solute via Rational Genetic Manipulation of the Gut Microbiota. Cell Host Microbe. Dec. 14, 2016;20(6):709-715. doi: 10.1016/j.chom.2016.10.021. Epub Dec. 1, 2016. Author provided manuscript, Dec. 14, 2017. 13 pages.
Galtier et al., Bacteriophages to reduce gut carriage of antibiotic resistant uropathogens with low impact on microbiota composition. Environ Microbiol. Jul. 2016;18(7):2237-45. doi: 10.1111/1462-2920.13284. Epub Apr. 28, 2016.
Garcia-Doval et al., Structure of the receptor-binding carboxy-terminal domain of bacteriophage T7 tail fibers. PNAS. Jun. 12, 2012;109(24):9390-5. Doi: 10.1073/pnas.1119719109.
Gebhart et al., Bacteriophage SP6 encodes a second tailspike protein that recognizes *Salmonella enterica* serogroups C2 and C3. Virology. Jul. 2017;507:263-266. doi: 10.1016/j.virol.2017.02.025. Epub Mar. 10, 2017. Author manuscript provided, Jul. 1, 2018. 12 pages.
Guo et al., Diversity-Generating Retroelements in Phage and Bacterial Genomes. Microbiol Spectr. Dec. 2014;2(6):22 pages. Doi: 10.1128/microbiolspec.MDNA3-0029-2014. Author provided manuscript, Jun. 10, 2015.
Hawkins et al., Genome sequence of the Bacteroides fragilis phage ATCC 51477-B1. Virol J. 2008;5:97, 5 pages. Doi: 10.1186/1743-422X-5-97. Epub Aug. 18, 2008.
Heilpern e t al., pIIICTX, a Predicted CTXφ Minor Coat Protein, Can Expand the Host Range of Coliphage fd To Include Vibrio cholera. J Bacteriol. Feb. 2003;185(3):1037-44.

(Continued)

*Primary Examiner* — Barry A Chestnut
(74) *Attorney, Agent, or Firm* — Wolf, Greenfield & Sacks, P.C.

(57) ABSTRACT

Disclosed herein are novel synthetic bacteriophages and bacteriophage compositions, methods of production thereof, and therapeutic uses thereof.

18 Claims, 32 Drawing Sheets

Specification includes a Sequence Listing.

(56) References Cited

OTHER PUBLICATIONS

Klein et al., *Escherichia coli* K-12 Suppressor-free Mutants Lacking Early Glycosyltransferases and Late Acyltransferases: minimal lipopolysaccharide structure and induction of envelope stress response. J Biol Chem. Jun. 5, 2009;284(23):15369-89. doi: 10.1074/jbc.M900490200. Epub Apr. 3, 2009.
Kutateladze et al., Bacteriophages as potential new therapeutics to replace or supplement antibiotics. Trends Biotechnol. Dec. 2010;28(12):591-5. doi: 10.1016/j.tibtech.2010.08.001. Epub Aug. 31, 2010.
Kutter et al., Phage therapy in clinical practice: treatment of human infections. Curr Pharm Biotechnol. Jan. 2010;11(1):69-86.
Kutter et al., Re-establishing a place for phage therapy in western medicine. Future Microbiol. 2015;10(5):685-8. doi: 10.2217/fmb.15.28.
Labrie et al., Bacteriophage resistance mechanisms. Nat Rev Microbiol. May 2010;8(5):317-27. doi: 10.1038/nrmicro2315. Epub Mar. 29, 2010.
Levin et al., Population and evolutionary dynamics of phage therapy. Nat Rev Microbiol. Mar. 2004;2:166-73. Doi: 10.1038/nrmicro822.
Lin et al., A T3 and T7 Recombinant Phage Acquires Efficient Adsorption and a Broader Host Range. PLoS One. 2012;7(2):e30954, 10 pages.
Lu et al., Dispersing biofilms with engineered enzymatic bacteriophage. Proc Natl Acad Sci USA. Jul. 3, 2007;104(27):11197-202. Epub Jun. 25, 2007.
Lu et al., Engineered bacteriophage targeting gene networks as adjuvants for antibiotic therapy. Proc Natl Acad Sci USA.Mar. 24, 2009;106(12):4629-34.
Maynard et al., A Forward-Genetic Screen and Dynamic Analysis of Lambda Phage Host-Dependencies Reveals an Extensive Interaction Network and a New Anti-Viral Strategy. PLoS Genet. Jul. 8, 2010;6(7):e1001017, 15 pages.
McMahon et al., The C-type lectin fold as an evolutionary solution for massive sequence variation. Nat Struct Mol Biol. Oct. 2005;12(10):886-92. Epub Sep. 18, 2005.
Meyer et al., Repeatability and contingency in the evolution of a key innovation in phage lambda. Science. Jan. 27, 2012;335(6067):428-32. doi: 10.1126/science.1214449. Author provided manuscript, Mar. 18, 2012.
Miedzybrodski et al., Clinical aspects of phage therapy. Adv Virus Res. 2012;83:73-121. doi: 10.1016/B978-0-12-394438-2.00003-7.
Montag et al., Receptor-recognizing proteins of T-even type bacteriophages. Constant and hypervariable regions and an unusual case of evolution. J Mol Biol. Jul. 5, 1987;196(1):165-74.
Nguyen et al., Multiple genetic pathways to similar fitness limits during viral adaptation to a new host. Evolution. Feb. 2012;66(2):363-74. Doi: 10.1111/j.1558-5646.2011.01433.x. Epub Sep. 20, 2011. Author provided manuscript, Feb. 1, 2013. 21 pages.

Overstreet et al., Self-made phage libraries with heterologous inserts in the Mtd of Bordetella bronchiseptica. Protein Eng Des Sel. Apr. 2012;25(4):145-51. doi: 10.1093/protein/gzr068. Epub Jan. 27, 2012.
Perry et al., The Molecular and Genetic Basis of Repeatable Coevolution between *Escherichia coli* and Bacteriophage T3 in a Laboratory Microcosm. PLoS One. Jun. 26, 2015;10(6):e0130639, 12 pages. Doi: 10.1371/journal.pone.0130639.
Pouillot et al., Genetically Engineered Virulent Phage Banks in the Detection and Control of Emergent Pathogenic Bacteria. Biosecur Bioterror. Jun. 2010;8(2):155-69. Doi: 10.1089/bsp.2009.0057.
Qimron et al., Genomewide screens for *Escherichia coli* genes affecting growth of T7 bacteriophage. Proc Natl Acad Sci USA. Dec. 12, 2006;103(50):19039-44.
Ross et al., More Is Better: Selecting for Broad Host Range Bacteriophages. Front Microbiol. Sep. 8, 2016;7:1352, 6 pages. doi: 10.3389/fmicb.2016.01352. eCollection 2016.
Scholl et al., An engineered R-type pyocin is a highly specific and sensitive bactericidal agent for the food-borne pathogen *Escherichia coli* O157:H7. Antimicrob Agents Chemother. Jul. 2009;53(7):3074-80. Doi: 10.1128/aac.01660-08.
Shen et al., Engineering the gut microbiota to treat hyperammonemia. J Clin Invest. Jul. 1, 2015;125(7):2841-50. doi: 10.1172/JCI79214. Epub Jun. 22, 2015.
Silva et al., Host receptors for bacteriophage adsorption. FEMS Microbiol Lett. Feb. 2016;363(4):fnw002, 11 pages. doi: 10.1093/femsle/fnw002. Epub Jan. 10, 2016.
Springman et al., Evolution at a high imposed mutation rate: adaptation obscures the load in phage T7. Genetics. Jan. 2010;184:221-32. Doi: 10.1534/genetics.109.108803.
Studier et al., Understanding the differences between genome sequences of *Escherichia coli* B strains REL606 and BL21(DE3) and comparison of the *E. coli* B and K-12 genomes. J Mol Biol. Dec. 11, 2009;394(4):653-80. doi: 10.1016/j.jmb.2009.09.021. Epub Sep. 15, 2009.
Tetart et al., Bacteriophage T4 host range is expanded by duplications of a small domain of the tail fiber adhesin. J Mol Biol. May 24, 1996;258(5):726-31. doi: 10.1016/j.jbiotec.2004.08.00.
Trojet et al., The gp38 Adhesins of the T4 Superfamily: A Complex Modular Determinant of the Phage's Host Specificity. Genome Biol Evol. 2011;3:674-686. doi: 10.1093/gbe/evr059. Epub Jul. 11, 2011.
Yehl et al., Engineering Phage Host-Range and Suppressing Bacterial Resistance Through Phage Tail Fiber Mutagenesis. bioRxiv. Jul. 11, 2019:1-52. doi: http://dx.doi.org/10.1101/699090.
Yoichi et al., Alteration of tail fiber protein gp38 enables T2 phage to infect *Escherichia coli* O157:H7. J Biotechnol. Feb. 2005;115(1):101-7. doi: 10.1016/j.jbiotec.2004.08.003.
Yosef et al., Extending the Host Range of Bacteriophage Particles for DNA Transduction. Mol Cell. Jun. 1, 2017;66(5):721-728.e3. doi: 10.1016/j.molcel.2017.04.025. Epub May 25, 2017.
Yu et al., Isolation of Polyvalent Bacteriophages by Sequential Multiple-Host Approaches. Appl Environ Microbiol. Feb. 1, 2016;82(3):808-15. doi: 10.1128/AEM.02382-15. Epub Jan. 22, 2016.

\* cited by examiner

FIG. 2A

FIG. 5C
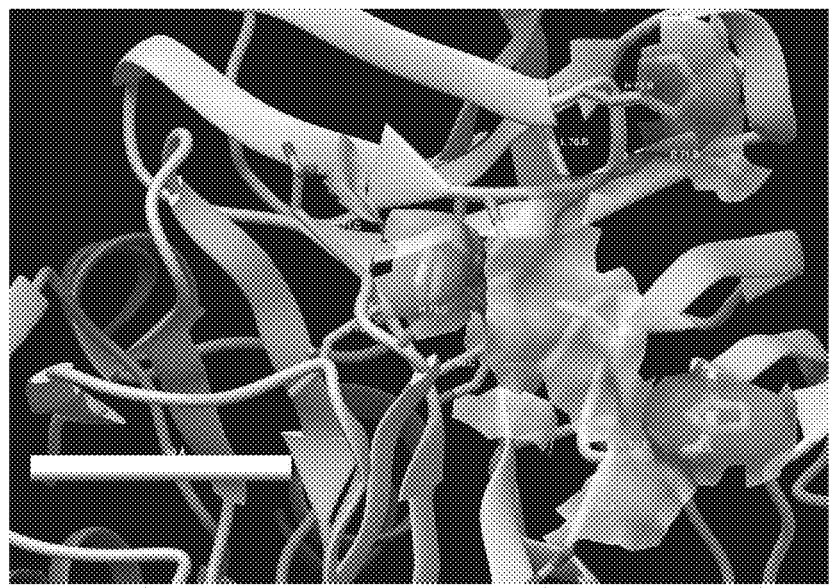
FIG. 6A
R546 DAPP T551
HGLSL
LGLAV
NCHV
HTGI
AYASP
KSGV
KAGI
HSVV
KAGP
HTHP
GARV
ASRV
RTFI
KLNI
RFVV
RDIRLSI
FIG. 6B
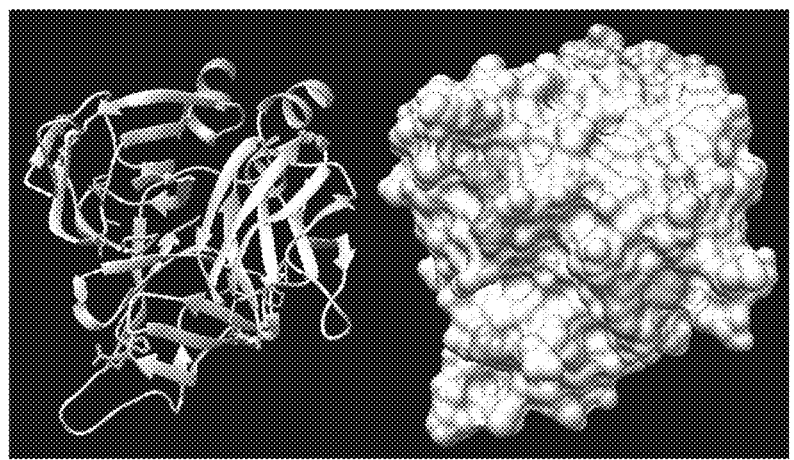

FIG. 13A
FIG. 13B
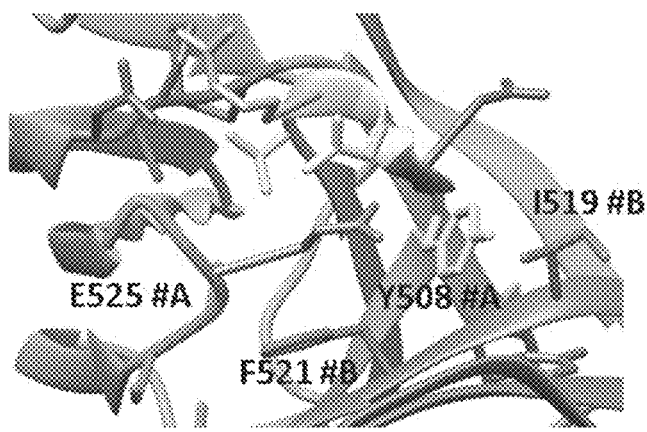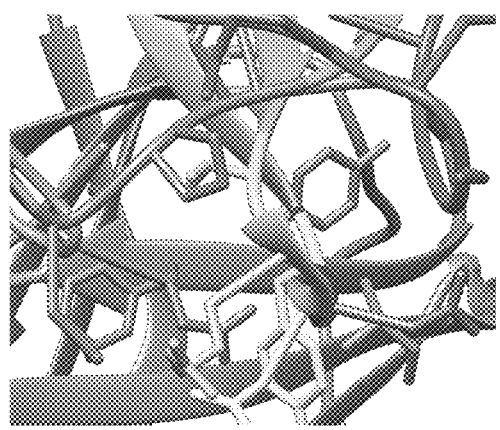
- Monomer A
- Monomer B
- Monomer C
- FG loop
- FG loop E525
- BC loop
- HI loop
- DE loop T504
- DE loop R505
- DE loop N506
- DE loop N507
- DE loop Y508

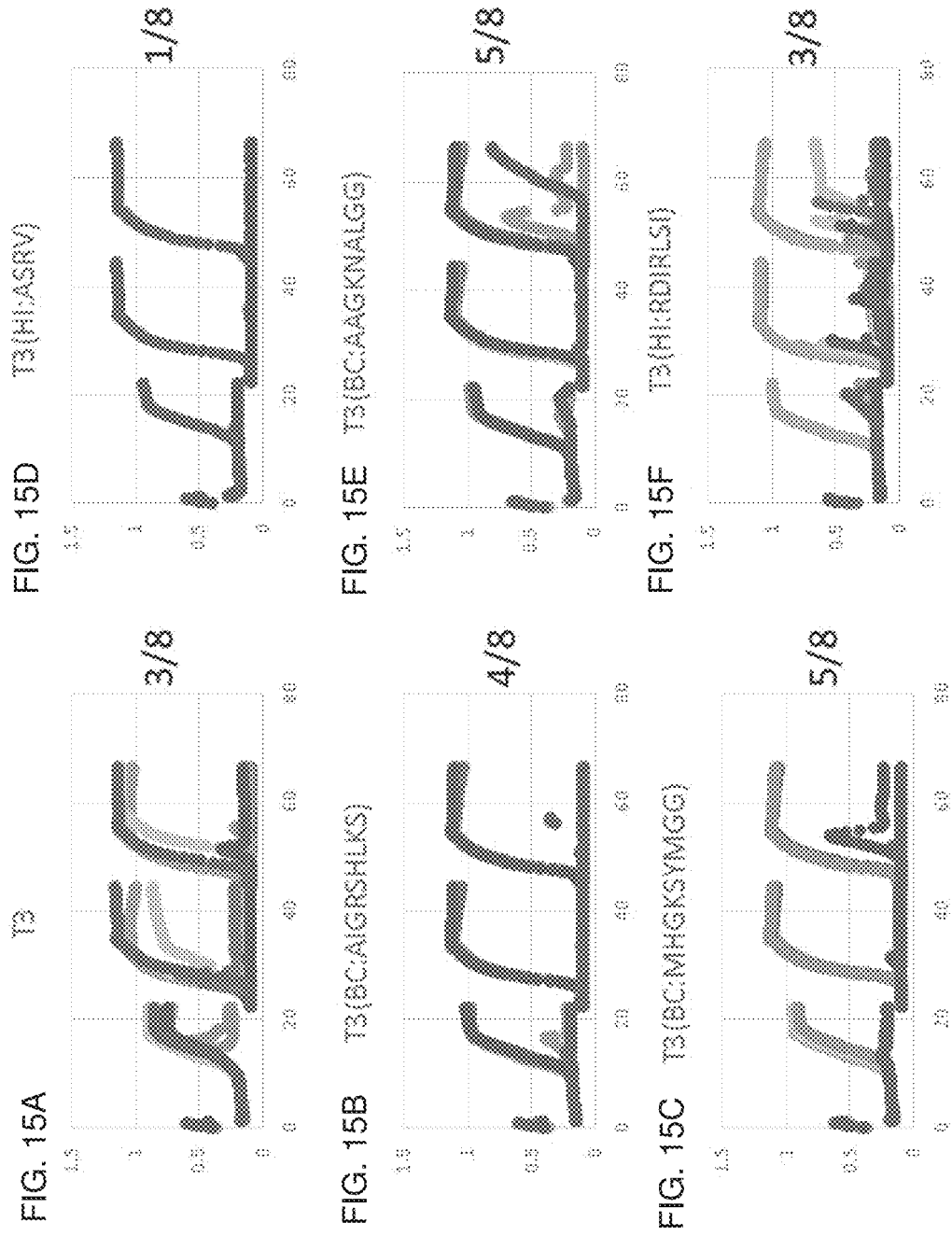

FIG. 22A
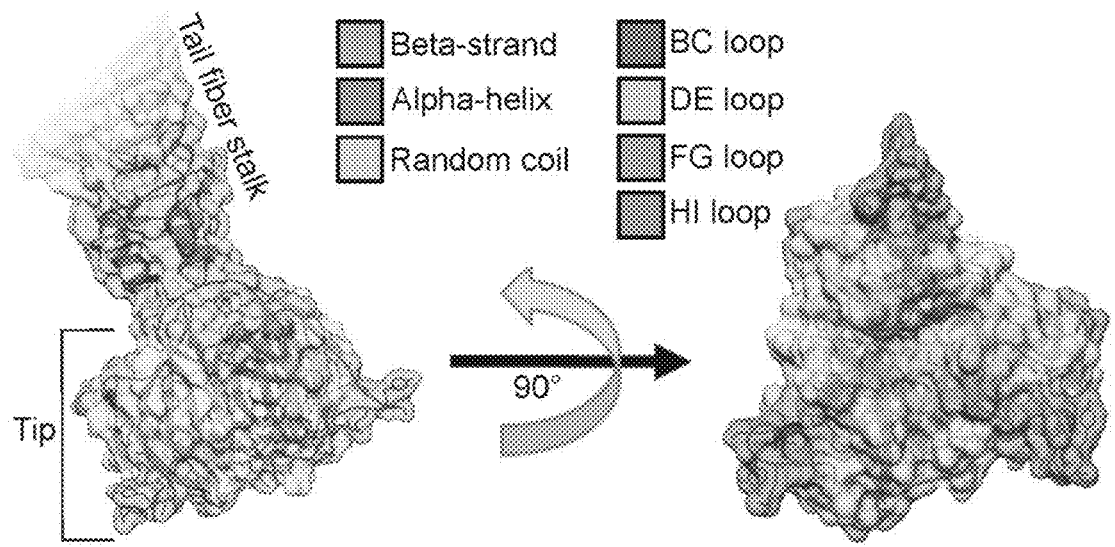
FIG. 22B
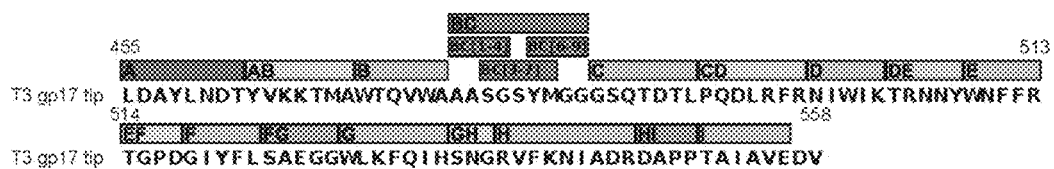
FIG. 23A
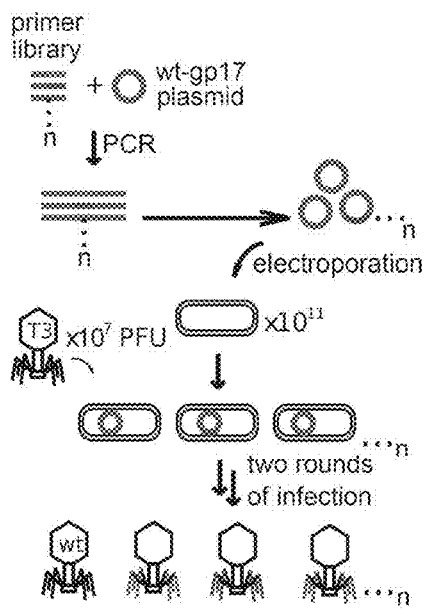
FIG. 23B
| Phage library | # of codons mutated | DNA sequence space | Protein sequence space |
|---|---|---|---|
| BC[1-4] | 4 | 1.0E+06 | 1.6E+05 |
| BC[3-7] | 5 | 3.4E+07 | 3.2E+06 |
| BC[6-9] | 4 | 1.0E+06 | 1.6E+05 |
| DE | 5 | 3.4E+07 | 3.2E+06 |
| FG | 5 | 3.4E+07 | 3.2E+06 |
| HI | 4 | 1.0E+06 | 1.6E+05 |
| HI[5] | 5 | 3.4E+07 | 3.2E+06 |
| gp17wt | 0 | 1 | 1 |

FIG. 23C
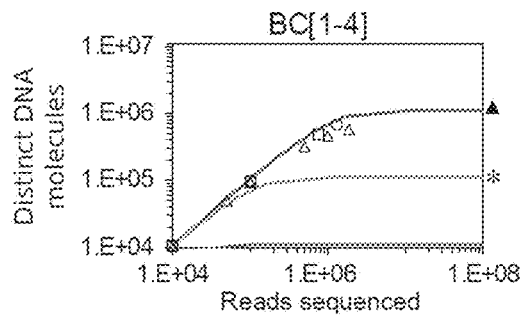
FIG. 23G
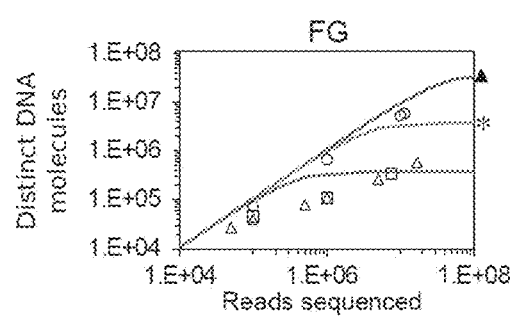
FIG. 23D
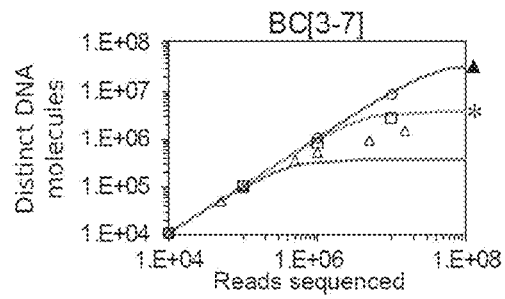
FIG. 23H
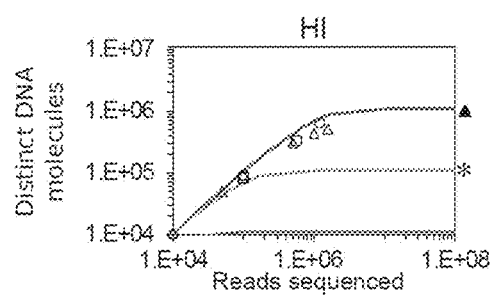
FIG. 23E
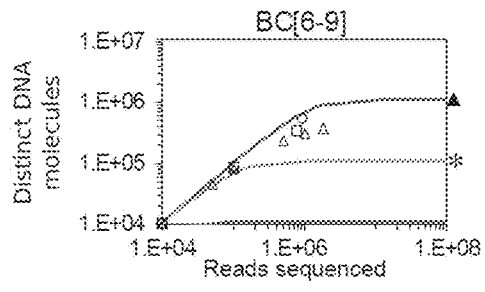
FIG. 23I
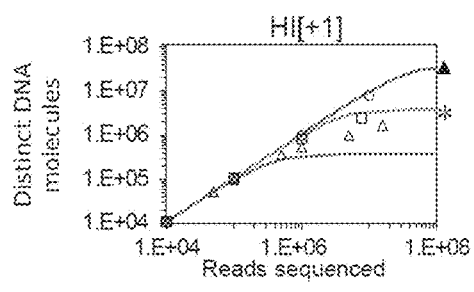
FIG. 23F
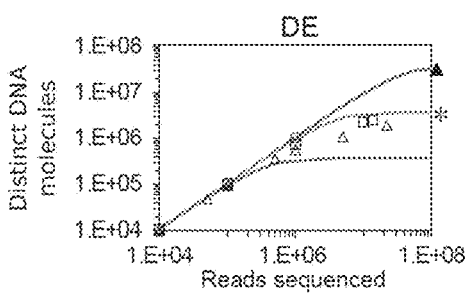
FIG. 23J

FIG. 24A  FIG. 24B  FIG. 24C
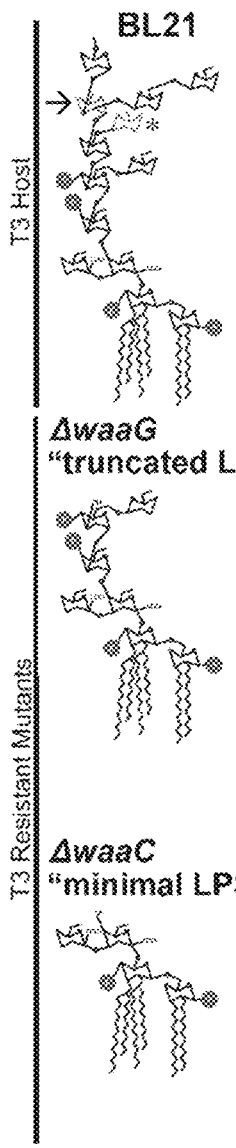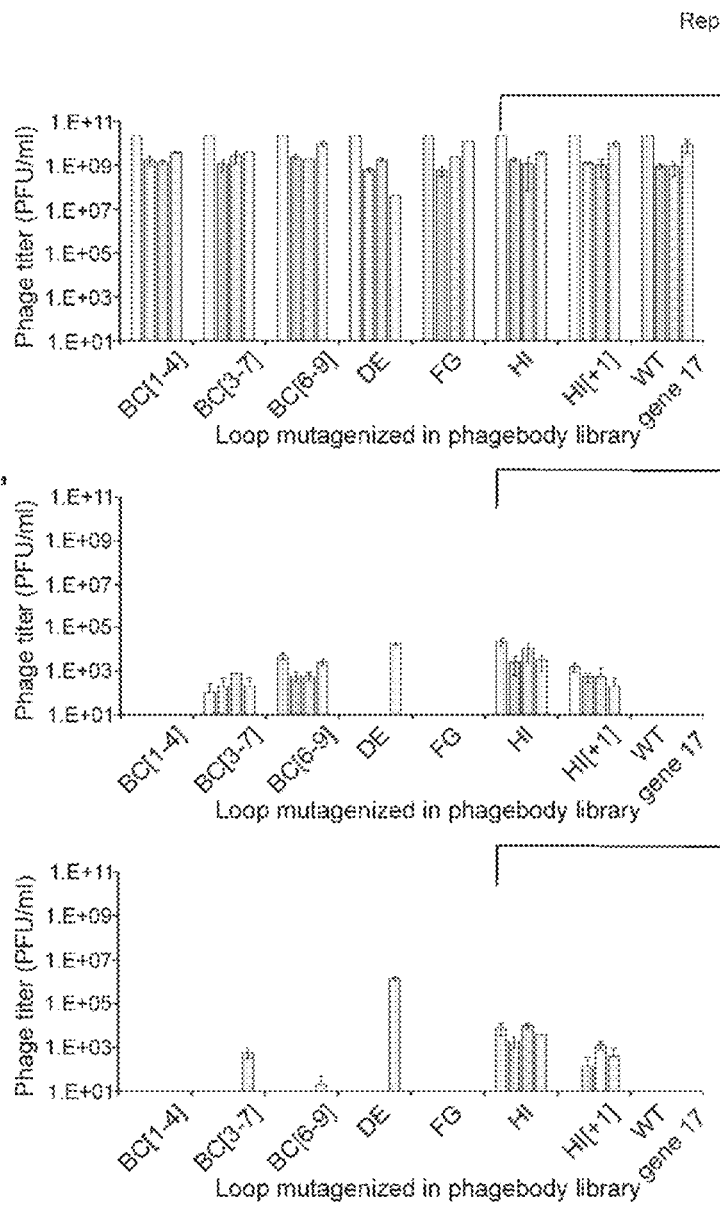

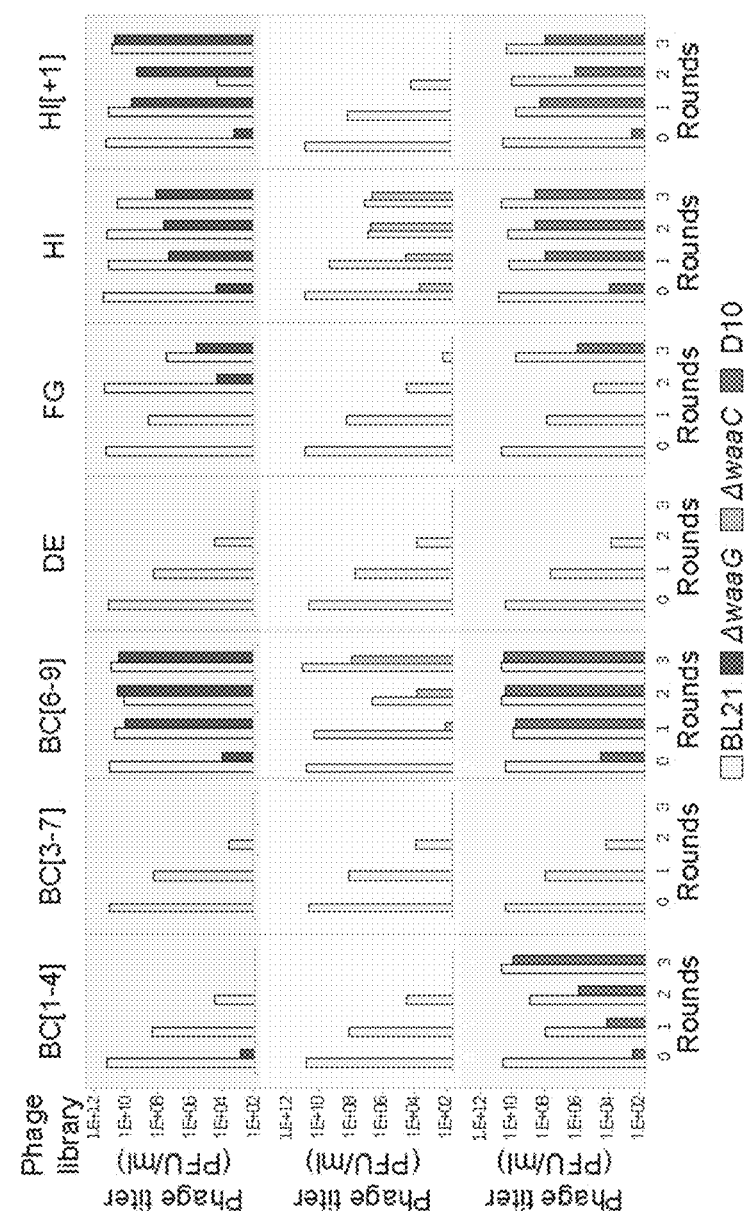
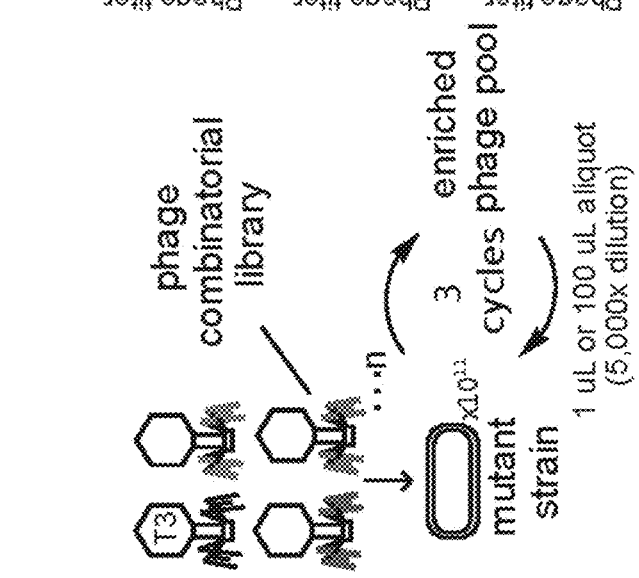
FIG. 30A
FIG. 30B

SEQUENCE LISTING

<160> NUMBER OF SEQ ID NOS: 186

<210> SEQ ID NO 1
<211> LENGTH: 53

```
<212> TYPE: DNA
<213> ORGANISM: Artificial Sequence
<220> FEATURE:
<223> OTHER INFORMATION: PST480 primer

<400> SEQUENCE: 1
gtacgaattc agctggatcc agacctaggg gatatattcc gcttcctcgc tca            53

<210> SEQ ID NO 2
<211> LENGTH: 50
<212> TYPE: DNA
<213> ORGANISM: Artificial Sequence
<220> FEATURE:
<223> OTHER INFORMATION: PST481 primer

<400> SEQUENCE: 2
gcatcccggg tgcaaagctt gacgtcggaa ttgccagctg ggcgccctc                 50

<210> SEQ ID NO 3
<211> LENGTH: 40
<212> TYPE: DNA
<213> ORGANISM: Artificial Sequence
<220> FEATURE:
<223> OTHER INFORMATION: PST575 primer

<400> SEQUENCE: 3
tagcggatcc tgaaggaacg tgacccaaac aaaccgtaca                           40

<210> SEQ ID NO 4
<211> LENGTH: 40
<212> TYPE: DNA
<213> ORGANISM: Artificial Sequence
<220> FEATURE:
<223> OTHER INFORMATION: PST576 primer

<400> SEQUENCE: 4
tcgacccggg atcttatcga ctaccttggc accaatctga                           40

<210> SEQ ID NO 5
<211> LENGTH: 26
<212> TYPE: DNA
<213> ORGANISM: Artificial Sequence
<220> FEATURE:
<223> OTHER INFORMATION: PST691 primer

<400> SEQUENCE: 5
gtactaagtg gggaggtaag tggctt                                          26

<210> SEQ ID NO 6
<211> LENGTH: 30
<212> TYPE: DNA
<213> ORGANISM: Artificial Sequence
<220> FEATURE:
<223> OTHER INFORMATION: PST692 primer

<400> SEQUENCE: 6
gtgtgatagt ccatccgtgg acttaaagta                                      30

<210> SEQ ID NO 7
<211> LENGTH: 26
<212> TYPE: DNA
<213> ORGANISM: Artificial Sequence
<220> FEATURE:
<223> OTHER INFORMATION: PST693 primer

<400> SEQUENCE: 7
```
aagccactta cctcccccact tagtac                                         26

<210> SEQ ID NO 8
<211> LENGTH: 30
<212> TYPE: DNA
<213> ORGANISM: Artificial Sequence
<220> FEATURE:
<223> OTHER INFORMATION: PST694 primer

<400> SEQUENCE: 8
tactttaagt ccacggatgg actatcacac                                      30

<210> SEQ ID NO 9
<211> LENGTH: 30
<212> TYPE: DNA
<213> ORGANISM: Artificial Sequence
<220> FEATURE:
<223> OTHER INFORMATION: PST1089 primer

<400> SEQUENCE: 9
ggtacctttc tcctctttaa tagctaaatc                                      30

<210> SEQ ID NO 10
<211> LENGTH: 29
<212> TYPE: DNA
<213> ORGANISM: Artificial Sequence
<220> FEATURE:
<223> OTHER INFORMATION: PST1090 primer

<400> SEQUENCE: 10
gtgcacggat cccatggtac gcgtgctag                                       29

<210> SEQ ID NO 11
<211> LENGTH: 45
<212> TYPE: DNA
<213> ORGANISM: Artificial Sequence
<220> FEATURE:
<223> OTHER INFORMATION: PST1091BL primer

<400> SEQUENCE: 11
ggagaaaggt accatgtcat tttgttggaa tgaaattaat tctgg                     45

<210> SEQ ID NO 12
<211> LENGTH: 46
<212> TYPE: DNA
<213> ORGANISM: Artificial Sequence
<220> FEATURE:
<223> OTHER INFORMATION: PST1092BL primer

<400> SEQUENCE: 12
gggatccgtg cacttattta tctaataaac attggtctga ttgtgc                    46

<210> SEQ ID NO 13
<211> LENGTH: 51
<212> TYPE: DNA
<213> ORGANISM: Artificial Sequence
<220> FEATURE:
<223> OTHER INFORMATION: PST816 primer

<400> SEQUENCE: 13
cctgtggggc ccatgcccta ggtcatgaga ttatcaaaaa ggatcttcac c              51

<210> SEQ ID NO 14
<211> LENGTH: 51
<212> TYPE: DNA
<213> ORGANISM: Artificial Sequence

```
<220> FEATURE:
<223> OTHER INFORMATION: PST817 primer

<400> SEQUENCE: 14
ggtgcagggc cctcgacaat tgtcagccaa tcgactggcg agcggcatcg c            51

<210> SEQ ID NO 15
<211> LENGTH: 49
<212> TYPE: DNA
<213> ORGANISM: Artificial Sequence
<220> FEATURE:
<223> OTHER INFORMATION: PST818 primer

<400> SEQUENCE: 15
tgcgaagggc ccggattcga attcgtgatc ttccgtcaca ggtaggcgc               49

<210> SEQ ID NO 16
<211> LENGTH: 54
<212> TYPE: DNA
<213> ORGANISM: Artificial Sequence
<220> FEATURE:
<223> OTHER INFORMATION: PST819 primer

<400> SEQUENCE: 16
gtggcagggc ccgcgtaagc tagcggcgcg ccatttaaat gaagttccta ttcc         54

<210> SEQ ID NO 17
<211> LENGTH: 60
<212> TYPE: DNA
<213> ORGANISM: Artificial Sequence
<220> FEATURE:
<223> OTHER INFORMATION: PST853 primer

<400> SEQUENCE: 17
cggatgcggg ttttgatcgt taaaacatcg tcgatgggcg gtgtaggctg gagctgcttc   60

<210> SEQ ID NO 18
<211> LENGTH: 60
<212> TYPE: DNA
<213> ORGANISM: Artificial Sequence
<220> FEATURE:
<223> OTHER INFORMATION: PST854 primer

<400> SEQUENCE: 18
accatctgat tcttcccata cccaccaatt aatcccggat atgggaatta gccatggtcc   60

<210> SEQ ID NO 19
<211> LENGTH: 60
<212> TYPE: DNA
<213> ORGANISM: Artificial Sequence
<220> FEATURE:
<223> OTHER INFORMATION: PST857 primer

<400> SEQUENCE: 19
cggtttgcag cgcgatttta tgcgtattgc tcagacagtc gtgtaggctg gagctgcttc   60

<210> SEQ ID NO 20
<211> LENGTH: 60
<212> TYPE: DNA
<213> ORGANISM: Artificial Sequence
<220> FEATURE:
<223> OTHER INFORMATION: PST858 primer

<400> SEQUENCE: 20
ccagaccacc cgttatgata tccgccgctt tctctggcag atgggaatta gccatggtcc   60
```

<210> SEQ ID NO 21
<211> LENGTH: 77
<212> TYPE: DNA
<213> ORGANISM: Artificial Sequence
<220> FEATURE:
<223> OTHER INFORMATION: PST695 primer
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t

<400> SEQUENCE: 21
cctgtgggag agtatcagtc tgagaaccmn nmnnmnnmnn mnnmnnmnnm nnmnnagccc        60
atacttgagt ccaggcc                                                     77

<210> SEQ ID NO 22
<211> LENGTH: 28
<212> TYPE: DNA
<213> ORGANISM: Artificial Sequence
<220> FEATURE:
<223> OTHER INFORMATION: PST696 primer

<400> SEQUENCE: 22
ggttctcaga ctgatactct cccacagg                                         28

<210> SEQ ID NO 23
<211> LENGTH: 66
<212> TYPE: DNA
<213> ORGANISM: Artificial Sequence
<220> FEATURE:
<223> OTHER INFORMATION: PST699 primer
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature

```
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 23
ggcagggtat ttaagaacat agcggataga nnknnknnkn nkacagcaat agccgtagag      60
gacgtg                                                                66

<210> SEQ ID NO 24
<211> LENGTH: 30
<212> TYPE: DNA
<213> ORGANISM: Artificial Sequence
<220> FEATURE:
<223> OTHER INFORMATION: PST700 primer

<400> SEQUENCE: 24
tctatccgct atgttcttaa atacccctgcc                                     30

<210> SEQ ID NO 25
<211> LENGTH: 73
<212> TYPE: DNA
<213> ORGANISM: Artificial Sequence
<220> FEATURE:
<223> OTHER INFORMATION: PST701 primer
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

<400> SEQUENCE: 25
aactggtcct gacggtatct acttccttnn knnknnknnk nnktggctaa aattccagat      60
acactctaat ggc                                                        73

<210> SEQ ID NO 26
<211> LENGTH: 28
<212> TYPE: DNA
<213> ORGANISM: Artificial Sequence
<220> FEATURE:
<223> OTHER INFORMATION: PST702 primer

<400> SEQUENCE: 26
aaggaagtag ataccgtcag gaccagtt                                        28

<210> SEQ ID NO 27
<211> LENGTH: 25
<212> TYPE: DNA
<213> ORGANISM: Artificial Sequence
<220> FEATURE:
<223> OTHER INFORMATION: PST794 primer
```

```
<400> SEQUENCE: 27
cttaatccat atgttgcgga atcgc                                          25

<210> SEQ ID NO 28
<211> LENGTH: 68
<212> TYPE: DNA
<213> ORGANISM: Artificial Sequence
<220> FEATURE:
<223> OTHER INFORMATION: PST795 primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 28
gcgattccgc aacatatgga ttaagnnknn knnknnknnk tggaacttct tccgaactgg    60
tcctgacg                                                             68

<210> SEQ ID NO 29
<211> LENGTH: 83
<212> TYPE: DNA
<213> ORGANISM: Artificial Sequence
<220> FEATURE:
<223> OTHER INFORMATION: PST800 primer
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
```

```
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 29
gacaatggcc tggactcaag tatgggctnn knnknnknnk nnknnknnkn nknnknnkgg    60
ttctcagact gatactctcc cac                                           83

<210> SEQ ID NO 30
<211> LENGTH: 28
<212> TYPE: DNA
<213> ORGANISM: Artificial Sequence
<220> FEATURE:
<223> OTHER INFORMATION: PST802 primer

<400> SEQUENCE: 30
agcccatact tgagtccagg ccattgtc                                      28

<210> SEQ ID NO 31
<211> LENGTH: 71
<212> TYPE: DNA
<213> ORGANISM: Artificial Sequence
<220> FEATURE:
<223> OTHER INFORMATION: PST803 primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 31
gggtatttaa gaacatagcg gatagannkn nknnknnkn knnknnkaca gcaatagccg    60
tagaggacgt g                                                        71

<210> SEQ ID NO 32
<211> LENGTH: 26
<212> TYPE: DNA
<213> ORGANISM: Artificial Sequence
<220> FEATURE:
<223> OTHER INFORMATION: PST805 primer

<400> SEQUENCE: 32
tctatccgct atgttcttaa ataccc                                        26
```

```
<210> SEQ ID NO 33
<211> LENGTH: 28
<212> TYPE: DNA
<213> ORGANISM: Artificial Sequence
<220> FEATURE:
<223> OTHER INFORMATION: PST696. primer

<400> SEQUENCE: 33
ggttctcaga ctgatactct cccacagg                                              28

<210> SEQ ID NO 34
<211> LENGTH: 77
<212> TYPE: DNA
<213> ORGANISM: Artificial Sequence
<220> FEATURE:
<223> OTHER INFORMATION: PST1252 primer
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 34
cctgtgggag agtatcagtc tgagaaccmn nmnnmnnmnn actaccacta gcagcagccc           60
atacttgagt ccaggcc                                                         77

<210> SEQ ID NO 35
<211> LENGTH: 77
<212> TYPE: DNA
<213> ORGANISM: Artificial Sequence
<220> FEATURE:
<223> OTHER INFORMATION: PST1253 primer
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t

<400> SEQUENCE: 35
cctgtgggag agtatcagtc tgagaacctc ctcccatgta actmnnmnnm nnmnnagccc           60
atacttgagt ccaggcc                                                         77

<210> SEQ ID NO 36
<211> LENGTH: 77
<212> TYPE: DNA
<213> ORGANISM: Artificial Sequence
<220> FEATURE:
<223> OTHER INFORMATION: PST1254 primer
```

<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t

<400> SEQUENCE: 36
cctgtgggag agtatcagtc tgagaacctc ctccmnnmnn mnnmnnmnna gcagcagccc    60
atacttgagt ccaggcc                                                  77

<210> SEQ ID NO 37
<211> LENGTH: 72
<212> TYPE: DNA
<213> ORGANISM: Artificial Sequence
<220> FEATURE:
<223> OTHER INFORMATION: PST1255 primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 37
ctgactggtc tctagccmnn mnnmnnmnna ctaccactag cagcagccca tacttgagtc    60
caggccattg tc                                                       72

<210> SEQ ID NO 38
<211> LENGTH: 73
<212> TYPE: DNA
<213> ORGANISM: Artificial Sequence
<220> FEATURE:
<223> OTHER INFORMATION: PST1256 primer
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)

<223> OTHER INFORMATION: n is a, c, g, or t

<400> SEQUENCE: 38
ctgacttggt ctctagcctc ctcccatgta actmnnmnnm nnmnnagccc atacttgagt    60
ccaggccatt gtc    73

<210> SEQ ID NO 39
<211> LENGTH: 71
<212> TYPE: DNA
<213> ORGANISM: Artificial Sequence
<220> FEATURE:
<223> OTHER INFORMATION: PST1257 primer
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t

<400> SEQUENCE: 39
ctgactggtc tcagcctcct ccmnnmnnmn nmnnmnnagc agcagcccat acttgagtcc    60
aggccattgt c    71

<210> SEQ ID NO 40
<211> LENGTH: 41
<212> TYPE: DNA
<213> ORGANISM: Artificial Sequence
<220> FEATURE:
<223> OTHER INFORMATION: PST957 primer

<400> SEQUENCE: 40
agtcagggtc tctggttctc agactgatac tctcccacag g    41

<210> SEQ ID NO 41
<211> LENGTH: 59
<212> TYPE: DNA
<213> ORGANISM: Artificial Sequence
<220> FEATURE:
<223> OTHER INFORMATION: PST958 primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature

```
<222> LOCATION: (33)..(34)
<223> OTHER INFORMATION: n is a, c, g, or t

<400> SEQUENCE: 41
ctgactggtc tctattccam nnmnnmnnmn nmnncttaat ccatatgttg cggaatcgc      59

<210> SEQ ID NO 42
<211> LENGTH: 44
<212> TYPE: DNA
<213> ORGANISM: Artificial Sequence
<220> FEATURE:
<223> OTHER INFORMATION: PST961 primer

<400> SEQUENCE: 42
agtcagggtc tctgaatttc ttccgaactg gtcctgacgg tatc                     44

<210> SEQ ID NO 43
<211> LENGTH: 60
<212> TYPE: DNA
<213> ORGANISM: Artificial Sequence
<220> FEATURE:
<223> OTHER INFORMATION: PST962 primer
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t

<400> SEQUENCE: 43
ctgactggtc tctcaaccam nnmnnmnnmn nmnnaaggaa gtagataccg tcaggaccag     60

<210> SEQ ID NO 44
<211> LENGTH: 42
<212> TYPE: DNA
<213> ORGANISM: Artificial Sequence
<220> FEATURE:
<223> OTHER INFORMATION: PST965 primer

<400> SEQUENCE: 44
agtcagggtc tcttggctaa aattccagat acactctaat gg                       42

<210> SEQ ID NO 45
<211> LENGTH: 58
<212> TYPE: DNA
<213> ORGANISM: Artificial Sequence
<220> FEATURE:
<223> OTHER INFORMATION: PST966 primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
```

```
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t

<400> SEQUENCE: 45
ctgactggtc tctcggtmnn mnnmnnmnnt ctatccgcta tgttcttaaa taccctgc      58

<210> SEQ ID NO 46
<211> LENGTH: 61
<212> TYPE: DNA
<213> ORGANISM: Artificial Sequence
<220> FEATURE:
<223> OTHER INFORMATION: PST1258 primer
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 46
ctgactggtc tctcggtmnn mnnmnnmnnm nntctatccg ctatgttctt aaataccctg    60
c                                                                   61

<210> SEQ ID NO 47
<211> LENGTH: 37
<212> TYPE: DNA
<213> ORGANISM: Artificial Sequence
<220> FEATURE:
<223> OTHER INFORMATION: PST969 primer

<400> SEQUENCE: 47
agtcagggtc tctaccgcaa tagccgtaga ggacgtg                             37

<210> SEQ ID NO 48
<211> LENGTH: 30
<212> TYPE: DNA
<213> ORGANISM: Artificial Sequence
<220> FEATURE:
<223> OTHER INFORMATION: T3(BC)

<400> SEQUENCE: 48
gctgctagtg gtagttacat gggaggaggt                                     30

<210> SEQ ID NO 49
<211> LENGTH: 30
<212> TYPE: DNA
<213> ORGANISM: Artificial Sequence
<220> FEATURE:
<223> OTHER INFORMATION: T3(BC:AASGSHMHT)

<400> SEQUENCE: 49
```

```
gctgctagtg gtagtcatat gcatactggc                                              30

<210> SEQ ID NO 50
<211> LENGTH: 30
<212> TYPE: DNA
<213> ORGANISM: Artificial Sequence
<220> FEATURE:
<223> OTHER INFORMATION: T3(BC:AAGKNALGG)

<400> SEQUENCE: 50
gctgctggta agaatgcgct tggaggaggt                                              30

<210> SEQ ID NO 51
<211> LENGTH: 30
<212> TYPE: DNA
<213> ORGANISM: Artificial Sequence
<220> FEATURE:
<223> OTHER INFORMATION: T3(BC:AARKNALGG)

<400> SEQUENCE: 51
gctgctagga agcggggtct gggaggaggt                                              30

<210> SEQ ID NO 52
<211> LENGTH: 30
<212> TYPE: DNA
<213> ORGANISM: Artificial Sequence
<220> FEATURE:
<223> OTHER INFORMATION: T3(BC:MHGKSYMGG)

<400> SEQUENCE: 52
atgcatggta agagttacat gggaggaggt                                              30

<210> SEQ ID NO 53
<211> LENGTH: 30
<212> TYPE: DNA
<213> ORGANISM: Artificial Sequence
<220> FEATURE:
<223> OTHER INFORMATION: T3(BC:AIGRSHLKS)

<400> SEQUENCE: 53
gcgattggta ggtctcattt gaagagtggt                                              30

<210> SEQ ID NO 54
<211> LENGTH: 30
<212> TYPE: DNA
<213> ORGANISM: Artificial Sequence
<220> FEATURE:
<223> OTHER INFORMATION: T3(HI:AASGSKLRH)

<400> SEQUENCE: 54
gctgctagtg gtagtaagct gaggcatggc                                              30

<210> SEQ ID NO 55
<211> LENGTH: 30
<212> TYPE: DNA
<213> ORGANISM: Artificial Sequence
<220> FEATURE:
<223> OTHER INFORMATION: T3(BC:AASGSHMHK)

<400> SEQUENCE: 55
gctgctagtg gtagtcatat gcatactggc                                              30

<210> SEQ ID NO 56
<211> LENGTH: 15
<212> TYPE: DNA
```

```
<213> ORGANISM: Artificial Sequence
<220> FEATURE:
<223> OTHER INFORMATION: T3(FG)

<400> SEQUENCE: 56
tcagccgagg gcggt                                              15

<210> SEQ ID NO 57
<211> LENGTH: 15
<212> TYPE: DNA
<213> ORGANISM: Artificial Sequence
<220> FEATURE:
<223> OTHER INFORMATION: T3(FG:PLDGH)

<400> SEQUENCE: 57
ccgttggatg gtcat                                              15

<210> SEQ ID NO 58
<211> LENGTH: 18
<212> TYPE: DNA
<213> ORGANISM: Artificial Sequence
<220> FEATURE:
<223> OTHER INFORMATION: T3(HI)

<400> SEQUENCE: 58
agagatgcgc ctccaaca                                           18

<210> SEQ ID NO 59
<211> LENGTH: 21
<212> TYPE: DNA
<213> ORGANISM: Artificial Sequence
<220> FEATURE:
<223> OTHER INFORMATION: T3(HI:GHLSL)

<400> SEQUENCE: 59
agacatgggt tgtctttgac c                                       21

<210> SEQ ID NO 60
<211> LENGTH: 21
<212> TYPE: DNA
<213> ORGANISM: Artificial Sequence
<220> FEATURE:
<223> OTHER INFORMATION: T3(HI:LGLAV)

<400> SEQUENCE: 60
agactgggtc ttgctgttac c                                       21

<210> SEQ ID NO 61
<211> LENGTH: 18
<212> TYPE: DNA
<213> ORGANISM: Artificial Sequence
<220> FEATURE:
<223> OTHER INFORMATION: T3(HI:HSVV)

<400> SEQUENCE: 61
agacattcgg tggttaca                                           18

<210> SEQ ID NO 62
<211> LENGTH: 18
<212> TYPE: DNA
<213> ORGANISM: Artificial Sequence
<220> FEATURE:
<223> OTHER INFORMATION: T3(HI:NCHV)

<400> SEQUENCE: 62
agaaattgtc atgtgacc                                           18
```

<210> SEQ ID NO 63
<211> LENGTH: 18
<212> TYPE: DNA
<213> ORGANISM: Artificial Sequence
<220> FEATURE:
<223> OTHER INFORMATION: T3(HI:HTGI)

<400> SEQUENCE: 63
agacatacgg gtattacc                                                   18

<210> SEQ ID NO 64
<211> LENGTH: 21
<212> TYPE: DNA
<213> ORGANISM: Artificial Sequence
<220> FEATURE:
<223> OTHER INFORMATION: T3(HI:AYASP)

<400> SEQUENCE: 64
agagcttatg cgtctccaac a                                               21

<210> SEQ ID NO 65
<211> LENGTH: 18
<212> TYPE: DNA
<213> ORGANISM: Artificial Sequence
<220> FEATURE:
<223> OTHER INFORMATION: T3(HI:KSGV)

<400> SEQUENCE: 65
agaaagagtg gggtgaca                                                   18

<210> SEQ ID NO 66
<211> LENGTH: 18
<212> TYPE: DNA
<213> ORGANISM: Artificial Sequence
<220> FEATURE:
<223> OTHER INFORMATION: T3(HI:R546G KAGI)

<400> SEQUENCE: 66
ggaaaggcgg ggattaca                                                   18

<210> SEQ ID NO 67
<211> LENGTH: 18
<212> TYPE: DNA
<213> ORGANISM: Artificial Sequence
<220> FEATURE:
<223> OTHER INFORMATION: T3(HI:HTHP)

<400> SEQUENCE: 67
agacatactc atcctacc                                                   18

<210> SEQ ID NO 68
<211> LENGTH: 18
<212> TYPE: DNA
<213> ORGANISM: Artificial Sequence
<220> FEATURE:
<223> OTHER INFORMATION: T3(HI:HSQP)

<400> SEQUENCE: 68
agacattctc agccgacc                                                   18

<210> SEQ ID NO 69
<211> LENGTH: 18
<212> TYPE: DNA
<213> ORGANISM: Artificial Sequence
<220> FEATURE:

```
<223> OTHER INFORMATION: T3(HI:KLNI)

<400> SEQUENCE: 69
agaaagctga atattaca                                                 18

<210> SEQ ID NO 70
<211> LENGTH: 18
<212> TYPE: DNA
<213> ORGANISM: Artificial Sequence
<220> FEATURE:
<223> OTHER INFORMATION: T3(HI:GARV)

<400> SEQUENCE: 70
agaggggcga gggtgaca                                                 18

<210> SEQ ID NO 71
<211> LENGTH: 18
<212> TYPE: DNA
<213> ORGANISM: Artificial Sequence
<220> FEATURE:
<223> OTHER INFORMATION: T3(HI:ASRV)

<400> SEQUENCE: 71
agagcgagta gggtgaca                                                 18

<210> SEQ ID NO 72
<211> LENGTH: 18
<212> TYPE: DNA
<213> ORGANISM: Artificial Sequence
<220> FEATURE:
<223> OTHER INFORMATION: T3(HI:KAGI)

<400> SEQUENCE: 72
agaaaggcgg ggattaca                                                 18

<210> SEQ ID NO 73
<211> LENGTH: 18
<212> TYPE: DNA
<213> ORGANISM: Artificial Sequence
<220> FEATURE:
<223> OTHER INFORMATION: T3(HI:RTFI)

<400> SEQUENCE: 73
agacgtactt ttattaca                                                 18

<210> SEQ ID NO 74
<211> LENGTH: 27
<212> TYPE: DNA
<213> ORGANISM: Artificial Sequence
<220> FEATURE:
<223> OTHER INFORMATION: T3(HI:RDIRLSI)

<400> SEQUENCE: 74
agacgggata ttaggcttag tattaca                                       27

<210> SEQ ID NO 75
<211> LENGTH: 18
<212> TYPE: DNA
<213> ORGANISM: Artificial Sequence
<220> FEATURE:
<223> OTHER INFORMATION: T3(HI:RFFV)

<400> SEQUENCE: 75
agacgttttt ttgttacc                                                 18
```

```
<210> SEQ ID NO 76
<211> LENGTH: 10
<212> TYPE: PRT
<213> ORGANISM: Artificial Sequence
<220> FEATURE:
<223> OTHER INFORMATION: T3(BC) aa

<400> SEQUENCE: 76

Ala Ala Ser Gly Ser Tyr Met Gly Gly Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: T3(BC:AASGSHMHT) aa

<400> SEQUENCE: 77

Ala Ala Ser Gly Ser His Met His Thr Gly
1               5                   10

<210> SEQ ID NO 78
<211> LENGTH: 10
<212> TYPE: PRT
<213> ORGANISM: Artificial Sequence
<220> FEATURE:
<223> OTHER INFORMATION: T3(BC:AAGKNALGG) aa

<400> SEQUENCE: 78

Ala Ala Gly Lys Asn Ala Leu Gly Gly Gly
1               5                   10

<210> SEQ ID NO 79
<211> LENGTH: 10
<212> TYPE: PRT
<213> ORGANISM: Artificial Sequence
<220> FEATURE:
<223> OTHER INFORMATION: T3(BC:AARKARGLGG) aa

<400> SEQUENCE: 79

Ala Ala Arg Lys Arg Gly Leu Gly Gly Gly
1               5                   10

<210> SEQ ID NO 80
<211> LENGTH: 10
<212> TYPE: PRT
<213> ORGANISM: Artificial Sequence
<220> FEATURE:
<223> OTHER INFORMATION: T3(BC:MHGKSYMGG) aa

<400> SEQUENCE: 80

Met His Gly Lys Ser Tyr Met Gly Gly Gly
1               5                   10

<210> SEQ ID NO 81
<211> LENGTH: 10
<212> TYPE: PRT
<213> ORGANISM: Artificial Sequence
<220> FEATURE:
<223> OTHER INFORMATION: T3(BC:AIGRSHLKS) aa

<400> SEQUENCE: 81

Ala Ile Gly Arg Ser His Leu Lys Ser Gly
1               5                   10

<210> SEQ ID NO 82
```

```
<211> LENGTH: 10
<212> TYPE: PRT
<213> ORGANISM: Artificial Sequence
<220> FEATURE:
<223> OTHER INFORMATION: T3(HI:AASGSKLRH) aa

<400> SEQUENCE: 82

Ala Ala Ser Gly Ser Lys Leu Arg His Gly
1               5                   10

<210> SEQ ID NO 83
<211> LENGTH: 10
<212> TYPE: PRT
<213> ORGANISM: Artificial Sequence
<220> FEATURE:
<223> OTHER INFORMATION: T3(BC:AASGSHMHK) aa

<400> SEQUENCE: 83

Ala Ala Ser Gly Ser His Met His Lys Gly
1               5                   10

<210> SEQ ID NO 84
<211> LENGTH: 5
<212> TYPE: PRT
<213> ORGANISM: Artificial Sequence
<220> FEATURE:
<223> OTHER INFORMATION: T3(FG) aa

<400> SEQUENCE: 84

Ser Ala Glu Gly Gly
1               5

<210> SEQ ID NO 85
<211> LENGTH: 5
<212> TYPE: PRT
<213> ORGANISM: Artificial Sequence
<220> FEATURE:
<223> OTHER INFORMATION: T3(FG:PLDGH) aa

<400> SEQUENCE: 85

Pro Leu Asp Gly His
1               5

<210> SEQ ID NO 86
<211> LENGTH: 6
<212> TYPE: PRT
<213> ORGANISM: Artificial Sequence
<220> FEATURE:
<223> OTHER INFORMATION: T3(HI) aa

<400> SEQUENCE: 86

Arg Asp Ala Pro Pro Thr
1               5

<210> SEQ ID NO 87
<211> LENGTH: 7
<212> TYPE: PRT
<213> ORGANISM: Artificial Sequence
<220> FEATURE:
<223> OTHER INFORMATION: T3(HI:GHLSL) aa

<400> SEQUENCE: 87

Arg Gly His Leu Ser Leu Thr
1               5

<210> SEQ ID NO 88
<211> LENGTH: 7
```

<212> TYPE: PRT
<213> ORGANISM: Artificial Sequence
<220> FEATURE:
<223> OTHER INFORMATION: T3(HI:LGLAV) aa

<400> SEQUENCE: 88

Arg Leu Gly Leu Ala Val Thr
1 5

<210> SEQ ID NO 89
<211> LENGTH: 6
<212> TYPE: PRT
<213> ORGANISM: Artificial Sequence
<220> FEATURE:
<223> OTHER INFORMATION: T3(HI:HSVV) aa

<400> SEQUENCE: 89

Arg His Ser Val Val Thr
1 5

<210> SEQ ID NO 90
<211> LENGTH: 6
<212> TYPE: PRT
<213> ORGANISM: Artificial Sequence
<220> FEATURE:
<223> OTHER INFORMATION: T3(HI:NCHV) aa

<400> SEQUENCE: 90

Arg Asn Cys His Val Thr
1 5

<210> SEQ ID NO 91
<211> LENGTH: 6
<212> TYPE: PRT
<213> ORGANISM: Artificial Sequence
<220> FEATURE:
<223> OTHER INFORMATION: T3(HI:HTGI) aa

<400> SEQUENCE: 91

Arg His Thr Gly Ile Thr
1 5

<210> SEQ ID NO 92
<211> LENGTH: 7
<212> TYPE: PRT
<213> ORGANISM: Artificial Sequence
<220> FEATURE:
<223> OTHER INFORMATION: T3(HI:AYASP) aa

<400> SEQUENCE: 92

Arg Ala Tyr Ala Ser Pro Thr
1 5

<210> SEQ ID NO 93
<211> LENGTH: 6
<212> TYPE: PRT
<213> ORGANISM: Artificial Sequence
<220> FEATURE:
<223> OTHER INFORMATION: T3(HI:KSGV) aa

<400> SEQUENCE: 93

Arg Lys Ser Gly Val Thr
1 5

<210> SEQ ID NO 94
<211> LENGTH: 6
<212> TYPE: PRT

```
<213> ORGANISM: Artificial Sequence
<220> FEATURE:
<223> OTHER INFORMATION: T3(HI:R546G KAGI) aa

<400> SEQUENCE: 94

Gly Lys Ala Gly Ile Thr
1               5

<210> SEQ ID NO 95
<211> LENGTH: 6
<212> TYPE: PRT
<213> ORGANISM: Artificial Sequence
<220> FEATURE:
<223> OTHER INFORMATION: T3(HI:HTHP) aa

<400> SEQUENCE: 95

Arg His Thr His Pro Thr
1               5

<210> SEQ ID NO 96
<211> LENGTH: 6
<212> TYPE: PRT
<213> ORGANISM: Artificial Sequence
<220> FEATURE:
<223> OTHER INFORMATION: T3(HI:HSQP) aa

<400> SEQUENCE: 96

Arg His Ser Gln Pro Thr
1               5

<210> SEQ ID NO 97
<211> LENGTH: 6
<212> TYPE: PRT
<213> ORGANISM: Artificial Sequence
<220> FEATURE:
<223> OTHER INFORMATION: T3(HI:KLNI) aa

<400> SEQUENCE: 97

Arg Lys Leu Asn Ile Thr
1               5

<210> SEQ ID NO 98
<211> LENGTH: 6
<212> TYPE: PRT
<213> ORGANISM: Artificial Sequence
<220> FEATURE:
<223> OTHER INFORMATION: T3(HI:GARV) aa

<400> SEQUENCE: 98

Arg Gly Ala Arg Val Thr
1               5

<210> SEQ ID NO 99
<211> LENGTH: 6
<212> TYPE: PRT
<213> ORGANISM: Artificial Sequence
<220> FEATURE:
<223> OTHER INFORMATION: T3(HI:ASRV) aa

<400> SEQUENCE: 99

Arg Ala Ser Arg Val Thr
1               5

<210> SEQ ID NO 100
<211> LENGTH: 6
<212> TYPE: PRT
<213> ORGANISM: Artificial Sequence
```

```
<220> FEATURE:
<223> OTHER INFORMATION: T3(HI:KAGI) aa

<400> SEQUENCE: 100

Arg Lys Ala Gly Ile Thr
1               5

<210> SEQ ID NO 101
<211> LENGTH: 6
<212> TYPE: PRT
<213> ORGANISM: Artificial Sequence
<220> FEATURE:
<223> OTHER INFORMATION: T3(HI:RTFI) aa

<400> SEQUENCE: 101

Arg Arg Thr Phe Ile Thr
1               5

<210> SEQ ID NO 102
<211> LENGTH: 9
<212> TYPE: PRT
<213> ORGANISM: Artificial Sequence
<220> FEATURE:
<223> OTHER INFORMATION: T3(HI:RDIRLSI) aa

<400> SEQUENCE: 102

Arg Arg Asp Ile Arg Leu Ser Ile Thr
1               5

<210> SEQ ID NO 103
<211> LENGTH: 6
<212> TYPE: PRT
<213> ORGANISM: Artificial Sequence
<220> FEATURE:
<223> OTHER INFORMATION: T3(HI:RFFV) aa

<400> SEQUENCE: 103

Arg Arg Phe Phe Val Thr
1               5

<210> SEQ ID NO 104
<211> LENGTH: 98
<212> TYPE: DNA
<213> ORGANISM: Artificial Sequence
<220> FEATURE:
<223> OTHER INFORMATION: ppAY15
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 104
ccatcggggc ccgtacggaa gaagttccam nnmnnmnnmn nmnncttaat ccagatattg    60
```
cggaagcgga gatcctgtga aacagtcaca cttacccc        98

<210> SEQ ID NO 105
<211> LENGTH: 85
<212> TYPE: DNA
<213> ORGANISM: Artificial Sequence
<220> FEATURE:
<223> OTHER INFORMATION: ppAY16
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 105
ccgtacgggc cccgatggaa tctacttcat annknnknnk nnknnktggt tacgattcca        60
aatacactcc aacggcctcg gattc        85

<210> SEQ ID NO 106
<211> LENGTH: 100
<212> TYPE: DNA
<213> ORGANISM: Artificial Sequence
<220> FEATURE:
<223> OTHER INFORMATION: ppAY17
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t

```
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t

<400> SEQUENCE: 106
ctgtgaaaca gtcacactta ccccmnmnn mnmnnmnna gaccacacct gagtccamnn      60 mnnmnmnnm nnmnnmnngc tgtcacgtag gtaagcatca                          100

<210> SEQ ID NO 107
<211> LENGTH: 73
<212> TYPE: DNA
<213> ORGANISM: Artificial Sequence
<220> FEATURE:
<223> OTHER INFORMATION: ppAY18
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 107
ctccaacggc ctcggattca agaatattgc agacagtnnk nnknnknnka atgcaatcat    60
ggtggagaac gag                                                      73

<210> SEQ ID NO 108
<211> LENGTH: 72
<212> TYPE: DNA
<213> ORGANISM: Artificial Sequence
<220> FEATURE:
<223> OTHER INFORMATION: PST494 primer
<220> FEATURE:
<221> NAME/KEY: misc_feature
<222> LOCATION: (27)..(47)
<223> OTHER INFORMATION: n is a, c, g, or t

<400> SEQUENCE: 108
agacgaagac tgcacacctg agtccannnn nnnnnnnnn nnnnnnngct gtcacgtagg    60
taagcatcca gc                                                       72

<210> SEQ ID NO 109
<211> LENGTH: 71
<212> TYPE: DNA
<213> ORGANISM: Artificial Sequence
<220> FEATURE:
<223> OTHER INFORMATION: PST494bis primer
<220> FEATURE:
<221> NAME/KEY: misc_feature
<222> LOCATION: (27)..(28)
<223> OTHER INFORMATION: n is a, c, g, or t
<220> FEATURE:
```

```
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 109
tgcaggtctc tcacacctga gtccamnnmn nmnnmnnmmn mnnmnngctg tcacgtaggt    60
aagcatcaag c                                                        71

<210> SEQ ID NO 110
<211> LENGTH: 82
<212> TYPE: DNA
<213> ORGANISM: Artificial Sequence
<220> FEATURE:
<223> OTHER INFORMATION: PST495 primer
<220> FEATURE:
<221> NAME/KEY: misc_feature
<222> LOCATION: (45)..(56)
<223> OTHER INFORMATION: n is a, c, g, or t

<400> SEQUENCE: 110
tgcaggtctc taacggcctc ggattcaaga atattgcaga cagtnnnnnn nnnnnnaatg    60
caatcatggt ggagaacgag ta                                            82

<210> SEQ ID NO 111
<211> LENGTH: 82
<212> TYPE: DNA
<213> ORGANISM: Artificial Sequence
<220> FEATURE:
<223> OTHER INFORMATION: PST495bis primer
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t

<400> SEQUENCE: 111
tgcaggtctc taacggcctc ggattcaaga atattgcaga cagtnnknnk nnknnkaatg    60
caatcatggt ggagaacgag ta                                            82
```

```
<210> SEQ ID NO 112
<211> LENGTH: 89
<212> TYPE: DNA
<213> ORGANISM: Artificial Sequence
<220> FEATURE:
<223> OTHER INFORMATION: PST496 primer
<220> FEATURE:
<221> NAME/KEY: misc_feature
<222> LOCATION: (21)..(35)
<223> OTHER INFORMATION: n is a, c, g, or t

<400> SEQUENCE: 112
gtctgaagac tgtgtggtct nnnnnnnnnn nnnnnggggt aagtgtgact gtttcacagg    60
atctccgctt ccgcaatatc tggattaag                                      89

<210> SEQ ID NO 113
<211> LENGTH: 79
<212> TYPE: DNA
<213> ORGANISM: Artificial Sequence
<220> FEATURE:
<223> OTHER INFORMATION: PST497 primer
<220> FEATURE:
<221> NAME/KEY: misc_feature
<222> LOCATION: (40)..(54)
<223> OTHER INFORMATION: n is a, c, g, or t

<400> SEQUENCE: 113
gagacgccgt ctcacggggc cagtacggaa gaagttccan nnnnnnnnnn nnnncttaat    60
ccagatattg cggaagcgg                                                 79

<210> SEQ ID NO 114
<211> LENGTH: 85
<212> TYPE: DNA
<213> ORGANISM: Artificial Sequence
<220> FEATURE:
<223> OTHER INFORMATION: PST498 primer
<220> FEATURE:
<221> NAME/KEY: misc_feature
<222> LOCATION: (32)..(46)
<223> OTHER INFORMATION: n is a, c, g, or t

<400> SEQUENCE: 114
cggcgtctca cccgatggaa tctacttcat annnnnnnnn nnnnnntggt tacgattcca    60
aatacactcc aacgagagac ctgca                                          85

<210> SEQ ID NO 115
<211> LENGTH: 24
<212> TYPE: DNA
<213> ORGANISM: Artificial Sequence
<220> FEATURE:
<223> OTHER INFORMATION: PST499 primer

<400> SEQUENCE: 115
tgcaggtctc tcgttggagt gtat                                           24

<210> SEQ ID NO 116
<211> LENGTH: 65
<212> TYPE: DNA
<213> ORGANISM: Artificial Sequence
<220> FEATURE:
<223> OTHER INFORMATION: PST510 primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
```

```
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 116
ccgcttccgc aatatctgga ttaagnnknn knnknnknnk tggaacttct tccgtactgg      60
ccccg                                                                  65

<210> SEQ ID NO 117
<211> LENGTH: 96
<212> TYPE: DNA
<213> ORGANISM: Artificial Sequence
<220> FEATURE:
<223> OTHER INFORMATION: PST511 primer
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 117
tgcaggtctc tcgttggagt gtatttggaa tcgtaaccam nnmnnmnnmn nmnntatgaa      60
gtagattcca tcggggccag tacggaagaa gttcca                                96

<210> SEQ ID NO 118
<211> LENGTH: 88
<212> TYPE: DNA
<213> ORGANISM: Artificial Sequence
<220> FEATURE:
<223> OTHER INFORMATION: PST512 primer
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
```

<222> LOCATION: (32)..(33)
<223> OTHER INFORMATION: n is a, c, g, or t

<400> SEQUENCE: 118
tgcaggtctc ttgtggtctn nknnknnknn knnkggggta agtgtgactg tttcacagga    60
tctccgcttc cgcaatatct ggattaag    88

<210> SEQ ID NO 119
<211> LENGTH: 22
<212> TYPE: DNA
<213> ORGANISM: Artificial Sequence
<220> FEATURE:
<223> OTHER INFORMATION: PST703 primer

<400> SEQUENCE: 119
ggcctggact caagtatggg ct    22

<210> SEQ ID NO 120
<211> LENGTH: 24
<212> TYPE: DNA
<213> ORGANISM: Artificial Sequence
<220> FEATURE:
<223> OTHER INFORMATION: PST704 primer

<400> SEQUENCE: 120
cacgtcctct acggctattg ctgt    24

<210> SEQ ID NO 121
<211> LENGTH: 22
<212> TYPE: DNA
<213> ORGANISM: Artificial Sequence
<220> FEATURE:
<223> OTHER INFORMATION: PST705 primer

<400> SEQUENCE: 121
agcccatact tgagtccagg cc    22

<210> SEQ ID NO 122
<211> LENGTH: 24
<212> TYPE: DNA
<213> ORGANISM: Artificial Sequence
<220> FEATURE:
<223> OTHER INFORMATION: PST706 primer

<400> SEQUENCE: 122
acagcaatag ccgtagagga cgtg    24

<210> SEQ ID NO 123
<211> LENGTH: 77
<212> TYPE: DNA
<213> ORGANISM: Artificial Sequence
<220> FEATURE:
<223> OTHER INFORMATION: PST767 primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)

```
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 123
gtactaagtg gggaggtaag tggcttnnkn nknnknnknn knnknnktac gttaagaaga       60
caatggcctg gactcaa                                                     77

<210> SEQ ID NO 124
<211> LENGTH: 30
<212> TYPE: DNA
<213> ORGANISM: Artificial Sequence
<220> FEATURE:
<223> OTHER INFORMATION: PST768 primer

<400> SEQUENCE: 124
ggccattgtc ttcttaacgt aagtatcgtt                                       30

<210> SEQ ID NO 125
<211> LENGTH: 74
<212> TYPE: DNA
<213> ORGANISM: Artificial Sequence
<220> FEATURE:
<223> OTHER INFORMATION: PST769 primer
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 125
aacgatactt acgttaagaa gacaatggcc nnknnknnkn nknnknnkgc tgctagtggt       60
agttacatgg gagg                                                        74

<210> SEQ ID NO 126
<211> LENGTH: 27
<212> TYPE: DNA
<213> ORGANISM: Artificial Sequence
<220> FEATURE:
<223> OTHER INFORMATION: PST770 primer

<400> SEQUENCE: 126
```
tcctcccatg taactaccac tagcagc                                             27

<210> SEQ ID NO 127
<211> LENGTH: 78
<212> TYPE: DNA
<213> ORGANISM: Artificial Sequence
<220> FEATURE:
<223> OTHER INFORMATION: PST771 primer
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 127
gctgctagtg gtagttacat gggaggannk nnknnknnkn nknnknnkcc acaggacttg        60
cgattccgca acatatgg                                                      78

<210> SEQ ID NO 128
<211> LENGTH: 26
<212> TYPE: DNA
<213> ORGANISM: Artificial Sequence
<220> FEATURE:
<223> OTHER INFORMATION: PST772 primer

<400> SEQUENCE: 128
gcggaatcgc aagtcctgtg ggagag                                             26

<210> SEQ ID NO 129
<211> LENGTH: 71
<212> TYPE: DNA
<213> ORGANISM: Artificial Sequence
<220> FEATURE:
<223> OTHER INFORMATION: PST773 primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)

<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 129
ctctcccaca ggacttgcga ttccgcnnkn knnknnknn kaccagaaac aactattgga    60
acttcttccg a                                                        71

<210> SEQ ID NO 130
<211> LENGTH: 30
<212> TYPE: DNA
<213> ORGANISM: Artificial Sequence
<220> FEATURE:
<223> OTHER INFORMATION: PST774 primer

<400> SEQUENCE: 130
atagttgttt ctggtcttaa tccatatgtt                                    30

<210> SEQ ID NO 131
<211> LENGTH: 76
<212> TYPE: DNA
<213> ORGANISM: Artificial Sequence
<220> FEATURE:
<223> OTHER INFORMATION: PST775 primer
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 131
aacatatgga ttaagaccag aaacaactat nnknnknnkn nknnknnkgg tcctgacggt    60
atctacttcc tttcag                                                   76

<210> SEQ ID NO 132
<211> LENGTH: 26
<212> TYPE: DNA
<213> ORGANISM: Artificial Sequence
<220> FEATURE:
<223> OTHER INFORMATION: PST776 primer

<400> SEQUENCE: 132
gtcaggacca gttcggaaga agttcc                                        26

<210> SEQ ID NO 133
<211> LENGTH: 71
<212> TYPE: DNA
<213> ORGANISM: Artificial Sequence

```
<220> FEATURE:
<223> OTHER INFORMATION: PST777 primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 133
ggaacttctt ccgaactggt cctgacnnkn nknnknnknn ktcagccgag ggcggttggc      60
taaaattcca g                                                          71

<210> SEQ ID NO 134
<211> LENGTH: 30
<212> TYPE: DNA
<213> ORGANISM: Artificial Sequence
<220> FEATURE:
<223> OTHER INFORMATION: PST778 primer

<400> SEQUENCE: 134
accgccctcg gctgaaagga agtagatacc                                      30

<210> SEQ ID NO 135
<211> LENGTH: 81
<212> TYPE: DNA
<213> ORGANISM: Artificial Sequence
<220> FEATURE:
<223> OTHER INFORMATION: PST779 primer
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 135
```
ggtatctact tcctttcagc cgagggcggt nnknnknnkn nknnknnknn ktctaatggc    60
agggtattta agaacatagc g    81

<210> SEQ ID NO 136
<211> LENGTH: 33
<212> TYPE: DNA
<213> ORGANISM: Artificial Sequence
<220> FEATURE:
<223> OTHER INFORMATION: PST780 primer

<400> SEQUENCE: 136
gccattagag tgtatctgga attttagcca acc    33

<210> SEQ ID NO 137
<211> LENGTH: 79
<212> TYPE: DNA
<213> ORGANISM: Artificial Sequence
<220> FEATURE:
<223> OTHER INFORMATION: PST781 primer
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t

<400> SEQUENCE: 137
ggctaaaatt ccagatacac tctaatggcn nknnknnknn knnknnknnk nnknnkgatg    60
cgcctccaac agcaatagc    79

<210> SEQ ID NO 138
<211> LENGTH: 28
<212> TYPE: DNA
<213> ORGANISM: Artificial Sequence
<220> FEATURE:
<223> OTHER INFORMATION: PST782 primer

<400> SEQUENCE: 138
tggaggcgca tctctatccg ctatgttc    28

-continued

```
<210> SEQ ID NO 139
<211> LENGTH: 78
<212> TYPE: DNA
<213> ORGANISM: Artificial Sequence
<220> FEATURE:
<223> OTHER INFORMATION: PST783 primer
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 139
aagaacatag cggatagaga tgcgcctcca nnknnknnkn nknnknnkga cgtgtaataa      60
gcatcaaagg aactactt                                                   78

<210> SEQ ID NO 140
<211> LENGTH: 28
<212> TYPE: DNA
<213> ORGANISM: Artificial Sequence
<220> FEATURE:
<223> OTHER INFORMATION: PST784 primer

<400> SEQUENCE: 140
gagagtatca gtctgagaac ctcctccc                                        28

<210> SEQ ID NO 141
<211> LENGTH: 82
<212> TYPE: DNA
<213> ORGANISM: Artificial Sequence
<220> FEATURE:
<223> OTHER INFORMATION: PST785 primer
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
```

<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 141
gggaggaggt tctcagactg atactctcnn knnknnknnk nnknnknnka acatatggat    60
taagaccaga acaactatt gg    82

<210> SEQ ID NO 142
<211> LENGTH: 32
<212> TYPE: DNA
<213> ORGANISM: Artificial Sequence
<220> FEATURE:
<223> OTHER INFORMATION: PST786 primer

<400> SEQUENCE: 142
agttcggaag aagttccaat agttgtttct gg    32

<210> SEQ ID NO 143
<211> LENGTH: 66
<212> TYPE: DNA
<213> ORGANISM: Artificial Sequence
<220> FEATURE:
<223> OTHER INFORMATION: PST787 primer
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 143
ccagaaacaa ctattggaac ttcttccgaa ctnnknnknn kggtatctac ttcctttcag    60
ccgagg    66

<210> SEQ ID NO 144
<211> LENGTH: 25
<212> TYPE: DNA
<213> ORGANISM: Artificial Sequence
<220> FEATURE:
<223> OTHER INFORMATION: PST788 primer

<400> SEQUENCE: 144
gtgtatctgg aattttagcc aaccg    25

<210> SEQ ID NO 145
<211> LENGTH: 62
<212> TYPE: DNA
<213> ORGANISM: Artificial Sequence
<220> FEATURE:
<223> OTHER INFORMATION: PST789 primer
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 145
cggttggcta aaattccaga tacacnnknn knnkagggta tttaagaaca tagcggatag    60
ag                                                                  62

<210> SEQ ID NO 146
<211> LENGTH: 26
<212> TYPE: DNA
<213> ORGANISM: Artificial Sequence
<220> FEATURE:
<223> OTHER INFORMATION: PST792 primer

<400> SEQUENCE: 146
agtatcgttt aggtaagcat caagcc                                        26

<210> SEQ ID NO 147
<211> LENGTH: 73
<212> TYPE: DNA
<213> ORGANISM: Artificial Sequence
<220> FEATURE:
<223> OTHER INFORMATION: PST793 primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 147
ggcttgatgc ttacctaaac gatactnnkn nknnknnknn knnknnktgg actcaagtat    60
gggctgctgc tag                                                      73

<210> SEQ ID NO 148
<211> LENGTH: 65
<212> TYPE: DNA
<213> ORGANISM: Artificial Sequence
<220> FEATURE:
<223> OTHER INFORMATION: PST801 primer
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:

```
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 148
gacaatggcc tggactcaag tatgggctnn knnknnknnk ggttctcaga ctgatactct    60
cccac                                                               65

<210> SEQ ID NO 149
<211> LENGTH: 71
<212> TYPE: DNA
<213> ORGANISM: Artificial Sequence
<220> FEATURE:
<223> OTHER INFORMATION: PST804 primer
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 149
gggtatttaa aacatagcg gatagannkn nknnknnknn knnknnkaca gcaatagccg    60
tagaggacgt g                                                       71

<210> SEQ ID NO 150
<211> LENGTH: 4475
<212> TYPE: DNA
<213> ORGANISM: Artificial Sequence
<220> FEATURE:
<223> OTHER INFORMATION: pSLM22

<400> SEQUENCE: 150
tcagaagaac tcgtcaagaa ggcgatagaa ggcgatgcgc tgcgaatcgg gagcggcgat    60
accgtaaagc acgaggaagc ggtcagccca ttcgccgcca agctcttcag caatatcacg   120
ggtagccaac gctatgtcct gatagcggtc cgccacaccc agccggccac agtcgatgaa   180
tccagaaaag cggccatttt ccaccatgat attcggcaag caggcatcgc catgggtcac   240
gacgagatcc tcgccgtcgg gcatgcgcgc cttgagcctg gcgaacagtt cggctggcgc   300
gagcccctga tgctcttcgt ccagatcatc ctgatcgaca agaccggctt ccatccgagt   360
acgtgctcgc tcgatgcgat gtttcgcttg gtggtcgaat gggcaggtag ccggatcaag   420
```

```
cgtatgcagc cgccgcattg catcagccat gatggatact ttctcggcag gagcaaggtg    480
agatgacagg agatcctgcc ccggcacttc gcccaatagc agccagtccc ttcccgcttc    540
agtgacaacg tcgagcacag ctgcgcaagg aacgcccgtc gtggccagcc acgatagccg    600
cgctgcctcg tcctgcagtt cattcagggc accggacagg tcggtcttga caaaaagaac    660
cgggcgcccc tgcgctgaca gccggaacac ggcggcatca gagcagccga ttgtctgttg    720
tgcccagtca tagccgaata gcctctccac ccaagcggcc ggagaacctg cgtgcaatcc    780
atcttgttca atcatgcgaa acgatcctca tcctgtctct tgatcagatc ttgatcccct    840
gcgccatcag atccttggcg gcaagaaagc catccagttt actttgcagg gcttcccaac    900
cttaccagag ggcgcccag ctggcaattc cgacgtctaa gaaaccatta ttatcatgac    960
attaacctat aaaaataggc gtatcacgag gccctttcgt cttcacctcg agtccctatc   1020
agtgatagag attgacatcc ctatcagtga tagagatact gagcacatca gcaggacgca   1080
ctgaccttaa ttaaatgcgc acccttagcg agaggtttat cattaaggtc aacctctgga   1140
tgttgtttcg gcatcctgca ttgaatctga gttactgtct gttttcctga attctagcca   1200
ctgatggtaa tattcaaggt actaagtggg gaggtaagtg gcttgatgct tacctacgtg   1260
acagcttcgt tgcgaagtcc aaggcgtgga ctcaggtgtg gtctggtagt gctggcggtg   1320
gggtaagtgt gactgtttca caggatctcc gcttccgcaa tatctggatt aagtgtgcca   1380
acaactcttg gaacttcttc cgtactggcc ccgatggaat ctacttcata gcctctgatg   1440
gtggatggtt acgattccaa atacactcca acggtctcgg attcaagaat attgcagaca   1500
gtcgttcagt acctaatgca atcatggtgg agaacgagta ataagcatca aaggaactac   1560
tttaagtcca cggatggact atcacactga attcaggaaa cccgtttttt ctgacgtaag   1620
ggtgcgcaac tttcatgaaa tccgctgaat atttgaacac ttttagattg agaaatctcg   1680
gcctacctgt catgaacaat ttgcatgaca tgtctaaggc gactcgcata tctgttgaaa   1740
cacttcggtt gttaatctat acagctgatt ttcgctatag gatctacact gtagaaaaga   1800
aaggcccaga agagaatg agaaccattt accaaccttc tcgagaactt aaagccttac   1860
aaggatgggt tctacgtaac attttagata aactgtcgtc atctcctttt tctattggat   1920
ttgaaaagca ccaatctatt tgaataatg ctaccccgca tattgggca aactttatac   1980 tgaatattga tttggaggat tttttcccaa gtttaactgc taacaaagtt tttggagtgt   2040
tccattctct tggttataat cgactaatat cttcagtttt gacaaaaata tgttgttata   2100
aaaatctgct accacaaggt gctccatcat cacctaaatt agctaatcta atatgttcta   2160
aacttgatta tcgtattcag ggttatgcag gtagtcgggg cttgatatat acgagatatg   2220
ccgatgatct caccttatct gcacagtcta tgaaaaaggt tgttaaagca cgtgattttt   2280 tatttctat aatcccaagt gaaggattgg ttattaactc aaaaaaaact tgtattagtg   2340
ggcctcgtag tcagaggaaa gttacaggtt tagttatttc acaagagaaa gttgggatag   2400
gtagagaaaa atataaagaa attagagcaa agatacatca tatattttgc ggtaagtctt   2460
ctgagataga acacgttagg ggatggttgt catttatttt aagtgtggat tcaaaaagcc   2520
ataggagatt aataacttat attagcaaat tagaaaaaaa atatggaaag aaccctttaa   2580
ataaagcgaa gacctaagga tccggttgat attattcaga ggtataaaac gaatgagtac   2640
tgcactcgca acgctggctg ggaagctggc tgaacgtgtc ggcatggatt ctgtcgaccc   2700
acaggaactg atcaccactc ttcgccagac ggcatttaaa ggtgatgcca gcgatgcgca   2760
```

| | | |
|---|---|---|
| gttcatcgca ttactgatcg ttgccaacca gtacggcctt aatccgtgga cgaaagaaat | 2820 | |
| ttacgccttt cctgataagc agaatggcat cgttccggtg gtgggcgttg atggctggtc | 2880 | |
| ccgcatcatc aatgaaaacc agcagtttga tggcatggac tttgagcagg acaatgaatc | 2940 | |
| ctgtacatgc cggatttacc gcaaggaccg taatcatccg atctgcgtta ccgaatggat | 3000 | |
| ggatgaatgc cgccgcgaac cattcaaaac tcgcgaaggc agagaaatca cggggccgtg | 3060 | |
| gcagtcgcat cccaaacgga tgttacgtca taaagccatg attcagtgtg cccgtctggc | 3120 | |
| cttcggattt gctggtatct atgacaagga tgaagccgag cgcattgtcg aaaatactgc | 3180 | |
| atacactgca gaacgtcagc cggaacgcga catcactccg gttaacgatg aaaccatgca | 3240 | |
| ggagattaac actctgctga tcgccctgga taaaacatgg gatgacgact tattgccgct | 3300 | |
| ctgttcccag atatttcgcc gcgacattcg tgcatcgtca gaactgacac aggccgaagc | 3360 | |
| agtaaaagct cttggattcc tgaaacagaa agccgcagag cagaaggtgg cagcatgaac | 3420 | |
| gcgtgctaga ggcatcaaat aaaacgaaag gctcagtcga agactgggc ctttcgtttt | 3480 | |
| atctgttgtt tgtcggtgaa cgctctcctg agtaggacaa atccgccgcc ctagacctag | 3540 | |
| gggatatatt ccgcttcctc gctcactgac tcgctacgct cggtcgttcg actgcggcga | 3600 | |
| gcggaaatgg cttacgaacg gggcggagat ttcctggaag atgccaggaa gatacttaac | 3660 | |
| agggaagtga gagggccgcg gcaaagccgt ttttccatag gctccgcccc cctgacaagc | 3720 | |
| atcacgaaat ctgacgctca aatcagtggt ggcgaaaccc gacaggacta taaagatacc | 3780 | |
| aggcgtttcc ccctggcggc tccctcgtgc gctctcctgt tcctgccttt cggtttaccg | 3840 | |
| gtgtcattcc gctgttatgg ccgcgtttgt ctcattccac gcctgacact cagttccggg | 3900 | |
| taggcagttc gctccaagct ggactgtatg cacgaacccc ccgttcagtc cgaccgctgc | 3960 | |
| gccttatccg gtaactatcg tcttgagtcc aacccggaaa gacatgcaaa agcaccactg | 4020 | |
| gcagcagcca ctggtaattg atttagagga gttagtcttg aagtcatgcg ccggttaagg | 4080 | |
| ctaaactgaa aggacaagtt ttggtgactg cgctcctcca agccagttac ctcggttcaa | 4140 | |
| agagttggta gctcagagaa ccttcgaaaa accgccctgc aaggcggttt tttcgttttc | 4200 | |
| agagcaagag attacgcgca gaccaaaacg atctcaagaa gatcatctta ttaatcagat | 4260 | |
| aaaatatttc tagatttcag tgcaatttat ctcttcaaat gtagcacctg aagtcagccc | 4320 | |
| catacgatat aagttgttac tagtgcttgg attctcacca ataaaaaacg cccggcgga | 4380 | |
| accgagcgtt ctgaacaaat ccagatggag ttctgaggtc attactggat ctatcaacag | 4440 | |
| gagtccaagc gagctctcga accccagagt cccgc | 4475 | |

<210> SEQ ID NO 151
<211> LENGTH: 4172
<212> TYPE: DNA
<213> ORGANISM: Artificial Sequence
<220> FEATURE:
<223> OTHER INFORMATION: pSLM49

<400> SEQUENCE: 151

| | | |
|---|---|---|
| atgattgaac aagatggatt gcacgcaggt tctccggccg cttgggtgga gaggctattc | 60 | |
| ggctatgact gggcacaaca gacaatcggc tgctctgatg ccgccgtgtt ccggctgtca | 120 | |
| gcgcaggggc gcccggttct ttttgtcaag accgacctgt ccggtgccct gaatgaactg | 180 | |
| caggacgagg cagcgcggct atcgtggctg gccacgacgg gcgttccttg cgcagctgtg | 240 | |
| ctcgacgttg tcactgaagc gggaagggac tggctgctat tgggcgaagt gccggggcag | 300 | |
| gatctcctgt catctcacct tgctcctgcc gagaaagtat ccatcatggc tgatgcaatg | 360 | |

-continued

```
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctaccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctgagcggg actctggggt tcgagagctc gcttggactc ctgttgatag    840
atccagtaat gacctcagaa ctccatctgg atttgttcag aacgtcggt tgccgccggg    900 cgttttttat tggtgagaat ccaagcacta gtaacaactt atatcgtatg ggctgactt    960 caggtgctac atttgaagag ataaattgca ctgaaatcta gaatattt atctgattaa    1020 taagatgatc ttcttgagat cgttttggtc tgcgcgtaat ctcttgctct gaaaacgaaa    1080
aaaccgcctt gcagggcggt ttttcgaagg ttctctgagc taccaactct ttgaaccgag    1140
gtaactggct tggaggagcg cagtcaccaa aacttgtcct ttcagtttag ccttaaccgg    1200
cgcatgactt caagactaac tcctctaaat caattaccag tggctgctgc cagtggtgct    1260
tttgcatgtc tttccgggtt ggactcaaga cgatagttac cggataaggc gcagcggtcg    1320
gactgaacgg ggggttcgtg catacagtcc agcttggagc gaactgccta cccggaactg    1380
agtgtcaggc gtggaatgag acaaacgcgg ccataacagc ggaatgacac cggtaaaccg    1440
aaaggcagga acaggagagc gcacgaggga ccgccaggg ggaaacgcct ggtatcttta    1500
tagtcctgtc gggtttcgcc accactgatt tgagcgtcag atttcgtgat gcttgtcagg    1560
ggggcggagc ctatggaaaa acggctttgc cgcggccctc tcacttccct gttaagtatc    1620
ttcctggcat cttccaggaa atctccgccc cgttcgtaag ccatttccgc tcgccgcagt    1680
cgaacgaccg agcgtagcga gtcagtgagc gaggaagcgg aatatatccc ctaggtctgg    1740
atcctgaagg aacgtgaccc aaacaaaccg tacacctcta gagaggtaat gggagctatg    1800
ggttcgaacc ttctggagca gatgccttcc gctggctttg tggctaacgt aggggctacc    1860
ttaatgaatg ctgctggtgt ggttaactca cctaacaaag caaccgagca ggacttcatg    1920
actggattga tgaactctac caaagagtta gtgcctaacg accctcttac tcaacagctt    1980
gtggttaaga tttatgaggc gaacggtgtt aacctgaggg agcgtaagaa ataatacgac    2040
tcactatagg gagaggcgaa ataatcttct ccctgtagtc tcttagattt actttaagga    2100
ggtcaaatgg ctaacgtaat taaaaccgtt ttgacttacc agttagatgg ctccaatcgt    2160 gatttaata tcccgtttga gtatctagcc cgtaagttcg tagtagtaac ccttattggc    2220
gtagaccgca aggtccttac gattaatgca gactaccgtt ttgctacgcg tactaccatc    2280
tcacttacca aggcttgggg tccagcggat ggatacacta ccatcgagtt acgccgagta    2340
acctccacaa ccgaccgatt ggttgacttt acggatggtt caatcctccg tgcgtatgac    2400
cttaacgtcg ctcagattca aacgatgcac gtagcggaag aggcccgtga cctcactgct    2460
gataccatag gtgtcaataa tgatggtcat ttggatgctc gtggtcgtcg aattgttaac    2520
ctagcgaacg ctgtggatga ccgcgacgct gttccgtttg gtcaacttaa gaccatgaac    2580
cagaactcgt ggcaggcgcg taatgaggca ctacagttcc gtaatgaggc tgagactttc    2640
agaaatcaaa cggaggtttt taagaatgag tccggtacta acgctacgaa cacaaagcag    2700
```

```
tggcgagatg aggctaatgg gtcccgagat gaagccgagc agttcaagaa tacggctggt    2760
caatacgcta catctgctgg gaactctgct actgctgcgc atcaatctga ggtaaacgct    2820
gagaactccg ctacagcagc agcgaactct gcgaatttgg cagaacaaca cgcagaccgt    2880
gcggaacgtg aagcagacaa gctggggaat tttaatggac tggctggtgc aattgacagg    2940
gtggatggaa ccaatgtgta ctggaaagga ggtatccatg cgaacggacg cctttacctt    3000
acctcagatg gtttcgactg tggtcagtat caacagttct ttggtggttc tgctggtcgt    3060
tactctgtca tggagtgggg tgatgagaac ggatggctga tgcatgttca acgtagagag    3120
tggacaacag cgataggtga taacatccag ctagtagtaa acggacatat catcgcccaa    3180
ggtggagaca tgactggtcc gctgaaattg cagaatggac atgcccttta cttagagtcc    3240
gcatccgaca aggcgcaata tattctatct aaagatggta acagaaacaa ctggtacatt    3300
ggtagaggat cagataacaa caatgactgt accttccact cctatgtgta tggtacgaac    3360
ttaacactca agccggacta tgcagtagtt aacaaacgct tccacgtagg tcaggcagtt    3420
gtagccactg atggtaatat tcaaggtact aagtggggag gtaagtggct tgatgcttac    3480
ctaaacgata cttacgttaa gaagacaatg gcctggactc aagtatgggc tgctgctagt    3540
ggtagttaca tgggaggagg ttctcagact gatactctcc cacaggactt gcgattccgc    3600
aacatatgga ttaagaccag aaacaactat tggaacttct tccgaactgg tcctgacggt    3660
atctacttcc tttcagccga gggcggttgg ctaaaattcc agatacactc taatggcagg    3720
gtatttaaga acatagcgga tagagatgcg cctccaacag caatagccgt agaggacgtg    3780
taataagcat caaaggaact actttaagtc cacggatgga ctatcacact aaggaggaca    3840
catgttgtca ttggattta acaacgaact aattaaagcg gcaccgattg taggtacagg    3900
tgttgcagat gttagtgcaa gactgttctt cgggctaagc ctgaatgaat ggttctatgt    3960
ggctgctatc gcctacacag tggttcagat tggtgccaag gtagtcgata agatcccggg    4020
tgcaaagctt gacgtcggaa ttgccagctg gggcgccctc tggtaaggtt gggaagcctt    4080
gcaaagtaaa ctggatggct ttcttgccgc caaggatctg atggcgcagg ggatcaagat    4140
ctgatcaaga gacaggatga ggatcgtttc gc                                 4172
```

<210> SEQ ID NO 152
<211> LENGTH: 553
<212> TYPE: PRT
<213> ORGANISM: Artificial Sequence
<220> FEATURE:
<223> OTHER INFORMATION: Synthetic Polypeptide

<400> SEQUENCE: 152

Met Ala Asn Val Ile Lys Thr Val Leu Thr Tyr Gln Leu Asp Gly Ser
1               5                   10                  15

Asn Arg Asp Phe Asn Ile Pro Phe Glu Tyr Leu Ala Arg Lys Phe Val
                20                  25                  30

Val Val Thr Leu Ile Gly Val Asp Arg Lys Val Leu Thr Ile Asn Thr
            35                  40                  45

Asp Tyr Arg Phe Ala Thr Arg Thr Thr Ile Ser Leu Thr Lys Ala Trp
        50                  55                  60

Gly Pro Ala Asp Gly Tyr Thr Thr Ile Glu Leu Arg Arg Val Thr Ser
65                  70                  75                  80

Thr Thr Asp Arg Leu Val Asp Phe Thr Asp Gly Ser Ile Leu Arg Ala
                85                  90                  95

Tyr Asp Leu Asn Val Ala Gln Ile Gln Thr Met His Val Ala Glu Glu

-continued

Ala Arg Asp Leu Thr Thr Asp Thr Ile Gly Val Asn Asn Asp Gly His
100                 105                 110                 115

Leu Asp Ala Arg Gly Arg Ile Val Asn Leu Ala Asn Ala Val Asp
    120                 125                 130

Asp Arg Asp Ala Val Pro Phe Gly Gln Leu Lys Thr Met Asn Gln Asn
145                 150                 155                 160

Ser Trp Gln Ala Arg Asn Glu Ala Leu Gln Phe Arg Asn Glu Ala Glu
                165                 170                 175

Thr Phe Arg Asn Gln Ala Glu Gly Phe Lys Asn Glu Ser Ser Thr Asn
                180                 185                 190

Ala Thr Asn Thr Lys Gln Trp Arg Asp Glu Thr Lys Gly Phe Arg Asp
            195                 200                 205

Glu Ala Lys Arg Phe Lys Asn Thr Ala Gly Gln Tyr Ala Thr Ser Ala
            210                 215                 220

Gly Asn Ser Ala Ser Ala Ala His Gln Ser Glu Val Asn Ala Glu Asn
225                 230                 235                 240

Ser Ala Thr Ala Ser Ala Asn Ser Ala His Leu Ala Glu Gln Gln Ala
                245                 250                 255

Asp Arg Ala Glu Arg Glu Ala Asp Lys Leu Glu Asn Tyr Asn Gly Leu
                260                 265                 270

Ala Gly Ala Ile Asp Lys Val Asp Gly Thr Asn Val Tyr Trp Lys Gly
            275                 280                 285

Asn Ile His Ala Asn Gly Arg Leu Tyr Met Thr Thr Asn Gly Phe Asp
    290                 295                 300

Cys Gly Gln Tyr Gln Gln Phe Phe Gly Gly Val Thr Asn Arg Tyr Ser
305                 310                 315                 320

Val Met Glu Trp Gly Asp Glu Asn Gly Trp Leu Met Tyr Val Gln Arg
                325                 330                 335

Arg Glu Gln Thr Thr Ala Ile Gly Gly Asn Ile Gln Leu Val Val Asn
                340                 345                 350

Gly Gln Ile Ile Thr Gln Gly Gly Ala Met Thr Gly Gln Leu Lys Leu
            355                 360                 365

Gln Asn Gly His Val Leu Gln Leu Glu Ser Ala Ser Asp Lys Ala His
            370                 375                 380

Tyr Ile Leu Ser Lys Asp Gly Asn Arg Asn Asn Trp Tyr Ile Gly Arg
385                 390                 395                 400

Gly Ser Asp Asn Asn Asn Asp Cys Thr Phe His Ser Tyr Val His Gly
                405                 410                 415

Thr Thr Leu Thr Leu Lys Gln Asp Tyr Ala Val Val Asn Lys His Phe
                420                 425                 430

His Val Gly Gln Ala Val Val Ala Thr Asp Gly Asn Ile Gln Gly Thr
            435                 440                 445

Lys Trp Gly Gly Lys Trp Leu Asp Ala Tyr Leu Arg Asp Ser Phe Val
            450                 455                 460

Ala Lys Ser Lys Ala Trp Thr Gln Val Trp Ser Gly Ser Ala Gly Gly
465                 470                 475                 480

Gly Val Ser Val Thr Val Ser Gln Asp Leu Arg Phe Arg Asn Ile Trp
                485                 490                 495

Ile Lys Cys Ala Asn Asn Ser Trp Asn Phe Phe Arg Thr Gly Pro Asp
                500                 505                 510

Gly Ile Tyr Phe Ile Ala Ser Asp Gly Gly Trp Leu Arg Phe Gln Ile
            515                 520                 525

His Ser Asn Gly Leu Gly Phe Lys Asn Ile Ala Asp Ser Arg Ser Val
    530                 535                 540

Pro Asn Ala Ile Met Val Glu Asn Glu
545                 550

<210> SEQ ID NO 153
<211> LENGTH: 558
<212> TYPE: PRT
<213> ORGANISM: Artificial Sequence
<220> FEATURE:
<223> OTHER INFORMATION: Synthetic Polypeptide

<400> SEQUENCE: 153

Met Ala Asn Val Ile Lys Thr Val Leu Thr Tyr Gln Leu Asp Gly Ser
1               5                   10                  15

Asn Arg Asp Phe Asn Ile Pro Phe Glu Tyr Leu Ala Arg Lys Phe Val
            20                  25                  30

Val Val Thr Leu Ile Gly Val Asp Arg Lys Val Leu Thr Ile Asn Ala
        35                  40                  45

Asp Tyr Arg Phe Ala Thr Arg Thr Thr Ile Ser Leu Thr Lys Ala Trp
    50                  55                  60

Gly Pro Ala Asp Gly Tyr Thr Thr Ile Glu Leu Arg Arg Val Thr Ser
65                  70                  75                  80

Thr Thr Asp Arg Leu Val Asp Phe Thr Asp Gly Ser Ile Leu Arg Ala
                85                  90                  95

Tyr Asp Leu Asn Val Ala Gln Ile Gln Thr Met His Val Ala Glu Glu
            100                 105                 110

Ala Arg Asp Leu Thr Ala Asp Thr Ile Gly Val Asn Asn Asp Gly His
        115                 120                 125

Leu Asp Ala Arg Gly Arg Ile Val Asn Leu Ala Asn Ala Val Asp
    130                 135                 140

Asp Arg Asp Ala Val Pro Phe Gly Gln Leu Lys Thr Met Asn Gln Asn
145                 150                 155                 160

Ser Trp Gln Ala Arg Asn Glu Ala Leu Gln Phe Arg Asn Glu Ala Glu
                165                 170                 175

Thr Phe Arg Asn Gln Thr Glu Val Phe Lys Asn Glu Ser Gly Thr Asn
            180                 185                 190

Ala Thr Asn Thr Lys Gln Trp Arg Asp Glu Ala Asn Gly Ser Arg Asp
        195                 200                 205

Glu Ala Glu Gln Phe Lys Asn Thr Ala Gly Gln Tyr Ala Thr Ser Ala
    210                 215                 220

Gly Asn Ser Ala Thr Ala Ala His Gln Ser Glu Val Asn Ala Glu Asn
225                 230                 235                 240

Ser Ala Thr Ala Ala Asn Ser Ala Asn Leu Ala Glu Gln His Ala
                245                 250                 255

Asp Arg Ala Glu Arg Glu Ala Asp Lys Leu Gly Asn Phe Asn Gly Leu
            260                 265                 270

Ala Gly Ala Ile Asp Arg Val Asp Gly Thr Asn Val Tyr Trp Lys Gly
        275                 280                 285

Gly Ile His Ala Asn Gly Arg Leu Tyr Leu Thr Ser Asp Gly Phe Asp
    290                 295                 300

Cys Gly Gln Tyr Gln Gln Phe Phe Gly Gly Ser Ala Gly Arg Tyr Ser
305                 310                 315                 320

Val Met Glu Trp Gly Asp Glu Asn Gly Trp Leu Met His Val Gln Arg
                325                 330                 335

```
Arg Glu Gln Thr Thr Ala Ile Gly Asp Asn Ile Gln Leu Val Val Asn
                340                 345                 350

Gly His Ile Ile Ala Gln Gly Gly Asp Met Thr Gly Pro Leu Lys Leu
            355                 360                 365

Gln Asn Gly His Ala Leu Tyr Leu Glu Ser Ala Ser Asp Lys Ala Gln
        370                 375                 380

Tyr Ile Leu Ser Lys Asp Gly Asn Arg Asn Asn Trp Tyr Ile Gly Arg
385                 390                 395                 400

Gly Ser Asp Asn Asn Asn Asp Cys Thr Phe His Ser Tyr Val Tyr Gly
                405                 410                 415

Thr Asn Leu Thr Leu Lys Pro Asp Tyr Ala Val Val Asn Lys Arg Phe
            420                 425                 430

His Val Gly Gln Ala Val Val Ala Thr Asp Gly Asn Ile Gln Gly Thr
        435                 440                 445

Lys Trp Gly Gly Lys Trp Leu Asp Ala Tyr Leu Asn Asp Thr Tyr Val
            450                 455                 460

Lys Lys Thr Met Ala Trp Thr Gln Val Trp Ala Ala Ser Gly Ser
465                 470                 475                 480

Tyr Met Gly Gly Gly Ser Gln Thr Asp Thr Leu Pro Gln Asp Leu Arg
                485                 490                 495

Phe Arg Asn Ile Trp Ile Lys Thr Arg Asn Asn Tyr Trp Asn Phe Phe
            500                 505                 510

Arg Thr Gly Pro Asp Gly Ile Tyr Phe Leu Ser Ala Glu Gly Gly Trp
        515                 520                 525

Leu Lys Phe Gln Ile His Ser Asn Gly Arg Val Phe Lys Asn Ile Ala
            530                 535                 540

Asp Arg Asp Ala Pro Pro Thr Ala Ile Ala Val Glu Asp Val
545                 550                 555

<210> SEQ ID NO 154
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 154

His Gly Leu Ser Leu
1               5

<210> SEQ ID NO 155
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 155

Leu Gly Leu Ala Val
1               5

<210> SEQ ID NO 156
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 156
```

Asn Cys His Val
1

<210> SEQ ID NO 157
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 157

His Thr Gly Ile
1

<210> SEQ ID NO 158
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 158

Ala Tyr Ala Ser Pro
1               5

<210> SEQ ID NO 159
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 159

Lys Ser Gly Val
1

<210> SEQ ID NO 160
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 160

Lys Ala Gly Ile
1

<210> SEQ ID NO 161
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 161

His Ser Val Val
1

<210> SEQ ID NO 162
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 162

Lys Ala Gly Pro

```
<210> SEQ ID NO 163
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 163

His Thr His Pro
1

<210> SEQ ID NO 164
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 164

Gly Ala Arg Val
1

<210> SEQ ID NO 165
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 165

Ala Ser Arg Val
1

<210> SEQ ID NO 166
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 166

Arg Thr Phe Ile
1

<210> SEQ ID NO 167
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 167

Lys Leu Asn Ile
1

<210> SEQ ID NO 168
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 168

Arg Phe Val Val
1
```

<210> SEQ ID NO 169
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 169

Arg Asp Ile Arg Leu Ser Ile
1               5

<210> SEQ ID NO 170
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 170

Leu Asp Ala Tyr Leu Asn Asp Thr Tyr Val Lys Lys Thr Met Ala Trp
1               5                   10                  15

Thr Gln Val Trp Ala Ala Ala Ser Gly Ser Tyr Met Gly Gly Gly Ser
            20                  25                  30

Gln Thr Asp Thr Leu Pro Gln Asp Leu Arg Phe Arg Asn Ile Trp Ile
        35                  40                  45

Lys Thr Arg Asn Asn Tyr Trp Asn Phe Phe Arg Thr Gly Pro Asp Gly
    50                  55                  60

Ile Tyr Phe Leu Ser Ala Glu Gly Gly Trp Leu Lys Phe Gln Ile His
65                  70                  75                  80

Ser Asn Gly Arg Val Phe Lys Asn Ile Ala Asp Arg Asp Ala Pro Pro
                85                  90                  95

Thr Ala Ile Ala Val Glu Asp Val
            100

<210> SEQ ID NO 171
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 171

Leu Asp Ala Tyr Leu Asn Asp Thr Tyr Val Lys Lys Thr Lys Ala Trp
1               5                   10                  15

Thr Gln Val Trp Ala Ala Ala Gly Gly Ser Tyr Met Gly Gly Gly Ser
            20                  25                  30

Gln Thr Asp Thr Leu Pro Gln Asp Leu Arg Phe Arg Asn Ile Trp Ile
        35                  40                  45

Lys Thr Arg Asn Asn Tyr Trp Asn Phe Phe Arg Thr Gly Pro Asp Gly
    50                  55                  60

Ile Tyr Phe Leu Leu Ala Glu Gly Gly Trp Leu Lys Phe Gln Ile His
65                  70                  75                  80

Ser Asn Gly Arg Val Phe Lys Asn Ile Ser Asp Arg Asp Ala Pro Pro
                85                  90                  95

Thr Ala Ile Ala Val Glu Asp Val
            100

<210> SEQ ID NO 172
<211> LENGTH: 104

```
<212> TYPE: PRT
<213> ORGANISM: Artificial Sequence
<220> FEATURE:
<223> OTHER INFORMATION: Synthetic Polypeptide

<400> SEQUENCE: 172

Leu Asp Ala Tyr Leu Asn Asp Thr Tyr Val Lys Lys Thr Met Ala Trp
1               5                   10                  15

Thr Gln Val Trp Ala Ala Ala Gly Gly Ser Tyr Met Gly Gly Gly Ser
            20                  25                  30

Gln Thr Asp Thr Leu Pro Gln Asp Leu Arg Phe Arg Asn Ile Trp Ile
        35                  40                  45

Lys Thr Arg Asn Asn Tyr Trp Asn Phe Phe Arg Thr Gly Pro Asp Gly
    50                  55                  60

Ile Tyr Phe Leu Leu Ala Glu Gly Gly Trp Leu Lys Phe Gln Ile His
65                  70                  75                  80

Ser Asn Gly Arg Val Phe Lys Asn Ile Ser Asp Arg Asp Ala Pro Pro
                85                  90                  95

Thr Ala Ile Ala Val Glu Asp Val
            100

<210> SEQ ID NO 173
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 173

Leu Asp Ala Tyr Leu Asn Asp Thr Tyr Val Lys Lys Thr Met Ala Trp
1               5                   10                  15

Thr Gln Val Trp Ala Ala Ala Ser Gly Ser Tyr Met Gly Gly Gly Ser
            20                  25                  30

Gln Thr Asp Thr Leu Pro Gln Asp Leu Arg Phe Arg Asn Ile Trp Ile
        35                  40                  45

Lys Thr Arg Asn Asn Tyr Trp Asn Phe Phe Arg Thr Gly Pro Asp Gly
    50                  55                  60

Ile Tyr Tyr Leu Ser Ala Glu Gly Gly Trp Leu Lys Phe Gln Ile His
65                  70                  75                  80

Ser Asn Gly Arg Val Phe Lys Asn Ile Ala Asp Arg Asp Ala Pro Pro
                85                  90                  95

Thr Ala Ile Ala Val Glu Asp Val
            100

<210> SEQ ID NO 174
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 174

Leu Asp Ala Tyr Leu Asn Asp Thr Tyr Val Lys Lys Thr Met Ala Trp
1               5                   10                  15

Thr Gln Val Trp Ala Ala Ala Ser Gly Ser Tyr Met Arg Gly Gly Ser
            20                  25                  30

Gln Thr Asp Thr Leu Pro Gln Asp Leu Arg Phe Arg Asn Ile Trp Ile
        35                  40                  45

Lys Thr Arg Asn Asn Ser Trp Ser Phe Phe Arg Thr Gly Pro Asp Gly
```

```
                 50                  55                  60

Ile Tyr Phe Leu Ser Ala Glu Gly Gly Trp Leu Lys Phe Gln Ile His
 65                  70                  75                  80

Ser Asn Gly Arg Val Phe Lys Asn Ile Ala Asp Ser Tyr Ala Pro Pro
                 85                  90                  95

Ile Ala Ile Ala Val Glu Asp Val
                100

<210> SEQ ID NO 175
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 175

Leu Asp Val Tyr Leu Asn Asp Thr Tyr Val Lys Lys Thr Met Ala Trp
  1               5                  10                  15

Thr Gln Val Trp Ala Ala Asp Ser Gly Lys Tyr Leu Pro Gly Gly Ser
                 20                  25                  30

Gln Thr Asp Thr Leu Pro Gln Asp Leu Arg Phe Arg Asn Ile Trp Ile
                 35                  40                  45

Arg Thr Arg Asn Asn Tyr Trp Asn Phe Phe Arg Thr Gly Pro Asp Gly
 50                  55                  60

Ile Tyr Phe Leu Ser Ala Glu Gly Gly Trp Leu Lys Phe Gln Ile His
 65                  70                  75                  80

Ser Asn Gly Arg Val Phe Lys Asn Ile Ser Asp Arg Asp Ala Pro Pro
                 85                  90                  95

Thr Ala Ile Ala Val Glu Asp Val
                100

<210> SEQ ID NO 176
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 176

Leu Asp Ala Tyr Leu Asn Asp Thr Tyr Val Lys Lys Thr Met Ala Trp
  1               5                  10                  15

Thr Gln Val Trp Ala Ala Ser Gly Ser Tyr Met Arg Gly Gly Ser
                 20                  25                  30

Gln Thr Asp Thr Leu Pro Gln Asp Leu Arg Phe Arg Asn Ile Trp Ile
                 35                  40                  45

Lys Thr Arg Asn Asn Tyr Trp Asn Phe Phe Arg Thr Gly Pro Asp Gly
 50                  55                  60

Ile Tyr Phe Leu Ser Ala Glu Asp Gly Trp Leu Lys Phe Gln Ile His
 65                  70                  75                  80

Ser Asn Gly Arg Val Phe Lys Asn Ile Ala Asp Arg Tyr Ala Pro Pro
                 85                  90                  95

Thr Ala Ile Ala Val Glu Asp Val
                100

<210> SEQ ID NO 177
<211> LENGTH: 69
<212> TYPE: DNA
<213> ORGANISM: Artificial Sequence
<220> FEATURE:
```

```
<223> OTHER INFORMATION: Synthetic Polynucleotide
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t

<400> SEQUENCE: 177
ggcagggtat ttaagaacat agcggataga nnknnknnkn nkacagcaat agccgtagag    60
gacgtgtaa                                                           69

<210> SEQ ID NO 178
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 178
ggcagggtat ttaagaacat agcggataga gatgcgcctc cacagcaata gccgtagagg    60
acgtgtaa                                                            68

<210> SEQ ID NO 179
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 179
ccgtcccata aattcttgta tcgcctatct                                    30

<210> SEQ ID NO 180
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 180

Gly Arg Val Phe Lys Asn Ile Ala Asp Arg Asp Ala Pro Pro Thr Ala
1               5                   10                  15

Ile Ala Val Glu Asp Val
            20

<210> SEQ ID NO 181
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 181

Trp Thr Gln Val Trp Ser Gly Ser Ala Gly Gly Gly Val Ser Val Thr
1               5                   10                  15
```

Val Ser Gln Asp Leu Arg Phe Arg Asn Ile Trp Ile Lys Phe Asp Asp
            20                  25                  30

Asn Val Trp Asn Phe Phe Arg Thr Gly Pro Asp Gly Ile Tyr Phe Ile
            35                  40                  45

Arg Val Ser Lys Gly Trp Leu Arg Phe Gln Ile His Ser Asn Gly Leu
        50                  55                  60

Gly Phe Lys Asn Ile Ala Asp Ser Arg Ser Val Pro Asn Ala Ile Met
65                  70                  75                  80

Val Glu Asn Glu

<210> SEQ ID NO 182
<211> LENGTH: 84
<212> TYPE: PRT
<213> ORGANISM: Artificial Sequence
<220> FEATURE:
<223> OTHER INFORMATION: Synthetic Polypeptide

<400> SEQUENCE: 182

Trp Thr Gln Val Trp Ser Gly Ser Ala Gly Gly Gly Val Ser Val Thr
1               5                   10                  15

Val Ser Gln Asp Leu Arg Phe Arg Asn Ile Trp Ile Lys Cys Ala Asn
            20                  25                  30

Asn Ser Trp Asn Phe Phe Arg Thr Gly Pro Asp Gly Ile Tyr Phe Ile
            35                  40                  45

Ala Ser Asp Gly Gly Trp Leu Arg Phe Gln Ile His Ser Asn Gly Leu
        50                  55                  60

Gly Phe Lys Asn Ile Ala Asp Ser Arg Ser Val Pro Asn Ala Ile Met
65                  70                  75                  80

Val Glu Asn Glu

<210> SEQ ID NO 183
<211> LENGTH: 199
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (89)..(90)
<223> OTHER INFORMATION: n is a, c, g, or t
<220> FEATURE:
<221> NAME/KEY: misc_feature
<222> LOCATION: (92)..(93)
<223> OTHER INFORMATION: n is a, c, g, or t
<220> FEATURE:
<221> NAME/KEY: misc_feature
<222> LOCATION: (95)..(96)

<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (146)..(147)
<223> OTHER INFORMATION: n is a, c, g, or t
<220> FEATURE:
<221> NAME/KEY: misc_feature
<222> LOCATION: (149)..(150)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
<221> NAME/KEY: misc_feature
<222> LOCATION: (158)..(159)
<223> OTHER INFORMATION: n is a, c, g, or t

<400> SEQUENCE: 183
tgcaggtctc ttgtggtctn nknnknnknn knnkggggta agtgtgactg tttcacagga    60
tctccgcttc cgcaatatct ggattaagnn knnknnknnk nnktggaact tcttccgtac   120
tggccccgat ggaatctact tcatannknn knnknnknnk tggttacgat tccaaataca   180
ctccaacgag agacctgca                                                199

<210> SEQ ID NO 184
<211> LENGTH: 199
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (98)..(99)
<223> OTHER INFORMATION: n is a, c, g, or t
<220> FEATURE:
<221> NAME/KEY: misc_feature
<222> LOCATION: (101)..(102)
<223> OTHER INFORMATION: n is a, c, g, or t
<220> FEATURE:
<221> NAME/KEY: misc_feature
<222> LOCATION: (104)..(105)
<223> OTHER INFORMATION: n is a, c, g, or t

```
<220> FEATURE:
<221> NAME/KEY: misc_feature
<222> LOCATION: (107)..(108)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (167)..(168)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (173)..(174)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (179)..(180)
<223> OTHER INFORMATION: n is a, c, g, or t

<400> SEQUENCE: 184
tgcaggtctc tcgttggagt gtatttggaa tcgtaaccam nnmnmnnmn nmnntatgaa      60 gtagattcca tcggggccag tacggaagaa gttccamnnm nnmnmnnmn ncttaatcca    120 gatattgcgg aagcggagat cctgtgaaac agtcacactt acccmnnm nmnnmnnmn     180 agaccacaag agacctgca                                                199

<210> SEQ ID NO 185
<211> LENGTH: 104
<212> TYPE: PRT
<213> ORGANISM: Artificial Sequence
<220> FEATURE:
<223> OTHER INFORMATION: Synthetic Polypeptide

<400> SEQUENCE: 185

Leu Asp Ala Tyr Leu Asn Asp Thr Tyr Val Lys Lys Thr Met Ala Trp
1               5                   10                  15

Thr Gln Val Trp Ala Ala Ala Ser Gly Ser Tyr Met Gly Gly Gly Ser
                20                  25                  30

Gln Thr Asp Thr Leu Pro Gln Asp Leu Arg Phe Arg Asn Ile Trp Ile
            35                  40                  45

Lys Thr Arg Asn Asn Tyr Trp Asn Phe Phe Arg Thr Gly Pro Asp Gly
    50                  55                  60

Ile Tyr Phe Leu Ser Ala Glu Gly Gly Trp Leu Lys Phe Gln Ile His
65                  70                  75                  80

Ser Asn Gly Arg Val Phe Lys Asn Ile Ala Asp Arg Asp Ala Pro Pro
                85                  90                  95

Thr Ala Ile Ala Val Glu Asp Val
            100

<210> SEQ ID NO 186
<211> LENGTH: 99
<212> TYPE: PRT
<213> ORGANISM: Artificial Sequence
<220> FEATURE:
<223> OTHER INFORMATION: Synthetic Polypeptide

<400> SEQUENCE: 186
```

```
Leu Asp Ala Tyr Leu Arg Asp Ser Phe Val Ala Lys Ser Lys Ala Trp
1               5                   10                  15

Thr Gln Val Trp Ser Gly Ser Ala Gly Gly Val Ser Val Thr Val
            20              25              30

Ser Gln Asp Leu Arg Phe Arg Asn Ile Trp Ile Lys Cys Ala Asn Asn
        35              40              45

Ser Trp Asn Phe Phe Arg Thr Gly Pro Asp Gly Ile Tyr Phe Ile Ala
    50              55              60

Ser Asp Gly Gly Trp Leu Arg Phe Gln Ile His Ser Asn Gly Leu Gly
65              70              75              80

Phe Lys Asn Ile Ala Asp Ser Arg Ser Val Pro Asn Ala Ile Met Val
                85              90              95

Glu Asn Glu
```

SYNTHETIC BACTERIOPHAGES AND BACTERIOPHAGE COMPOSITIONS

RELATED APPLICATION

This application claims the benefit under 35 U.S.C. § 119(e) of U.S. Provisional Application Ser. No. 62/414,558, filed Oct. 28, 2016, the entire disclosure of which is incorporated by reference herein.

GOVERNMENT SUPPORT

This invention was made with Government support under Grant No. R21 AI121669 awarded by the National Institutes of Health, Grant No. HDTRA1-14-1-0007 awarded by the Defense Threat Reduction Agency, and Contract No. W911NF-13-D-0001 awarded by Army Research Office. The Government has certain rights in the invention.

FIELD

Disclosed herein are novel synthetic bacteriophages and bacteriophage compositions, methods of production thereof, and therapeutic uses thereof.

BACKGROUND

The rapid escalation of drug-resistant bacterial infections and decreased investment in antibiotic research make it imperative to develop alternative therapies. Engineering synthetic bacteriophages (or phages) with expanded host ranges is one approach which has, to this point, remained underdeveloped. Previous attempts to engineer phage host range utilized genome reconstruction in the yeast *Saccharomyces cerevisiae* (Ando et al. Cell Syst. 1, 187-196 (2015)). This method is limited in that it requires prior knowledge of the host range of the phages used for reconstruction. Alternatively, some studies have relied on traditional phage mutant selection procedures which utilizes natural evolution (Perry et al. PLoS One 10, e0130639 (2015); Qimron et al. Proc. Natl. Acad. Sci. U.S.A. 103, 19039-44(2006)). This process proceeds through single mutations at a time, and some of these mutation may be deleterious initially though required towards the evolutionary goal set. In this way, natural evolution procedures often result in bottlenecks where too many concomitant mutations are necessary to both obtain the selected phenotype and have a viable organism. Additional approaches that overcome these limitations will prove much more powerful.

SUMMARY

Studies of bacterial resistance to T3 bacteriophages and T7 bacteriophages has revealed that phages routinely adapt to resistance through mutations within genes 11, 12, and/or 17 for T7 and within 17 exclusively for T3 (Perry et al. PLoS One 10, e0130639 (2015); Qimron et al. Proc. Natl. Acad. Sci. U.S.A. 103, 19039-44 (2006)). Both T3 and T7 rely on binding to the outer core LPS for absorption; however, they bind to different LPS moieties which leads to slightly different host ranges (FIG. 1). T7 LPS recognition is carried out by its six trimeric tail fibers encoded by gene 17 and more specifically, by the carboxy terminal domain or the tail fiber tip of gp17 (371-553 aa fragment, or even more specifically, residues 455-553). The T3 gp17 protein is 86% identical and the corresponding host recognizing tip occupies residues 455-558 (FIG. 2A). The extent to which bacteriophage tail fibers delineate bacteriophage host range, and the application of synthetic biology to manipulate bacteriophage tail fiber tips in hopes of modifying bacteriophage host range has, up until now, remained largely unexplored.

Bacteriophage therapy has a rich history and potential to treat the rapid emergence of antibiotic resistant infections. However, limited host range, poorly characterized phage cocktails, and the inadequate evolution of phages to overcome bacterial resistance severely restrict the broad use and application of phage technology.

Described herein are novel approaches to engineering synthetic bacteriophages with altered host ranges. These methods facilitate the rapid evolution of bacteriophages to generate combinatorial phage libraries, where only a small region of the tail fiber is mutagenized (4-9 a.a.). This site-directed approach, which is superior to traditional phage evolution strategies, yields a vast amount of diversity ($10^7$ mutants/mL), while minimally perturbing the overall phage structure and mechanism of infection. This degree of diversity surpasses the capacity of natural phage evolution because it eliminates possible functional bottlenecks that may arise from base-pair mutations and enables the assembly of compositions of phages all derived from the same scaffold to evade bacterial resistance.

In some aspects, synthetic bacteriophages are provided that are characterized by mutations in a tail fiber tip protein, wherein the mutations are engineered in one or more binding loops of the tail fiber tip protein. In another aspect, compositions of synthetic bacteriophages, or compositions comprising two or more types of synthetic bacteriophages, are provided in which the two or more types of synthetic bacteriophages have different mutations in the tail fiber tip protein. In other aspects, collections of synthetic bacteriophages are provided that include a plurality of synthetic bacteriophages having different mutations engineered in two or more loops of a tail fiber tip protein.

In some aspects, methods for treating a bacterial infection are provided that include administering to a subject having a bacterial infection and in need of treatment, the synthetic bacteriophages. In some embodiments, the subject is a mammal. In some embodiments, the subject is a human.

In some aspects, methods of producing one or more synthetic bacteriophages through mutation of one or more binding loops in a tail fiber protein of a bacteriophage are provided.

In some aspects, the tail fiber protein is gp17.

In another aspect, methods of screening a combinatorial bacteriophage library are provided that include: exposing bacterial cells that are normally poorly susceptible or not susceptible at all to bacteriophage infection to the synthetic bacteriophages and identifying synthetic bacteriophages that are capable of sustaining infection of the bacterial cells to an extent that exceeds that of the bacteriophages that contain unmutated binding loops. In this aspect, bacterial cells may be contained in, derived or obtained from patient samples.

In some aspects, methods of generating synthetic bacteriophage compositions that target a bacterial strain and the bacteriophage-resistant variants thereof are provided. The methods include: (a) exposing bacterial cells to synthetic bacteriophages, synthetic bacteriophage compositions, or a collection of synthetic bacteriophages; (b) identifying synthetic bacteriophages that are capable of sustaining infection of the bacterial cells of (a); (c) exposing the bacterial cells of (a) to the synthetic bacteriophages identified in (b) until such time that bacteriophage-resistant variants arise; (d) exposing the bacteriophage-resistant variants of (c) to synthetic bacteriophages, synthetic bacteriophage compositions, or a collection of synthetic bacteriophages; (e) identifying the synthetic bacteriophages that are capable of infecting the bacteriophage-resistant variants; and optionally, iteratively repeating the steps to identify additional synthetic bacteriophages that are capable of infecting additional bacteriophage-resistant variants.

In other aspects, methods of delaying the evolution of a bacterial strain are provided that include exposing the bacterial strain to a synthetic bacteriophage composition that targets the bacterial strain and its common bacteriophage-resistant variants.

In other aspects, methods for suppressing resistance of bacteria to bacteriophage infection are provided. The methods include contacting a population of bacteria with a cocktail of synthetic bacteriophages comprising two or more different host ranges. In some embodiments, the cocktail of synthetic bacteriophages comprises two or more variants or types of synthetic bacteriophages that have different mutations in the tail fiber tip protein. In some embodiments, the step of contacting a population of bacteria with a cocktail of synthetic bacteriophages comprises administering the cocktail of synthetic bacteriophages to a subject. In some embodiments, the subject is a mammal. In some embodiments, the subject is a human. In some embodiments, the step of contacting a population of bacteria with a cocktail of synthetic bacteriophages comprises contacting an isolated population bacteria (such as bacteria derived or obtained from patient samples) with the cocktail of synthetic bacteriophages. In some embodiments, the cocktail comprises synthetic bacteriophages, a composition, or a collection of synthetic bacteriophages as disclosed herein, or synthetic bacteriophages generated as disclosed herein.

In other aspects, methods for preparing a cocktail of synthetic bacteriophages are provided. The methods include obtaining one or more samples from a patient, contacting the bacteria in the one or more samples with a library or bank of synthetic bacteriophages, and identifying synthetic bacteriophages that infect the bacteria in the one or more samples. In some embodiments, the more than one sample is obtained from a patient at different times. In some embodiments, the methods also include combining synthetic bacteriophages that infect the bacteria in the one or more samples in to a cocktail. In some embodiments, the library or bank of synthetic bacteriophages comprises synthetic bacteriophages, a composition, or a collection of synthetic bacteriophages as disclosed herein, or synthetic bacteriophages generated as disclosed herein. In some embodiments, the patient is a mammal. In some embodiments, the patient is a human.

In other aspects, methods for detecting bacteria, identifying bacteria or diagnosing bacterial infections are provided. The methods include contacting a sample containing bacteria with the synthetic bacteriophages, a composition, or a collection of synthetic bacteriophages as disclosed herein, or synthetic bacteriophages generated as disclosed herein, incubating the sample containing bacteria with the synthetic bacteriophages for a time sufficient for the synthetic bacteriophages to infect the bacteria, and detecting the synthetic bacteriophages to detect the presence of one or more bacteria in the sample, to identifying the bacteria or to diagnose bacterial infection. In some embodiments, the sample is obtained from a patient. In some embodiments, the patient is a mammal. In some embodiments, the patient is a human.

These and other aspects of the invention are further described below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 2A. Alignment of the T7 (SEQ ID NO: 152) and T3 (SEQ ID NO: 153) tail fiber products. Identical residues are displayed as dots. The largest rectangular box (corresponding to amino acids 372-553) specifies the fraction of T7 gp17 that has been crystallized. Rectangular boxes B, C, D, E, F, G, H, I, R, S, T, U, V, W, X, Y, and Z represent beta-strands, the rectangular box A represents the alpha-helix that links the pyramidal domain. Rectangular boxes CD, EF, and GH represent random coils that point towards the pyramidal domain whereas the downward facing loops BC, DE, FG, and HI are represented with rectangular boxes BC, DE, FG, and HI, respectively.

FIGS. 5A-5C. Comparison of the modelled structure of T3 and T3(FG:PLDGH) FIG. 5A. The computed surface area of WT T3 gp17 tip is overlaid atop the modelled structure of the T3(FG:PLDGH) gp17 tip. Only loop amino acid side chains are displayed and loops are labeled. The main differences are in the BC loop which is flexible and therefore can accept several configurations and the FG loop were H527 side chains clearly stands out of the T3 gp17 surface area model. FIG. 5B. Side by side axial view comparison of the surface electrostatic potentials of the two tail fiber tips. Polar residues are shaded. H strand residue R546 and G527/H527 are indicated. R546 and H527 in T3(FG:PLDGH) create a very positively charged area. FIG. 5C. Surface area from FG residues only in T3(FG:PLDGH) illustrating that H527 is the major contributor.

FIGS. 6A-6B. FIG. 6A. The sequence of the HI loop of the 16 phagebodies that were isolated on either ΔwaaC or ΔwaaG are aligned to the wild-type sequence (top to bottom: SEQ ID NOs: 154-169). Residues with positively charged side chains are highlighted. FIG. 6B. Model of the T3 gp17 tip structure with each HI loop residue highlighted: D547, A548, P549, and P550. On the left side is a ribbon representation while the molecule surface is displayed on the right. Only D547 and P549 are visible on the latter because neither A548 nor P550 are surface accessible.

FIGS. 13A-13B. DE loop residues Y508 and T504 environments. Residues and features of importance to the reading of these modelled structures from the T3 gp17 tail fiber have been shaded as described in the legend. FIG. 13A. Zoomed in view of the residues surrounding DE loop's Y508. Y508 from monomer A is wedged between the side chain of E525 from that same monomer and the side chains of I519 and F521 from the neighboring monomer. FIG. 13B. T504 is not solvent accessible being located underneath P549.

FIGS. 15A-15F. Capacity of phagebodies to control bacterial population over three consecutive passages using a high-throughput 96-well plate system with a starting bacterial population of $\sim 10^7$ cfu and an MOI of $\sim 10^{-4}$. FIG. 15A, phage T3. FIG. 15B, phagebody T3(BC:AIGRSHLKS). FIG. 15C, phagebody T3(BC:MHGKSYMGG). FIG. 15D, phagebody T3(HI:ASRV). FIG. 15E, phagebody T3(BC: AAGKNALGG). FIG. 15F, phagebody T3(HI:RDIRLSI).

FIG. 16A. Schematic showing the phage panning procedure to amplify out functional phages. FIG. 16B. Efficiency of plating plots summarizing the amplification of functional mutant phages and dilution of T3 WT per round of passaging on mutant strain. Rows are organized by the strain the bank was passaged on: top: truncated outer core LPS (i.e., minimal LPS); middle: LPS outer core void (i.e., LPS void); and bottom: mutant bacteria isolated from growth curve of T3 WT (i.e., T3 mutant). Columns are organized by the bank that was being passaged. BL21 cultures were originally infected with the phage bank for round 0 and every subsequent round was infected with supernatant from the prior infection.

FIG. 21A. Schematic illustrating the similarities between antibody engineering and the phagebody strategy. In an antibody, antigen recognition is primarily encoded by six hypervariable complement-determining regions (CDRs), three on the heavy chain and three on the light chain. The inset presents the three-dimensional structure of the variable domain of an antibody (PDB ID HGT). In phage T7, host range is largely determined by the C-terminus of its tail fiber protein, gp17. The insets show the crystallographic structure of the C-terminal 182 amino acids of T7 gp17 (PDB ID 4A0T). Outward loops are expected to participate in receptor recognition while tolerating mutations. Phagebodies are designed to carry mutations in these loops while leaving other structures of the tail fiber intact. FIG. 21B. Schematic illustrating how resistance appears in bacterial cultures and how phagebody cocktails or individual phagebodies may suppress resistance.

FIGS. 22A-22B. Structure and sequence of the T3 gp17 tip. FIG. 22A. Three-dimensional structure of the tail fiber tip domain of phage T3 as modeled by SWISS-MODEL. The molecular surface encompassed by the residues belonging to the BC, DE, FG and HI loops are highlighted to illustrate their possible contribution to host binding. FIG. 22B. Sequence of the T3 tail fiber tip (gp17 a.a. 455-558 fragment) modeled in FIG. 22A (SEQ ID NO: 185).

FIGS. 23A-23J. Phagebody libraries exceed $10^7$ unique phages. FIG. 23A. Schematic showing the strategy to synthesize phagebody libraries. FIG. 23B. Table summarizing the theoretical diversity for each library synthesized. FIGS. 23C-23I. Illumina HiSeq characterization of phagebody libraries quantifying library diversity. Each plot shows a rarefaction curve characterizing library diversity at each stage of synthesis. FIG. 23J. Legend for FIGS. 23C-23I. Solid lines are guides showing 100%, 10%, and 1% coverage of theoretical maximum sequence space. Circles correspond to synthesized plasmid libraries, squares indicate plasmid libraries recovered post transformation, and triangles specify phage libraries post recombination.

FIGS. 24A-24D. Phagebodies display broadened host range towards BL21 mutants that are resistant to wild-type T3. FIG. 24A. LPS structures for wild-type BL21 and the wild-typeT3-resistant BL21 mutants constructed for phagebody isolation. Highlighted with an arrow and an asterisk are the sugar residues that act as receptors for T3 and T7, respectively. FIG. 24B. Phage titer for 4 independent phagebody libraries designed to randomize the indicated loops. Titer was measured on wild-type BL21 (top row), ΔwaaG (middle row), and ΔwaaC (bottom row) in triplicate for each library and the data is plotted as mean+/−standard deviation. This data illustrates the reproducibility of library construction and the repeated failure of some libraries to produce host-range-altered phagebodies. FIG. 24C. Representative image of plaque assays from one of the HI loop phagebody libraries highlighting individual plaques. FIG. 24D. Heat map summarizing the efficiency of plating (EOP; ratio of wild-type T3 or phagebody PFU on the tested bacterial mutant versus wild-type T3 or phagebody PFU on wild-type BL21) for randomly isolated and plaque-purified phagebodies on a panel of experimentally isolated wild-type-T3-resistant bacterial mutants (D10; FSL396-402) and the two constructed isolation hosts, ΔwaaC and ΔwaaG. The phagebodies are sorted based on performance. Class 1 phagebodies are marginally better than wild-type T3, failing to infect all tested mutants and doing so at low EOP ($\log_{10}$ EOP on mutants <−2); Class 2 phagebodies infect all test strains but poorly ($\log_{10}$ EOP<−2 for at least one test strain); Class 3 phagebodies infect all test strains as efficiently as wild-type BL21 ($\log_{10}$ EOP~0); Class 4 phagebodies have lost the capacity to infect wild-type BL21 but infect LPS mutants efficiently ($\log_{10}$ EOP>2).

FIGS. 25A-25H. Kinetic plots showing growth curves of wild-type BL21 bacterial cultures that were infected with phagebody libraries. As a control, wild-type T3 was grown on E. coli NEB5α carrying a wild-type T3 gene 17 plasmid (WT gene 17) in order to mimic the phagebody library construction conditions but without mutagenizing the plasmid-borne gene 17. Bacterial growth was followed through optical density at 600 nm. Each plot consists of 10 replicates from three independent experiments. Error bars show the SEM. Cultures were infected at a MOI of 0.01.

FIG. 27A. Resistance index for each randomly isolated phagebody (lower is better). The resistance index is based on counting the number of resistant colonies growing on plates inoculated with ~$10^9$ CFU of wild-type BL21 and ~$10^5$ PFU of wild-type T3 phage (as reference) or a phagebody, in top agar after 24 hours of incubation. The resistance index is the $\log_{10}$ of the ratio between these two counts. The vertical patterned lines indicate arbitrarily chosen thresholds of improved resistance prevention compared to T3 (same as (|), 10× better (+) or 250-fold better (×)) from right to left) and are presented to help visualize best and worse phagebodies. 3 data points are estimated because they had too many colonies to count (○) or no resistant colonies at all (▲). The shading is the same as in FIG. 24D and is meant to help correlate the two datasets. The data is represented as mean+/−95% confidence interval. FIG. 27B. Select phagebodies were co-cultured with wild-type BL21 in four independent microcosms for 6 days with daily reseeding in fresh medium and bacterial titer was recorded before each subculture. The same protocol was applied to four independent wild-type BL21 microcosms infected with wild-type T3 as a control. Phagebodies presented on the top line were best at controlling bacterial growth, as all 4 replicate microcosms maintained bacterial levels that were several orders of magnitude below the starting titer of the culture (~$10^9$ CFU/ml). All phagebodies performed better than wild-type T3.

FIGS. 30A-30B. Related to FIG. 24 and FIG. 25: Panning phagebody lysates on selective hosts unveils rare phagebodies. FIG. 30A. Schematic showing the phage panning procedure to amplify functional phagebodies out of libraries. FIG. 30B. Efficiency of plaquing plots summarizing the amplification of functional mutant phages and dilution of wild-type T3 per round of passaging on mutant strain. Rows are organized by the strain the library was passaged on: top—ΔwaaG; middle—ΔwaaC; and bottom—T3-resistant mutant D10 isolated from a wild-type BL21 culture infected with wild-type T3. Columns are organized by the phagebody library that was being passaged. Wild-type BL21 cultures were originally infected with the phage library for round 0 and every subsequent round was infected with supernatant from the prior infection.

DETAILED DESCRIPTION

Figure 1:
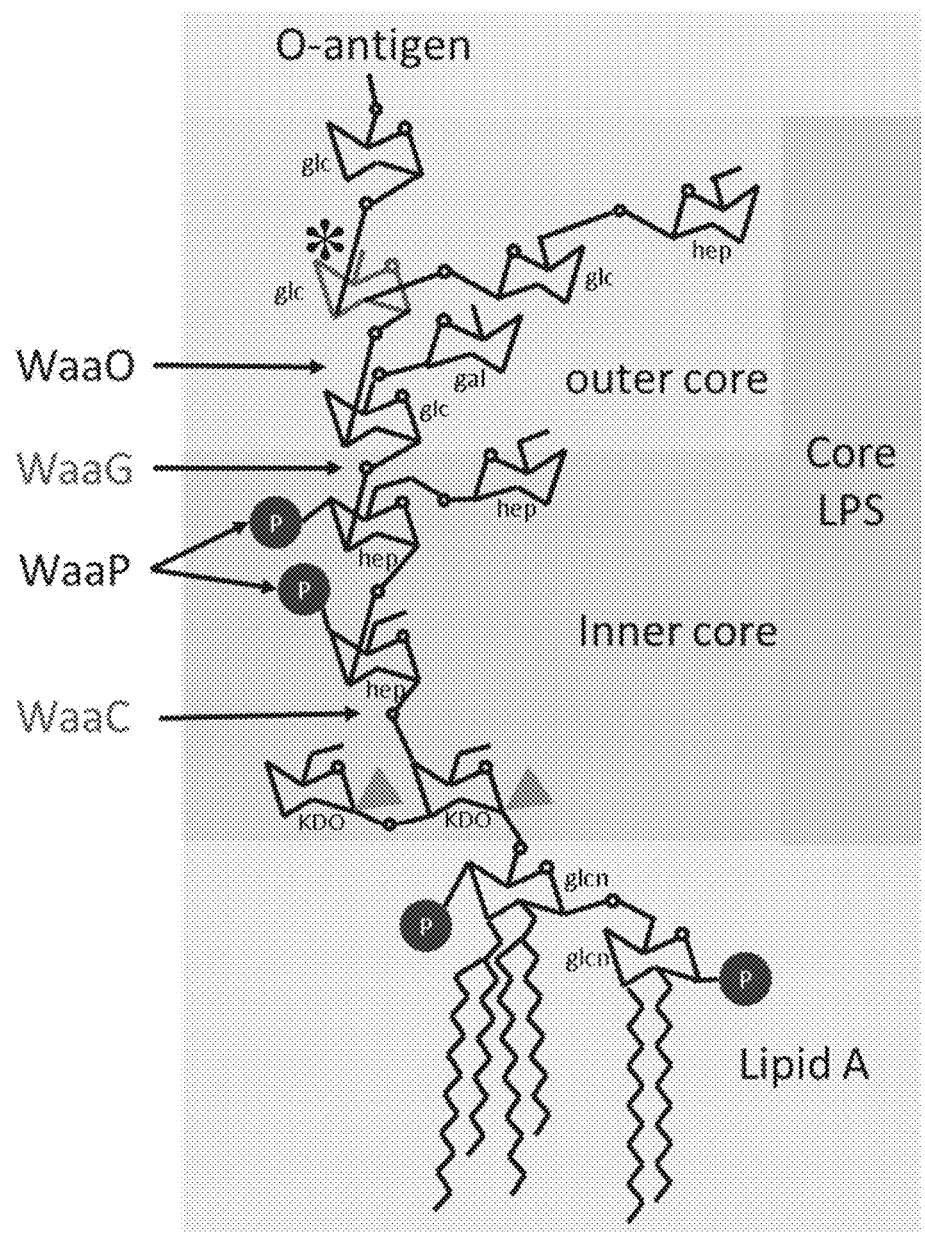
FIG. 1. Schematic representation of the E. coli BL21 LPS and relevant synthesis enzymes. The E. coli BL21 structure was assembled from biocyc database information. The glucose moiety (marked with an asterisk) is that which is used as a receptor by T3. Glcn: α-D-glucosamine, Glc: α-D-glucose, Gal: α-D-galactose, Hep: glycero-β-D-manno-heptose, KDO: 3-deoxy-D-manno-octulosonate FIGS. 2A-2B. Bacteriophage tail fiber primary and tertiary structure.

The rapid escalation of drug resistant bacterial infections and decreased investment in antibiotic research make it imperative to develop alternative therapies. A resurging approach gaining significant interest is phage therapy (PT) whereby bacteria targeting viruses (bacteriophages or phages for short) are used as antimicrobials or for delivery of genetic circuits with antimicrobial or physiological activities (Chen et al., J. Clin. Invest. 124, 3391-406 (2014); Devlin et al., Cell Host Microbe. 20, 709-15v (2016); Shen et al., J. Clin. Invest. 125, 2841-50 (2015); Kutter et al. Curr. Pharm. Biotechnol. 11, 69-86 (2010); Kutateladze and Adamia, Trends Biotechnol. 28, 591-95 (2010); Kutter et al. Future Microbiol. 10, 685-88 (2015); Citorik et al. Nat. Biotechnol. 32, 1141-45 (2014); Bikard et al. Nat. Biotechnol. 32, 1146-50 (2014); Maynard et al. PLoS Genet. 6 (2010); Lu and Collins, Proc. Natl. Acad. Sci. U.S.A. 104, 11197-202 (2007); Lu and Collins, Proc. Natl. Acad. Sci. U.S.A. 106, 4629-34 (2009)). Phages are exquisitely selective of their host, which makes phage therapy less destructive of the normal and beneficial microflora of the patient compared to conventional chemical antibiotics (Galtier et al. Environ. Microbiol. 18, 2237-45 (2016)). Bacteriophages are also functionally orthogonal to antibiotics, which means they are generally unaffected by acquisition of antibiotic resistance making them particularly adapted to the treatment of Anti-Microbial Resistant (AMR) infections (Miedzybrodski et al. Adv. Virus Res. 83, 73-121 (2012)). A further advantage of phages is their self-dosing capacity in that they can replicate to the extent of the infection. However, this also makes traditional pharmacodynamics methods inadequate for PT.

Although independent of antibiotic resistance mechanisms, bacteria have evolved various resistance solutions against phage predation. Bacteriophage initiate infection through the specific recognition of a surface exposed receptor molecule, protein, lipopolysaccharide (LPS) or capsule component, which if mutated or masked deprives the virus of its entry port (Labrie, et al. Nat. Rev. Microbiol. 8, 317-27 (2010)). Resistance to phages may also arise from acquisition of dedicated phage defense mechanisms such as CRISPR or abortive infection systems (Labrie, et al. Nat. Rev. Microbiol. 8, 317-27 (2010)). Finally, the need for phages to recognize a specific receptor translate into relatively narrow host ranges for most naturally occurring phages. This in turn, means that no single phage may be active against all (or a medically relevant fraction of) bacteria involved in any given disease.

These issues are traditionally alleviated by empirically assembling and regularly updating cocktails of un-related phages that are collectively able to eliminate the affliction. However, this leads to often poorly defined mixtures that are largely incompatible with modern medical standards for safety testing and regulatory approval. Because these cocktails are composed of phages with completely distinct properties, they may require individual protocols for production, storage and manufacturing, which further complicates establishment of good manufacturing practices, an essential part of drug approval processes. As a result and despite its enormous potential, phage-based therapies have struggled to gain momentum (Cooper et al. Front. Microbiol. 7, 1209 (2016)).

Researchers have long observed that in the predator and prey relationship between phage and bacteria, the prey almost systematically outcompete the predator (Alexander, Annu. Rev. Microbiol. 35, 113-33 (1981)). Various models have been proposed. The most simplistic one explains that because phage genomes are small and densely packed, the likelihood of deleterious mutations is higher than in their host so that bacteria can tolerate more mutations. This eventually leads to bacterial resistance before collapsing, thus giving bacteria an edge in the arms race with phages. Such a phenomenon, is one of the reason that sustains distrust in the use of phages as therapeutics.

Various approaches have been undertaken to expand the host range of phages to combat resistance (Ando et al. Cell Syst. 1, 187-196 (2015); Chen et al., Front. Microbiol. 8, 147 (2017); Gebhart et al., Virology 505, 263-66 (2017); Hawkins et al., Virol. J. 5, 97 (2008); Heilpern and Waldor, J. Bacteriol. 185, 1037-44 (2003); Lin et al., PLoS One 7, e30954 (2012); Nguyen et al., Evolution 66, 363-74 (2012);

Scholl et al., Antimocrob. Agents Chemother. 53, 3074-80 (2009); Yoichi et al., J. Biotechnol. 115, 101-7 (2005); Yosef et al., J. Biotechnol. 115, 721-28 (2017)). (Ando et al. Cell Syst. 1, 187-196 (2015)). However, these approaches rely on hybridization between already characterized bacteriophages with known and desired host ranges, which is very limited and often results in long and unpredictable trial and error periods. It is, therefore, not well suited to the isolation of mutant phages that may target bacteria that have evolved receptor mutations as a result of phage predation. Alternatively, some studies have relied on traditional phage mutant selection procedures which utilize natural evolution ((Nguyen et al., Evolution 66, 363-74 (2012); Springman et al., Genetics 184, 221-32 (2010); Perry et al. PLoS One 10, e0130639 (2015); Qimron et al. Proc. Natl. Acad. Sci. U.S.A. 103, 19039-44(2006)). This process proceeds through single mutations at a time and some of these mutation may be deleterious initially though required towards the evolutionary goal set (Alexander, Annu. Rev. Microbiol. 35, 113-33 (1981); Bull et al., PLos One 9, e94690 (2014); Levin and Bull, Nat. Rev. Microbiol. 2, 166-73 (2004); Meyer et al., Science 335 428-32 (2012); Nguyen et al., Evolution 66, 363-74 (2012); Perry et al. PLoS One 10, e0130639 (2015); Qimron et al. Proc. Natl. Acad. Sci. U.S.A. 103, 19039-44 (2006); Studier et al., J. Mol. Biol. 258, 726-31 (2009); Tétart et al., J. Mol. Biol. 258, 726-31 (1996)). Thus, the natural evolution procedure often reaches bottlenecks where too many concomitant mutations are necessary to both obtain the selected phenotype and have a viable organism.

Previous studies have demonstrated that the T7-family of phages is particularly amenable to phage host range engineering (Ando et al. Cell Syst. 1, 187-196 (2015)). T7-family phages have an extremely host independent life cycle so that DNA entry into the host range is the most significant barrier to generating progeny. The experiments described here have focused on phage T3 because it has a slightly more limited host range than its close relative T7 which therefore affords more room for phenotypic improvement. The two phages are extremely similar and share an extremely similar developmental cycle (Calendar, The Bacteriophages 2nd Edition).

Studies of bacterial resistance to T3 bacteriophages and T7 bacteriophages have revealed that phages routinely adapt to resistance through mutations within genes 11, 12, and/or 17 for T7 and within 17 exclusively for T3 (Perry et al. PLoS One 10, e0130639 (2015); Qimron et al. Proc. Natl. Acad. Sci. U.S.A. 103, 19039-44 (2006)). Both T3 and T7 rely on binding to the outer core LPS for absorption; however, they bind to different LPS moieties which leads to slightly different host ranges (FIG. 1).

Figure 2A:
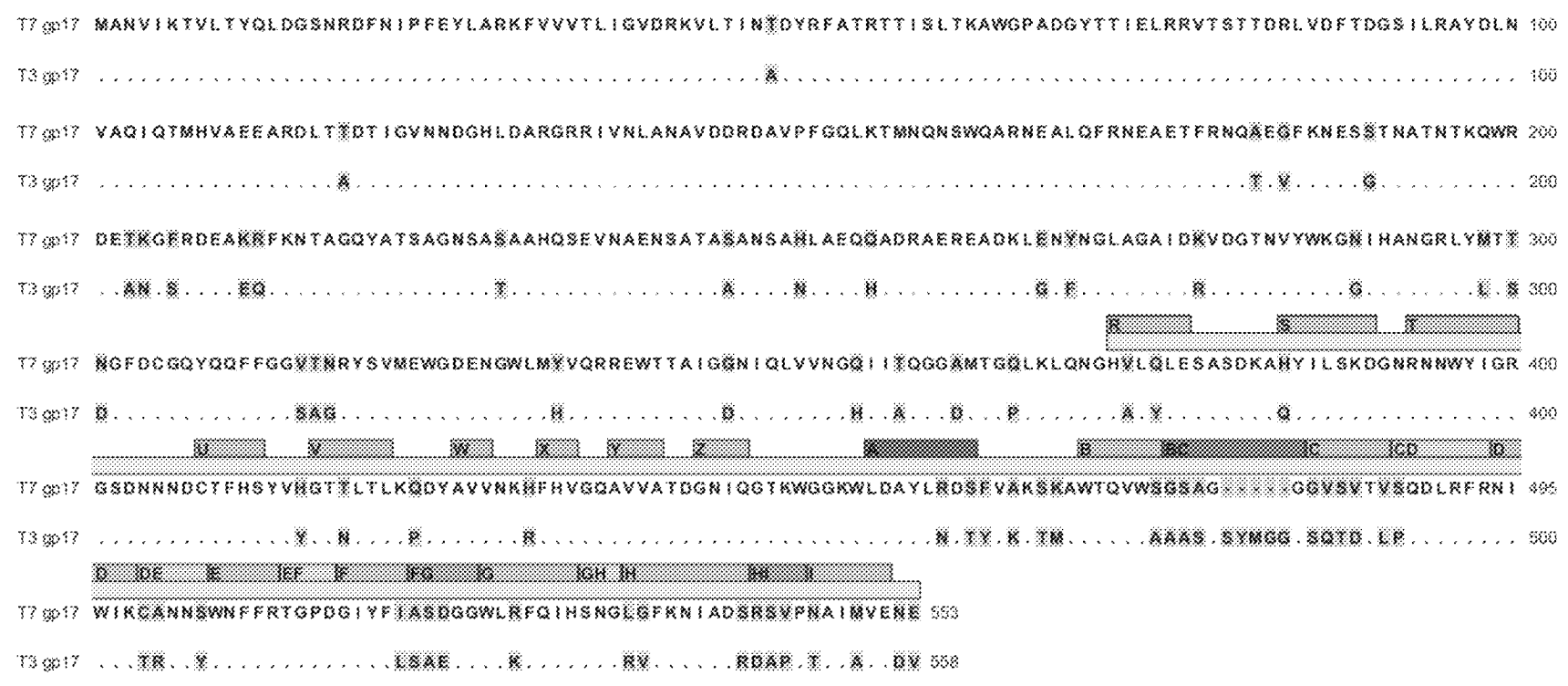
Figure 2B:
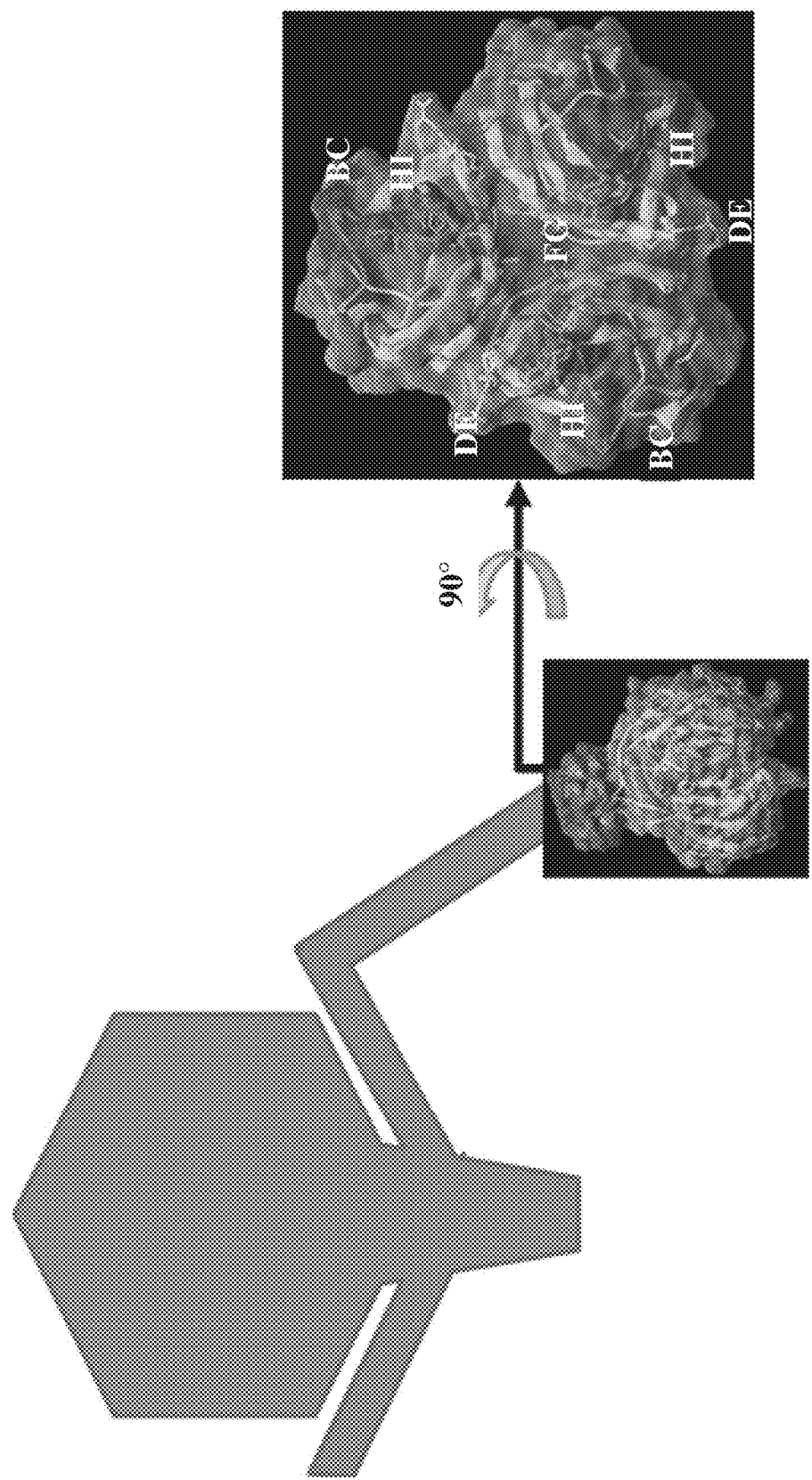
FIG. 2B. 3D structure of the T7 gp17 last 99 amino acids from helix A to the very end of the protein as seen from the side or axially. Important contribution of loops BC, DE, FG and HI to the basal surface of the tip domain and the complete absence of the other inter strand loops. Side chains are shown for the BC, DE, FG and HI loops only.

Recently, the T7 gp17 tip was crystallized and its structure resolved (Garcia-Doval and Van Raaij. Proc. Natl. Acad. Sci. U.S.A. 109 (2012)). It is 75% identical to the corresponding region of T3 gp17 (FIG. 2A), and the structure of the T3 tail fiber tip can therefore be modelled with high accuracy using homology modelling tools such as Swiss-model (FIG. 2B) (Arnold, Bioinformatics. 22, 195-201 (2006)). The distal 106 aa of gp17 form an intertwined globular domain shaped by an eight stranded beta barrel (labelled B to I) connected by random coils. Four of those coils, BC, DE, FG and HI, are pointed towards the exterior side of the tail fiber and are therefore uniquely positioned to contact the host and recognize the receptor moiety (FIG. 2I). The extent to which bacteriophage tail fibers delineate bacteriophage host range, and the application of synthetic biology to manipulate bacteriophage tail fiber tips in hopes of expanding bacteriophage host range has, up until now, remained unexplored.

Disclosed herein are strategies and methods for engineering synthetic bacteriophages with expanded host ranges. In contrast to previous approaches, the methods described herein focus on producing vial phages with subtle host range alterations to target resistant mutants. These methods are rapid and simple enough that they can be used to scan for the most important regions involved in host recognition. Importantly, because these methods are directed towards short loop regions, they can be used to discover phage mutants that would require too many point mutations to ever be produced by evolution, naturally or in vitro (Nguyen et al., Evolution 66, 363-74 (2012); Springman et al., Genetics 184, 221-32 (2010)). Finally, these methods are versatile because they are compatible with other forms of phage engineering (synthetic genome reconstruction or Gibson assembly of full phage genomes), selection of other phenotypes (e.g., selection of faster or slower replication rates or altered immunogenicity of the phage), and are also compatible with random mutagenesis to enrich mutations outside of the immediately targeted region. However, these methods are also simple and fast enough that iterative cycles can be performed to generate phagebodies mutated in several loops concurrently.

Moreover, methods are described that facilitate the rapid evolution of bacteriophages to generate combinatorial phage libraries. This combinatorial-based approach, which is superior to previous phage cocktails, yields a vast amount of diversity ($10^7$ mutants/mL), while minimally perturbing the overall phage structure and mechanism of infection. Finally, this amount of diversity surpasses that of natural phage evolution and enabled the assembly of a cocktail of phages all derived from the same scaffold to evade bacterial resistance.

Disclosed herein are synthetic bacteriophages having mutations in a tail fiber tip protein (also referred to herein as "phagebodies"). The mutations are engineered in one or more binding loops of the tail fiber tip protein. More specifically, in some embodiments the engineered mutations are identified using the methods disclosed herein, and can be generated by non-natural methods such as synthesis of sequences of one or more binding loops to introduce mutations relative to the wild-type sequence. The binding loops of the tail fiber tip protein are engaged in binding molecules on the surface of bacteria, and face the basal or apex side of the tail fiber protein.

In some embodiments, the mutations are in one or more of coils BC, DE, FG and/or HI of the tail fiber protein. As demonstrated herein, these coils can be mutagenized to alter the ability of a synthetic bacteriophage to infect particular bacteria, i.e., the mutagenized synthetic bacteriophages have a different host range than a bacteriophage with unmutated binding loops of the tail fiber tip protein. Coils BC and HI are particularly suited for mutagenesis to produce host range altered synthetic bacteriophages (phagebodies).

The mutations introduced to produce the synthetic bacteriophages can be substitution mutations, deletions, or insertions/additions. As is shown below, the coils in the binding loops of the tail fiber protein can have one or more amino acids substituted for the wild-type amino acid(s). It also is possible to add amino acids or delete amino acids, for example at one or both ends of a coil, to provide longer or shorter coil sequences. The types of mutations can be mixed such that, for example, one coil contains a substitution mutation of one or more amino acids, and another coil contains an addition and/or deletion mutation. The types of mutations also can be mixed such that, for example, one coil contains both a substitution mutation of one or more amino acids, and an addition and/or deletion mutation.

In some embodiments, the engineered mutations in the one or more binding loops of the tail fiber tip protein of the synthetic bacteriophage are the only mutations in the synthetic bacteriophage. However, the synthetic bacteriophages are not limited in this aspect, and may contain other mutations in other proteins, such as for providing the synthetic bacteriophage with one or more additional functional features.

As shown herein, the synthetic bacteriophage can be a T3 bacteriophage. Other similar bacteriophage can likewise be generated to have mutations in a tail fiber tip protein, such as a T7 bacteriophage or a bacteriophage having about 75%, 80%, 85%, 90%, 91%, 92%, 93%, 94%, 95%, 96%, 97%, 98%, or 99% amino acid identity to a T3 bacteriophage tail fiber tip protein.

In some embodiments, the tail fiber tip protein mutated in the synthetic bacteriophage is gp17. Other tail fiber tip proteins are known to those of skill in the art.

Compositions of the synthetic bacteriophage also are provided. Such compositions can include a pharmaceutically-acceptable carrier. Generally, for pharmaceutical use, the synthetic bacteriophages may be formulated as a pharmaceutical preparation or compositions comprising at least one synthetic bacteriophage and at least one pharmaceutically acceptable carrier, diluent or excipient, and optionally one or more further pharmaceutically active compounds. Such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such administration forms may be solid, semi-solid or liquid, depending on the manner and route of administration. For example, formulations for oral administration may be provided with an enteric coating that will allow the synthetic bacteriophages in the formulation to resist the gastric environment and pass into the intestines. More generally, synthetic bacteriophage formulations for oral administration may be suitably formulated for delivery into any desired part of the gastrointestinal tract. In addition, suitable suppositories may be used for delivery into the gastrointestinal tract. Various pharmaceutically acceptable carriers, diluents and excipients useful in synthetic bacteriophage compositions are known to the skilled person.

The synthetic bacteriophage compositions have, in some embodiments, a single type of synthetic bacteriophage. More typically, however, the synthetic bacteriophage compositions include two or more variants or types of synthetic bacteriophages that have different mutations in the tail fiber tip protein, i.e., a "cocktail" of synthetic bacteriophages. In some embodiments, the two or more types of synthetic bacteriophages advantageously have different host ranges, which provides for enhanced resistance to bacterial mutations in the exterior components that are bound by the tail fiber tip protein of the synthetic bacteriophages.

Also provided are collections (also referred to as "libraries" or "banks") of synthetic bacteriophages, which include a plurality of synthetic bacteriophages having different mutations engineered in one or more loops of a tail fiber protein. As noted above, such mutations may be substitutions, additions, or deletions.

Also provided are methods for treating a bacterial infection using the synthetic bacteriophages disclosed herein. The methods include administering the synthetic bacteriophages or compositions disclosed herein to a subject having a bacterial infection in need of treatment. In some embodiments, the subject is a mammal. In some embodiments, the subject is a human.

Methods of producing one or more synthetic bacteriophages also are provided. In such methods, one or more binding loops in a tail fiber tip protein of a bacteriophage is mutated to produce a synthetic bacteriophage. As disclosed in the examples below, such mutations can be introduced by synthesizing portions of the tail fiber tip protein using degenerate primers that vary the nucleotide sequence, and thereby introduce substitutions of amino acids (or additions or deletions) in one or more coils of the binding loops of the tail fiber tip protein.

In some embodiments, one or more codons within at least one binding loop of a tail fiber tip protein can be replaced with the degenerate codon NNK to introduce amino acid variability in the at least one loop.

For example, replacing one or more codons can be achieved by amplifying a sequence comprising a bacteriophage gp17 gene region to produce an amplification product. The amplification can be carried out using PCR primers encoding the nucleic acid sequence NNK for at least one of the amino acid codons. Such methods also can include circularization of the amplification product; introduction of the circularized amplification product into bacteriophage susceptible bacterial cells; infection of the bacterial cells with wild-type bacteriophages, wherein said infection facilitates the recombination of the wild-type bacteriophage with the amplification product; and isolation of recombinant bacteriophages comprising the amplification product.

Also provided are methods of screening one or more synthetic bacteriophages for ability to infect bacteria. The synthetic bacteriophages (or compositions containing such compositions, or collection or library of synthetic bacteriophages), which can be produced as disclosed herein, are exposed to bacterial cells and synthetic bacteriophages are identified that are capable of sustaining infection of the bacterial cells to an extent that exceeds that of the bacteriophages that contain unmutated binding loops. In some embodiments, the bacterial cells are E. coli cells. Examples of such bacterial cells include ΔwaaG mutants or ΔwaaC mutants, as are shown in the working examples. Other types of bacteria that are susceptible to synthetic bacteriophages will be known to a skilled person, and can be selected based on the host range of the wild type bacteriophages used in engineering the synthetic bacteriophages.

Also provided are methods of generating synthetic bacteriophage compositions that target a bacterial strain and the bacteriophage-resistant variants thereof. Such methods include repeated exposure of synthetic bacteriophages to bacterial cells such that bacteriophage-resistant variants arise, and further culturing with synthetic bacteriophages such that synthetic bacteriophages capable of infecting of the bacteriophage-resistant variants are obtained. In some embodiments, the methods include exposing bacterial cells to synthetic bacteriophages that are described herein and which may be produced using the methods described herein; identifying synthetic bacteriophages that are capable of sustaining infection of the bacterial cells; exposing the same bacterial cells to the synthetic bacteriophages identified until such time that bacteriophage-resistant variants arise; exposing the bacteriophage-resistant variants to synthetic bacteriophages; and identifying the synthetic bacteriophages that are capable of infecting of the bacteriophage-resistant variants. The methods also can include iteratively repeating the steps to identify additional synthetic bacteriophages that are capable of infecting additional bacteriophage-resistant variants. The methods also can include combining the synthetic bacteriophages identified to produce a composition, which optionally can include carriers, diluents and/or excipients.

Also provided herein are methods of delaying the evolution of a bacterial strain. Such methods include exposing the bacterial strain to a synthetic bacteriophage composition that targets the bacterial strain and its common bacteriophage-resistant variants, such as is produced by the method described above.

Also provided herein are methods for suppressing resistance of bacteria to bacteriophage infection. The methods include contacting a population of bacteria with a cocktail of synthetic bacteriophages comprising two or more different host ranges. In some embodiments, the cocktail of synthetic bacteriophages comprises two or more variants or types of synthetic bacteriophages that have different mutations in the tail fiber tip protein. In some embodiments, the step of contacting a population of bacteria with a cocktail of synthetic bacteriophages comprises administering the cocktail of synthetic bacteriophages to a subject. In some embodiments, the subject is a mammal. In some embodiments, the subject is a human. In some embodiments, the step of contacting a population of bacteria with a cocktail of synthetic bacteriophages comprises contacting an isolated population bacteria (such as bacteria derived or obtained from patient samples) with the cocktail of synthetic bacteriophages. In some embodiments, the cocktail comprises synthetic bacteriophages, a composition, or a collection of synthetic bacteriophages as disclosed herein, or synthetic bacteriophages generated as disclosed herein.

Also provided herein are methods for preparing a cocktail of synthetic bacteriophages. The methods include obtaining one or more samples from a patient, contacting the bacteria in the one or more samples with a library or bank of synthetic bacteriophages, and identifying synthetic bacteriophages that infect the bacteria in the one or more samples. In some embodiments, the more than one sample is obtained from a patient at different times. In some embodiments, the methods also include combining synthetic bacteriophages that infect the bacteria in the one or more samples in to a cocktail. In some embodiments, the library or bank of synthetic bacteriophages comprises synthetic bacteriophages, a composition, or a collection of synthetic bacteriophages as disclosed herein, or synthetic bacteriophages generated as disclosed herein. In some embodiments, the patient is a mammal. In some embodiments, the patient is a human.

Also provided herein are methods for detecting bacteria, identifying bacteria or diagnosing bacterial infections. The methods include contacting a sample containing bacteria with the synthetic bacteriophages, a composition, or a collection of synthetic bacteriophages as disclosed herein, or synthetic bacteriophages generated as disclosed herein, incubating the sample containing bacteria with the synthetic bacteriophages for a time sufficient for the synthetic bacteriophages to infect the bacteria, and detecting the synthetic bacteriophages to detect the presence of one or more bacteria in the sample, to identifying the bacteria or to diagnose bacterial infection. In some embodiments, the sample is obtained from a patient. In some embodiments, the patient is a mammal. In some embodiments, the patient is a human. If samples are obtained from a patient at different times, the progress of bacterial infection can be monitored and tracked, as can the efficacy of anti-bacterial therapies.

EXAMPLES

Methods and Materials
Strains and Culture Conditions

Bacteriophage T3 was obtained from Ian Molineux (University of Texas, Austin) and maintained on E. coli BL21. Cloning was performed in E. coli NEB5a. Bacteria were grown in Lysogeny Broth (LB medium; LabExpress) at 37° C. with agitation at 250 rpm from isolated colonies grown on LB plates from frozen stocks and stored at −80° C. in 45% glycerol. As needed, the medium was supplemented with kanamycin (kan; 50 µg/ml final concentration), carbenicillin (carb; 50 µg/ml final concentration), apramycin (50 µg/ml final concentration), and/or glucose (glc; 0.2% w/v final concentration). LB plates contained agar (LabExpress) at a final concentration of 1.5%. Top agar was LB agar 0.6%. T3 resistant strains FSL397-402 and D10 were picked from T3 infected lawns of wild-type E. coli BL21 incubated at 37° C. until resistant colonies grew. They were picked, streaked to isolation twice, and tested for T3 resistance.

DNA Manipulation and Sequencing

Polymerase Chain Reaction was performed using either KAPA Biosystems Hifi or KAPA2G Robust DNA polymerases. Standard PCR conditions for these two polymerase are presented in TABLE 1A. DNA fragments were purified using the DNA clean up and concentration kit from Zymo Research. Plasmids were extracted using the plasmid mini- or midiprep kits from the same source depending on the scale of the plasmid preparation. Restriction enzymes were purchased from New England Biolabs.

All these reagents and kits were used following the manufacturer's recommendations.

TABLE 1A

PCR programs used in this study.

| KAPA HiFi PCR Conditions | | |
|---|---|---|
| 1X | 95° C. | 3 min |
| 25X | 98° C. | 20 s |
|  | 65° C. | 15 s |
|  | 72° C. | 30 s/kb |
| 1X | 72° C. | 10 min |
| KAPA2G Robust PCR Conditions | | |
| 1X | 95° C. | 3 min |
| 25X | 95° C. | 20 s |
|  | 60° C. | 20 s |
|  | 72° C. | 15 s/kb |
| 1X | 72° C. | 10 min |

Plasmid Construction

Plasmids constructed and used in this project are listed in TABLE 3. pSLM49 was constructed by assembling the PCR amplified replication origin and resistance marker from pFF753 (primers PST480 and PST481) (Farzadfard et al. Science 346, 1256272 (2014)) with a PCR amplified fragment from phage T3 containing gene 17 (PST575 and PST576) using the BamHI and XmaI sites added to the primer sequences.

pSLM193-197 and pSLM225-233 are derivatives of pSLM49 built by cloning the gene 17 tip sequence from select phagebodies in lieu of the wild-type tip sequence. The gene 17 tips were amplified through primers PST691/692 and the rest of the plasmid with PST693/694. The two PCR fragments were then assembled by Gibson® reaction. pSLD18 is a derivative of pSIM9 (Datta et al., Gene 379: 109-15 (2006)) where the chloramphenicol marker was replaced with the erythromycin marker of pCP1 (Le Bourgeois et al., Gene 111, 109-14 (1992)). pSLM111alpha was obtained by ligating the apramycin resistance marker of plasmid pSET152 (Bierman et al., Gene 116, 43-9 (1992)) amplified with primers PST816 and PST817 and the backbone of pKD3 (Datsenko and Wanner, Proc. Natl. Acad. Sci. U.S.A. 97, 6640-45 (2000)) amplified with primers PST818 and PST819 after restriction of both fragments with PspoMI.

pSLM173 was constructed from pNR63, which is a pSC101 based plasmid with an ampicillin resistance marker and an AHL regulated promoter in front of the BxbI integrase gene. The replication origin, selection marker and AHL controlled promoter were PCR amplified with primers PST1089 and 1090 while the E. coli BL21 waaG gene was amplified with primers PST1091BL and PST1092BL (TABLE 2). The resulting amplicons were assembled using the Gibson reaction.

LPS Mutant Construction

E. coli BL21 was transformed with the recombineering plasmid pSLD18—which is pSIM9 (Datta et al. Gene 379, 109-15 (2006) with its chloramphenicol marker replaced with the erythromycin resistance marker from pRC1—and cells made recombineering proficient. The cells were electroporated with a PCR product designed to replace waaC or waaG with an apramycin resistance marker amplified from pSLM111alpha with primers PST853/PST854 and PST857/PST858 respectively (TABLE 2). Proper deletion was then verified by PCR.

Tail Fiber Library Creation

Diversity was introduced at the DNA level in pSLM49. Two different methods were used: (1) Direct transformation of PCR products with terminal redundancy and (2) a restriction-ligation based method.

Directed Transformation of PCR Products:

In the first method, the entire pSLM49 plasmid was PCR amplified with a pair of diverging primers annealing on each site of the target loop. In one of the oligonucleotides, the target loop sequence was replaced by a series of NNK codons. The NNK stretch is preceded in 5' by the complementary sequence to the reverse primer so that the final PCR product has a 20-30 bp identical sequence at each end. The amplicons were then DpnI digested to eliminate template DNA and about 100-500 ng of that DNA was transformation into chemically competent NEB5α cells following the manufacturer's instructions. The termini of the PCR products were redundant such that the PCR product circularized reconstituting gene 17 present in pSLM49 but with a random sequence in place of the targeted loop. The bacteria were recovered for 1 hour at 37° C. in SOCS medium (1 mL). After this step, the transformation yield was determined by plating serial dilutions of culture on LB-kanamycin agar plates. The 1 mL bacterial cultures were then diluted with 9 mL of LB-kanamycin and grown overnight at 37° C. and 250 rpm of shaking. The next day, fresh cultures were started by diluting 1 mL of overnight culture into 9 mL of LB, while the remaining culture was pelleted and stored at −20° C. for plasmid DNA extraction/sequencing. Phage lysates were made by infecting bacterial cultures at exponential growth phase ($OD_{600}$=0.7) with $10^7$ plaque forming units (PFU) of T3 (100 μL). The cultures were grown for another 2-3 hours until the cultures cleared. Phage lysates were chloroform treated with 500 μL of chloroform for 30 minutes to kill any remaining bacteria, spun down to remove debris and filtered through a 0.22 μm filter. Phage lysates were spun down at 7,000 G for 5 minutes and stored at 8° C. for long-term storage.

Figure 17:
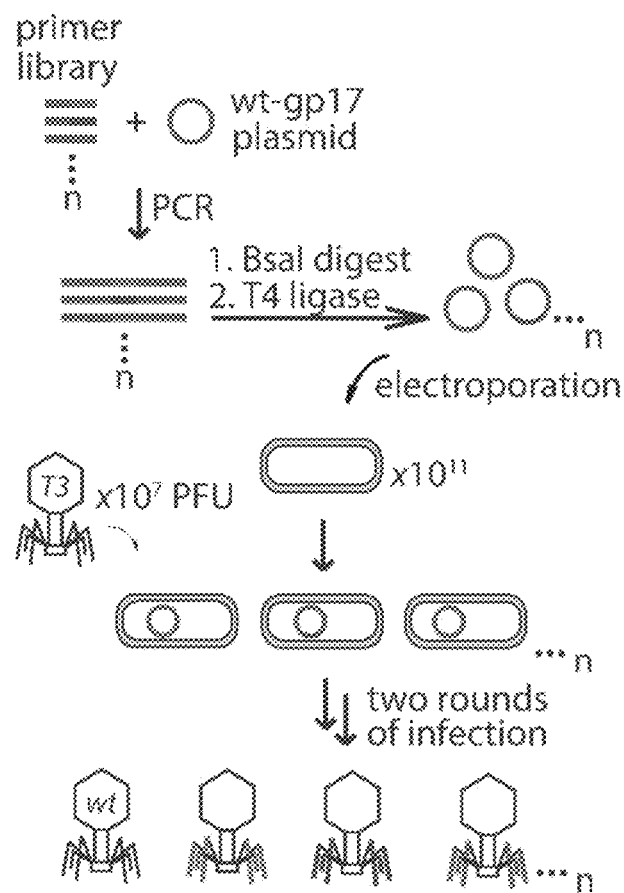
FIG. 17. Schematic illustrating the restriction-ligation method to synthesize phage libraries.

Restriction-Ligation-Based Method:

For each loop library, ten 25 uL PCR reactions were carried out where 10 ng of template plasmid encoding the T3 gp17 gene was PCR amplified using 8 pmoles of each primer and 0.5 units of HiFi polymerase following the heating protocol summarized in TABLE 1B. Primers were designed to encode a (1) mutagenized region corresponding to the desired gp17 loop and (2) BsaI cleavage sites for restriction digestion and subsequent circular ligation by T4 ligase to yield scarless circular plasmids (FIG. 17 and FIG. 23A). The mutagenized region was encoded by NNK codons to minimize premature incorporation of stop codons.

TABLE 1B

| Step | Temp. | Time |
|---|---|---|
| 1 | 95° C. | 3 min |
| 2 | 98° C. | 15 s |
| 3 | 62° C. | 15 s |
| 4 | 72° C. | 2 min |
| Repeat 2-4 25 times | | |
| 5 | 72° C. | 10 min |

Each PCR reaction yielded approximately 500 ng of linear PCR product, which was pooled together and DpnI (100 units) treated for 4 hours at 37° C. to eliminate template plasmid. Following DpnI digestion, the PCR products were purified using Zymo DNA clean and Concentrator™-5 spin columns. Next, ~5 μg of linearized gp17 gene products were diluted in New England Biolabs CutSmart® buffer (500 μL) and restriction digested using 125 units of BsaI at 37° C. for four hours, after which the enzyme was heat inactivated at 65° C. for 20 minutes. Digested DNA was purified using Zymo DNA clean and Concentrator™-5 spin columns and eluted in Nanopure water (18.2 Me).

The digested DNA was circularized using T4 ligase, where 2 μg of DNA was diluted to 500 μL in T4 ligase buffer, which 10 μL of T4 ligase (4,000 units) was added and the reaction was incubated overnight at room temperature. The next day, DNA was purified using the Zymo DNA clean and Concentrator™-5 spin columns and eluted with 7 μL of Nanopure water to yield a plasmid stock of ~100 ng/uL. Next, bacterial libraries were made by transforming 100 ng of plasmid into New England Biolabs 5-alpha electrocompetent cells via electroporation (1 mm cuvette, 1.7 kV, 200 52, and 20 μF). The bacteria recovered for 1 hour at 37° C. in SOC media (1 mL), after which the transformation yield was determined by plating serial dilutions of culture on LB-kanamycin agar plates. The 1 mL bacterial cultures were then diluted with 9 mL of LB-kanamycin and grown overnight at 37° C. and 250 rpm. The next day, new cultures were started by diluting 1 mL of overnight culture into 9 mL of LB, which the remaining culture was pelleted and stored at −20° C. for sequencing. Phage lysates were made by infecting bacterial cultures at exponential growth phase ($OD_{600}$: 0.7) with $10^7$ plaque forming units (PFU) of T3 (100 μL). The cultures were grown for another 2-3 hours until the cultures cleared. Phage lysates were chloroform treated with 500 mL of chloroform for 30 minutes to extract the cellular debris and kill any remaining bacteria. Phage lysates were spun down at 7,000 G for 5 minutes and stored at 8° C. for long-term storage.

Tail Fiber Structure Modelling and Display

The structure of T3 gp17 was modelled using Swiss-model at its default settings (Arnold et al., Bioinformatics 22, 195-201 (2006)), and the results were analyzed and visualizations were created using the chimera software.

Measuring Efficiency of Plating (EOP) of Phage Lysates

Lysate's host range was characterize through EOP measurements. Phagebody libraries were serially diluted in triplicates and 3 µl of each dilution were spotted onto the surface of 10×10 cm LB agar plates covered with a top agar lawn of the desired test strain. The EOP was calculated as the ratio between the phage titer on the mutant strain and the reference strain, which was $E.$ $coli$ BL21. The confidence interval of the calculated EOP was computed using the method described in (Fieller, Suppl. To J. R. Stat. Soc., 1-64 (1940)) using the calculator located at www.graphpad.com/quickcalcs/ErrorProp1.cfm.

Phage Panning

Figure 16A:
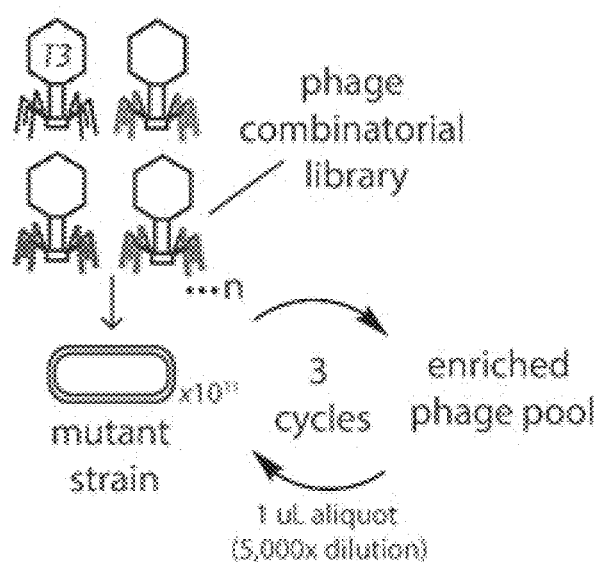
FIGS. 16A-16B.
Figure 16B:
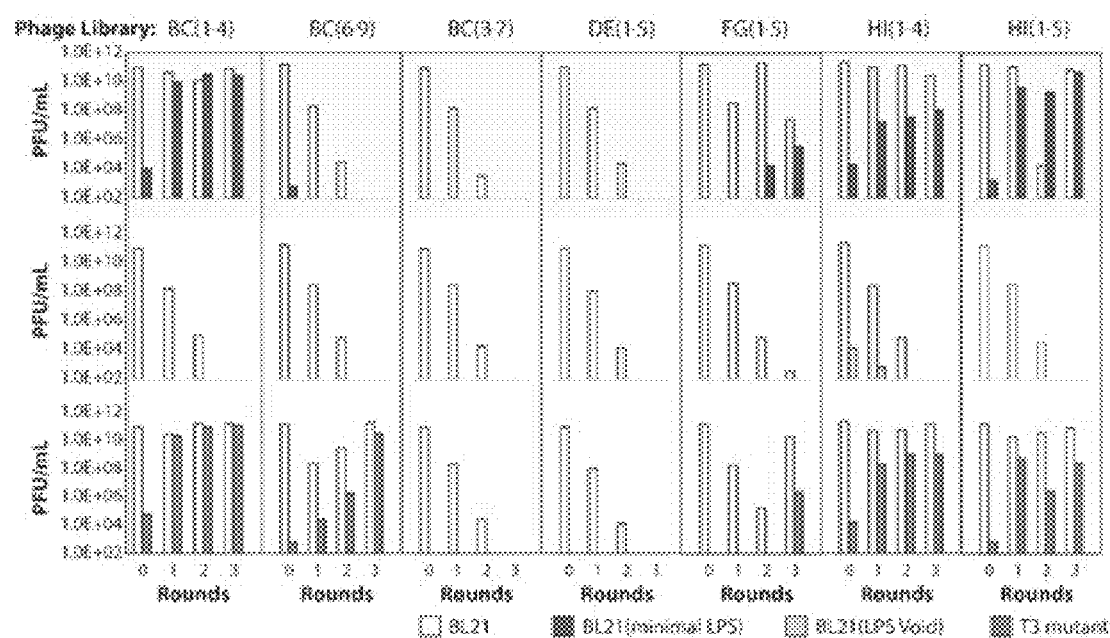

For each bacterial mutant, overnight cultures were grown from a single colony. The next day, 50 µL of the overnight culture was diluted into 5.0 mL of LB and grown to exponential phase ($OD_{600}$: 0.7), which point 100 uL of phage lysate from each loop library was added. The bacterial cultures were grown for another 3 hours, except for ΔwaaC mutants, where the culture was grown for 4 hours. After phage propagation, phage lysates were chloroform treated (250 µL), spun down at 7,000 G for 5 minutes, and stored at 8° C. for subsequent panning. This procedure was repeated for additional rounds (FIG. 16A and FIG. 30A), except infecting with 1 uL of phage lysate from the previous round of infection rather than 100 µL, except for ΔwaaC where 100 µL was added. This enabled amplification of functional phages, while diluting away phages incapable of infecting bacterial mutants.

Resistance Index Determination

Triplicate samples of ~$10^5$ PFU of each phagebody isolate was mixed with ~$10^9$ CFU of wild-type $E.$ $coli$ BL21 in 3 ml of top agar and immediately poured over an LB plate. After the top agar had hardened, plates were incubated for 24 hrs at 37° C. CFU were subsequently counted for each plate. Because it is unlikely that two independent BL21 cultures contain the exact same assortment of naturally occurring mutation, results were systematically normalized to the number of CFU counted on T3-infected lawns. A pseudo-count of 1 was added to the entire dataset prior to any calculation. The confidence interval on the resulting resistance indices was calculated according to (Fieller, Suppl. To J. R. Stat. Soc., 1-64 (1940)) using the calculator located at www.graphpad.com/quickcalcs/ErrorProp1.cfm.

Liquid Culture Assay for Resistance Suppression by Phagebody Libraries

From an overnight culture of wild-type BL21, a fresh culture was grown to exponential phase ($OD_{600}$=0.7). After which, 250 µL aliquots of the culture were added to a 96 well plate along with 2.5 uL of phagebody lysates per well. This equates to an MOI of 0.001. Growth curves were obtained by taking $OD_{600}$ measurements using a BioTek Synergy H1 microplate reader at 2 min. intervals, 37° C., and constant shaking.

Liquid Culture Assay for Resistance Suppression by Phagebody Cocktail

Overnight cultures of BL21 were grown from a single colony. The next day, 500 µL of the overnight cultures were diluted into 50 mL of LB in 250 Erlenmeyer flasks and grown to exponential phase ($OD_{600}$: 0.7). After which, ~$10^7$ PFU's (which equates to a multiplicity of infection of $10^{-3}$) of phage lysate from wild type T3 (100 µL) or a phage cocktail (10 µL) were added. The cultures were grown overnight. The next day, 1 mL aliquots were taken from each culture and washed 4 times in PBS and were serial diluted and plated on LB-agar plates to quantify the amount of colony-forming units (CFU). Every 24 hours, 25 mL of the culture was discarded and diluted with 25 mL of 2×-concentrated LB to ensure bacterial nutrients were still available.

Liquid Culture Assay for Resistance Suppression by Isolated Phagebodies

T3 and the phagebodies T3(HI:ASRV), T3(HI:GARV), T3(BC:AAGKNALGG), T3(HI:HSQP), T3(HI:HSVV), T3(HI:NCHV) and T3(HI:RTFI) were each seeded at an MOI of ~$10^{-4}$ into 4 replicate 10 ml LB late log phase $E.$ $coli$ BL21 cultures. The cultures were then incubated at 37° C. with shaking at 250 rpm for 22 hrs. Each culture was subcultured into 10 ml LB medium with a 100-fold dilution and the process was repeated over 6 days. Prior to starting the experiment and before every reseed, the bacterial and phage titers were measured. Phage titer was measured not only on the original host $E.$ $coli$ BL21 but also on the two LPS mutants ΔwaaC and ΔwaaG. In order to mitigate the effect of phages on colony viability during plating and counting, 1 ml samples from each condition were washed 3-times in PBS before serial dilution and plating. PFUs were measured from the chloroform-treated supernatant of the first wash.

Additional Cloning Approaches

Variability was generated in the tip of T3 gp17 in several ways: a) primer based randomization of multiple loops; b) primer based randomization of single or multiple loops; and c) random mutagenesis of the whole tip module using base analogs. In all cases, all or fragments of the T3 17 gene were cloned into a plasmid which is introduced into phage susceptible strains ($E.$ $coli$ DH5a or DH10B derivatives). This bank was then infected with the wild-type phage and the resulting population screened for viruses infecting other types of bacteria. Deletion of xonA (sbcB) and recJ (strain FSL71) stimulates recombination of plasmids with T7 or T3 by a factor of 2 to 3-fold. The strain harboring these deletion has a very low transformability and the recombination benefit was therefore shadowed by the low transformation efficiency and such a mutant was not systematically used in experiments. It also was found that introduction of plasmids containing a CRISPR-cas9 system targeting the T3 17 tip sequence (pACY22) could improve recombination efficiency but the benefits of counter selecting against WT 17 was not reproducible enough to warrant the lower transformation efficiency incurred by the presence of the extra plasmid carrying the CRISPR-cas9 system.

TABLE 2

Primers used for construct preparation.

| | | SEQ ID NO: |
|---|---|---|
| pSLM49 construction | | |
| PST480 | GTACGAATTCAGCTGGATCCAGACCTAGGGGATATATTCCGCTTCCTCGCTCA | 1 |
| PST481 | GCATCCCGGGTGCAAAGCTTGACGTCGGAATTGCCAGCTGGGGCGCCCTC | 2 |

TABLE 2-continued

Primers used for construct preparation.

| | | SEQ ID NO: |
|---|---|---|
| PST575 | TAGCGGATCCTGAAGGAACGTGACCCAAACAAACCGTACA | 3 |
| PST576 | TCGACCCGGGATCTTATCGACTACCTTGGCACCAATCTGA | 4 |

Subcloning phagebody tips into pSLM49

| | | |
|---|---|---|
| PS1691 | GTACTAAGTGGGGAGGTAAGTGGCTT | 5 |
| PS1692 | GTGTGATAGTCCATCCGTGGACTTAAAGTA | 6 |
| PST693 | AAGCCACTTACCTCCCCACTTAGTAC | 7 |
| PST694 | TACTTTAAGTCCACGGATGGACTATCACAC | 8 | pSLM173 construction

| | | |
|---|---|---|
| PST1089 | GGTACCTTTCTCCTCTITAATAGCTAAATC | 9 |
| PST1090 | GTGCACGGATCCCATGGTACGCGTGCTAG | 10 |
| PST1091 BL | GGAGAAAGGTACCATGTCATTTTGTTGGAATGAAATTAATTCTGG | 11 |
| PST1092 BL | GGGATCCGTGCACTTATTTATCTAATAAACATTGGTCTGATTGTGC | 12 | pSLM111alpha construction

| | | |
|---|---|---|
| PST816 | CCTGTGGGGCCCATGCCCTAGGTCATGAGATTATCAAAAAGGATCTTCACC | 13 |
| PST817 | GGTGCAGGGCCCTCGACAATTGTCAGCCAATCGACTGGCGAGCGGCATCGC | 14 |
| PST818 | TGCGAAGGGCCCGGATTCGAATTCGTGATCTTCCGTCACAGGTAGGCGC | 15 |
| PST819 | GTGGCAGGGCCCGCGTAAGCTAGCGGCGCGCCATTTAAATGAAGTTCCTATTCC | 16 | waaC deletion

| | | |
|---|---|---|
| PST853 | CGGATGCGGGTTTTGATCGTTAAAACATCGTCGATGGGCGGTGTAGGCTGGAGCTGCTTC | 17 |
| PST854 | ACCATCTGATTCITCCCATACCCACCAATTAATCCCGGATATGGGAATTAGCCATGGTCC | 18 | waaG deletion

| | | |
|---|---|---|
| PST857 | CGGTTTGCAGCGCGATTTTATGCGTATTGCTCAGACAGTCGTGTAGGCTGGAGCTGCTTC | 19 |
| PST858 | CCAGACCACCCGTTATGATATCCGCCGCTTTCTCTGGCAGATGGGAATTAGCCATGGTCC | 20 |

| direct transformation loop library construction | | loop modification | |
|---|---|---|---|
| PST695 | CCTGTGGGAGAGTATCAGTCTGAGAACCMNNMNNMNNMNNMNNMNNMNNMNNMNNAGCCCATACTTGAGTCCAGGCC | BC FW | 21 |
| PST696 | GGTTCTCAGACTGATACTCTCCCACAGG | BC RV | 22 |
| PST699 | GGCAGGGTATTTAAGAACATAGCGGATAGANNKNNKNNKNNKACAGCAATAGCCGTAGAGGACGTG | HI FW | 23 |
| PST700 | TCTATCCGCTATGTTCTTAAATACCCTGCC | HI RV | 24 |
| PST701 | AACTGGTCCTGACGGTATCTACTTCGTNNKNNKNNKNNKNNKTGGCATTCCAGATACACTCTAATCTGC | FG FW | 25 |
| PST702 | AAGGAAGTAGATACCGTCAGGACCAGTT | FG RV | 26 |
| PST794 | CTTAATCCATATGTTGCGGAATCGC | DE FW | 27 |
| PST795 | GCGATTCCGCAACATATGGATTAAGNNKNNKNNKNNKNNKTGGAACTTCTTCCGAACTGGTCCTGACG | DE RV | 28 |
| PST800 | GACAATGGCCTGGACTCAAGTATGGGCTNNKNNKNNKNNKNNKNNKNNKNNKNNKNNKGGTTCTCAGACTGATACTCTCCCAC | BC[10] FW | 29 |
| PST802 | AGCCCATACTTGAGTCCAGGCCATTGTC | BC[10] RV | 30 |
| PST803 | GGGTATTTAAGAACATAGCGGATAGANNKNNKNNKNNKNNKNNKACAGCAATAGCCGTAGAGGACGTG | HI[+3] FW | 31 |
| PST805 | TCTATCCGCTATGTTCTTAAATACCC | HI[+3] RV | 32 |
| PST696 | GGTTCTCAGACTGATACTCTCCCACAGG | partial BC FW | 33 |
| PST1252 | CCTGTGGGAGAGTATCAGTCTGAGAACCMNNMNNMNNMNNACTACCACTAGCAGCAGCCCATACTTGAGTCCAGGCC | BC[6-9] RV | 34 |
| PST1253 | CCTGTGGGAGAGTATCAGTCTGAGAACCTCCTCCCATGTAACTMNNMNNMNNMNNAGCCCATACTTGAGTCCAGGCC | BC[3-7] RV | 35 |
| PST1254 | CCTGTGGGAGAGTATCAGTCTGAGAACCTCCTCCMNNMNNMNNMNNMNNAGCAGCAGCCCATACTTGAGTCCAGGCC | BC[1-4] RV | 36 |

| BsaI/religation loop library construction | | loop modification | |
|---|---|---|---|
| PST1255 | CTGACTGGTCTCtAGCCMNNMNNMNNMNNACTACCACTAGCAGCAGCCCATACTTGAGTCCAGGCCATTGTC | BC[6-9] RV | 37 |

TABLE 2-continued

Primers used for construct preparation.

| | | | SEQ ID NO: |
|---|---|---|---|
| PST1256 | CTGACTtGGTCTCTAGCCTCCTCCCATGTAACTMNNMNNMNNMNNAGCCCATACTTGAGTCCAGGCCATTGTC | BC[3-7] RV | 38 |
| PST1257 | CTGACTGGTCTCAGCCTCCTCCMNNMNNMNNMNNMNNAGCAGCAGCCCATACTTGAGTCCAGGCCATTGTC | BC[1-4] RV | 39 |
| PST957 | AGTCAGGGTCTCTGGTTCTCAGACTGATACTCTCCCACAGG | BC FW | 40 |
| PST958 | CTGACTGGTCTCTATTCCAMNNMNNMNNMNNMNNCTTAATCCATATGTTGCGGAATCGC | DE RV | 41 |
| PST961 | AGTCAGGGTCTCTGAATTTCTTCCGAACTGGTCCTGACGGTATC | DE FW | 42 |
| PST962 | CTGACTGGTCTCTCAACCAMNNMNNMNNMNNMNNAAGGAAGTAGATACCGTCAGGACCAG | FG RV | 43 |
| PST965 | AGTCAGGGTCTCtTGGCTAAAATTCCAGATACACTCTAATGG | FG FW | 44 |
| PST966 | CTGACTGGTCTCTCGGTMNNMNNMNNMNNNTCTATCCGCTATGTTCTTAAATACCCTGC | HI RV | 45 |
| PST1258 | CTGACTGGTCTCTCGGTMNNMNNMNNMNNMNNNTCTATCCGCTATGTTCTTAAATACCCTGC | HI[+1] RV | 46 |
| PST969 | AGTCAGGGTCTCTACCGCAATAGCCGTAGAGGACGTG | HI FW | 47 |

TABLE 3

Plasmids constructed and used for this project

TABLE 2. List of oligonucleotides. FW: forward primer; RV: reverse primer.

| Plasmid Name | Features | Selection marker | Source |
|---|---|---|---|
| pSLM49 | wild-type T3 gene 17 | Kanamycin | This study |
| pSLM193 | pSLM49 with 17 (HI:RDIRLSI) | Kanamycin | This study |
| pSLM194 | pSLM49 with 17 (HI:ASRV) | Kanamycin | This study |
| pSLM195 | pSLM49 with 17 (HI:GARV) | Kanamycin | This study |
| pSLM197 | pSLM49 with 17 (HI:KLNI) | Kanamycin | This study |
| pSLM225 | pSLM49 with 17 (BC:AAGKNLAGG) | Kanamycin | This study |
| pSLM226 | pSLM49 with 17 (BC:MHGKSYMGGA524T) | Kanamycin | This study |
| pSLM227 | pSLM49 with 17 (BC:AIGRSHLKS) | Kanamycin | This study |
| pSLM228 | pSLM49 with 17 (HI:RFFV) | Kanamycin | This study |
| pSLM229 | pSLM49 with 17 (HI:HTHP) | Kanamycin | This study |
| pSLM230 | pSLM49 with 17 (HI:NCHV) | Kanamycin | This study |
| pSLM233 | pSLM49 with 17 (A524G HI:HTHP) | Kanamycin | This study |
| pSLD18 | heat sensitive and heat inducible recombineering plasmid | Erythromycin | This study |
| pSLM111 | suicide plasmid (pir dependent replication origin) with an FRT site surrounded apramycin marker | Carbenicillin, apramycin | This study |

Example 1: Host Range-Changing Mutations Cluster within Outward Facing Loops

Figure 11:
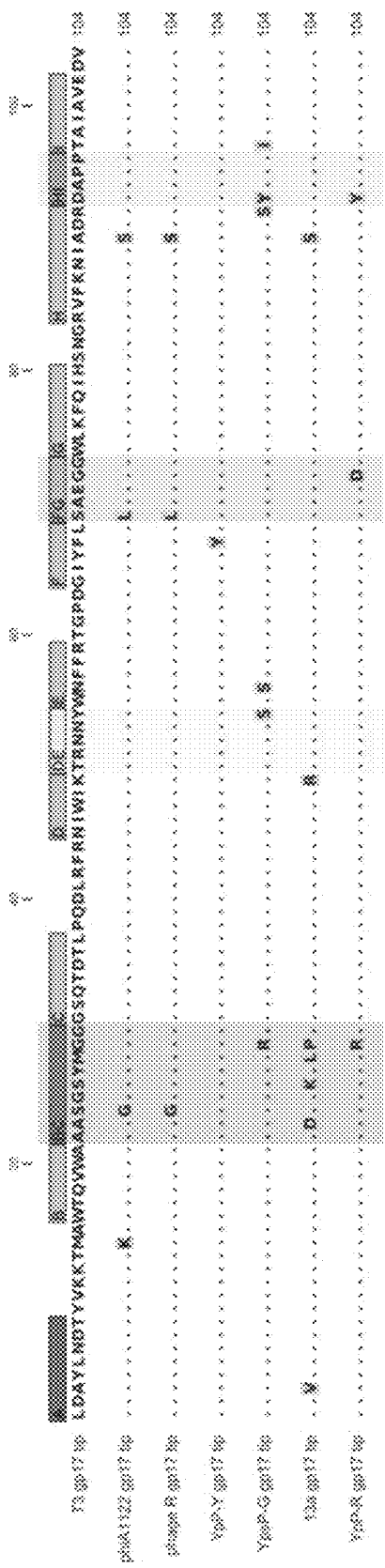
FIG. 11. Alignment of the closest homologs to the T3 gp17 tip (top to bottom: SEQ ID NOs: 170-176). Identical residues are displayed as dots. The location of loops BC, DE, FG and HI are highlighted.

Based on the T3 gp17 tip structure model and sequence alignments between T3 and T7 tail fibers, the location of its beta-strands and loops was defined (FIG. 2A). Alignment of the T3 gp17 tip sequences with its closest homologues shows that mutations are particularly enriched within the loop sequences (FIG. 11). The three point mutations found in phage R's gp17 are responsible for its capacity to infect *Yersinia pseudotuberculosis* (Ando et al. Cell Syst. 1, 187-196 (2015)) and suggests that the loop mutations observed in the other *Yersinia* infecting phages are equally responsible for the host range shift, furthering the hypothesis that loops are particularly important to host range determination.

T3 is naturally incapable of infecting *E. coli* MG1655 but evolves easily to do so. This characteristic was used as a way to select for naturally occurring mutants of T3 with altered host range in order to study the sequence variation within gene 17. Out of 66 such mutants individually picked and sequenced, 25 had mutations in BC and 25 in HI, 2 had a single mutation in the H or I beta-sheet while the 14 others had multiple mutations but all located within the tip region (TABLE 4).

A similar smaller experiment using BL21 ΔwaaC as a selective host yielded 3 independent phage variants capable of reproducing on it. The gp17 tip of these mutants was sequenced. Two were identical but the three impacted the same HI loop residue, D547 (TABLE 4).

TABLE 4

| Mutations identified in the T3 gp17 tip region that are associated with the ability to infect the indicated host.<br>New T3 host | Structure affected | mutation | number of occurrences |
|---|---|---|---|
| *E. coli* MG1655 | BC loop | S480R<br>Y481H | 24 |
| *E. coli* MG1655 | HI loop | D547Y | 12 |

TABLE 4-continued

Mutations identified in the T3 gp17 tip region that are associated with the ability to infect the indicated host.

| New T3 host | Structure affected | mutation | number of occurrences |
|---|---|---|---|
| E. coli MG1655 | HI loop | D547G | 10 |
| E. coli MG1655 | HI loop | D547A | 2 |
| E. coli MG1655 | I β-sheet | Frameshift from T550 | 4 |
| E. coli MG1655 | HI loop and I β-sheet | Frameshift from R546 | 1 |
| E. coli MG1655 | BC loop | G484K | 1 |
| E. coli MG1655 | H β-sheet | V539G | 1 |
| E. coli MG1655 | BC loop | S480I | 1 |
| MG1655 | multiple mutations: BC loop, H β-sheet, HI loop and/or I β-sheet | | 10 |
| BL21 LPS mutant | HI loop | D547G | 1 |
| BL21 LPS mutant | HI loop | D547N | 2 |

Example 2: Mutational Loop Library Design

T7 and T3 recombine very efficiently with plasmids that harbor at least 30-40 bp homology to their genomes (Bull et al. J. Mol. Evol. 53, 47-54 (2001); Bull and Molineux, Heredity (Edinb) 100, 453-63 (2008); Springman et al. G3 (Bethesda). 2, 825-30 (2012)), mutations introduced into plasmids can be transferred to the phage relatively easily, as long as they are selectable.

Figure 12:
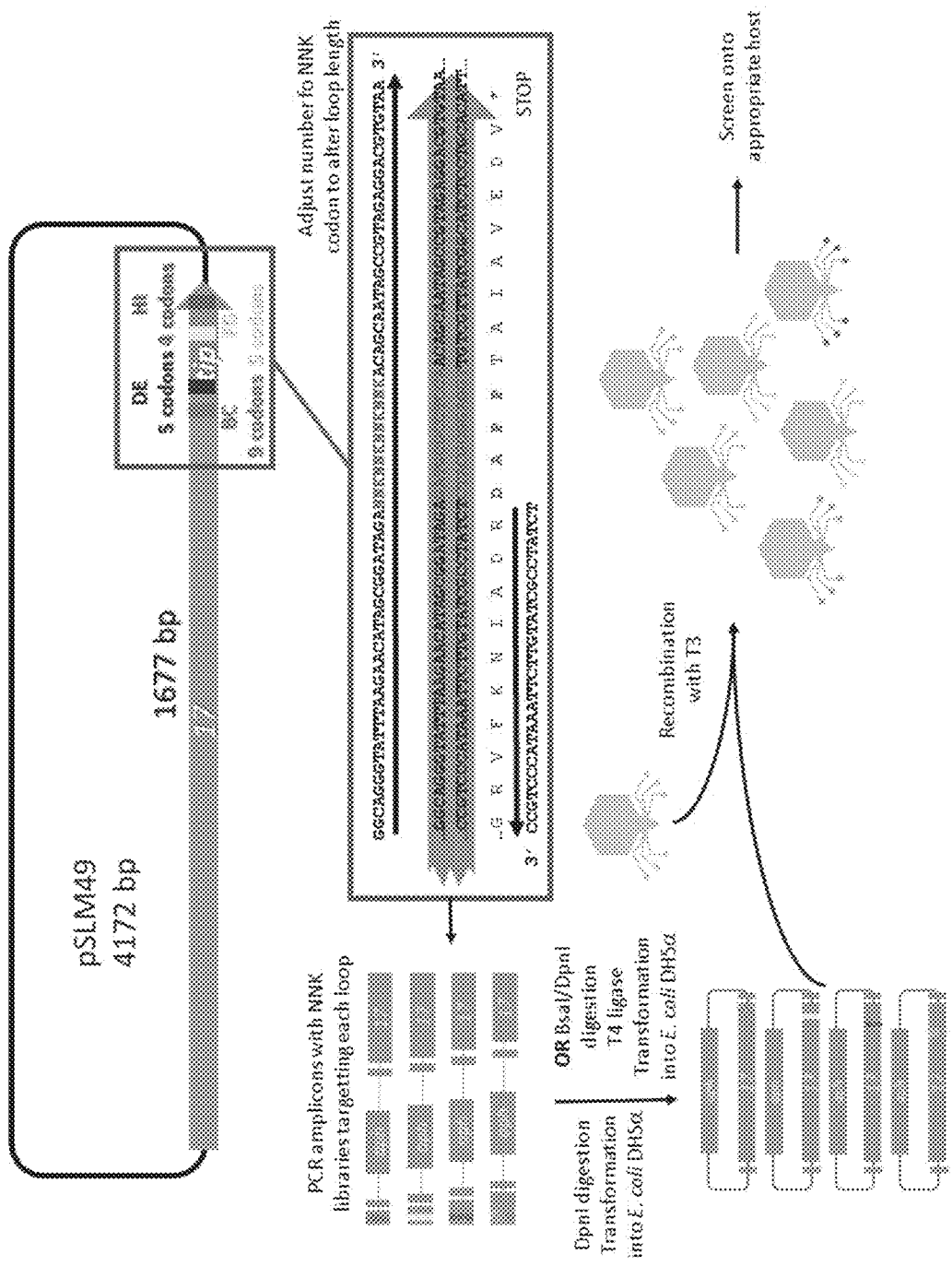
FIG. 12. Schematic of scheme for replacement of each codon within any given loop with the degenerate codon NNK GGCAGGGTATTTAAGAACATAGCGGATA-GANNKNNKNNKNNKACAGCAATAGC CGTAGAG-GACGTGTAA (SEQ ID NO: 177); GGCAGGGTATT-TAAGAACATAGCGGATAGAGATGCGCCTCCACAGC AATAGCCG TAGAGGACGTGTAA (SEQ ID NO: 178) (and reverse complement); CCGTCCCATAAATTCTTG-TATCGCCTATCT (SEQ ID NO: 179); GRVFKNIADRDAPPTAIAVEDV (SEQ ID NO: 180).

In order to generate as much diversity as possible within the loops, each codon was replaced within any given loop with the degenerate codon NNK (see material and methods for details; FIG. 12). This allows covering all possible amino acids while removing two of the three possible stop codons. The sequence space generated by such a randomization scheme is determined by the size of the targeted loop. Given the size of each loop, HI is four codons long, DE and FG five are codons long, and BC is nine codons long; only loops HI, DE and FG could be expected to be exhaustively queried (TABLE 5). As a result, the BC loop also was split into smaller sub regions (aa 1-4, 3-7 and 6-9) for which banks were made. Finally, libraries were created where the BC or HI loops were elongated by one or three codons to assess whether changing the length of a loop can impact host range.

TABLE 5

Theoretical genetic and protein diversity generated by NNK codons as a function of the number of codon randomized.

| loop length (aa) | theoretical DNA diversity with NNK codons | Theoretical protein diversity |
|---|---|---|
| 1 | 32 | 20 |
| 2 | 1024 | 400 |
| 3 | 32768 | 8000 |
| 4 | 1.0E+06 | 1.6E+05 |
| 5 | 3.4E+07 | 3.2E+06 |
| 6 | 1.1E+09 | 6.4E+07 |
| 7 | 3.4E+10 | 1.3E+09 |
| 8 | 1.1E+12 | 2.6E+10 |
| 9 | 3.5E+13 | 5.1E+11 |
| 10 | 1.1E+15 | 1.0E+13 |

TABLE 6

Cumulative characteristics of phagebody libraries made during this work. The theoretical diversity. The theoretical diversity expresses the total number of possible DNA combinations based on the number of NNK codons randomized. The cumulative coverage is the sum of the library transformation yields for all the libraries ever built for that loop. Calculated cumulative coverage is the percentage of the theoretical diversity created as measured by the total number of plasmid clones obtained for all repeats of each type of library. Hits are defined as obtaining at least one PFU on a lawn of the corresponding selective BL21 mutants, ΔwaaC, or ΔwaaG.

| Targeted loop | Theoretical diversity (number of different combinations from NNK codon randomization) | Number of libraries built | Cumulative coverage (% of theoretical diversity) | Number of phagebody libraries producing hits on ΔwaaC | Number of phagebody libraries producing hits on ΔwaaG |
|---|---|---|---|---|---|
| WT gp17 | NA | 21 | NA | 0 | 0 |
| BC | 3.5E+13 | 10 | ~0.0000005 | 4 | 7 |
| BC[1-4] | 1.0E+06 | 10 | ~60 | 4 | 6 |
| BC[3-7] | 3.4E+07 | 10 | ~90 | 2 | 5 |
| BC[6-9] | 1.0E+06 | 8 | >100 | 2 | 4 |
| DE | 3.4E+07 | 10 | ~50 | 2 | 4 |
| FG | 3.4E+07 | 10 | ~0.3 | 0 | 0 |
| HI | 1.0E+06 | 15 | >100 | 15 | 15 |
| HI[+1] | 3.4E+10 | 4 | ~0.00002 | 3 | 4 |
| HI[+3] | 3.4E+07 | 14 | ~20 | 10 | 10 |

Example 3: Testing the Capability of Loop Diversification

Given LPS mutants are the most likely pathway of resistance development against T3 infection, the phage banks were screened against two constructed LPS deletion mutants of E. coli BL21, ΔwaaG and ΔwaaC, to avoid the potential pleiotropic effects of naturally occurring T3 resistant mutants. A panel was assembled of 8 BL21 spontaneous T3 resistant mutants isolated from independent T3 infections and representative of the diversity of the evolutionary paths set in play during bacteriophage challenge.

Figure 3:
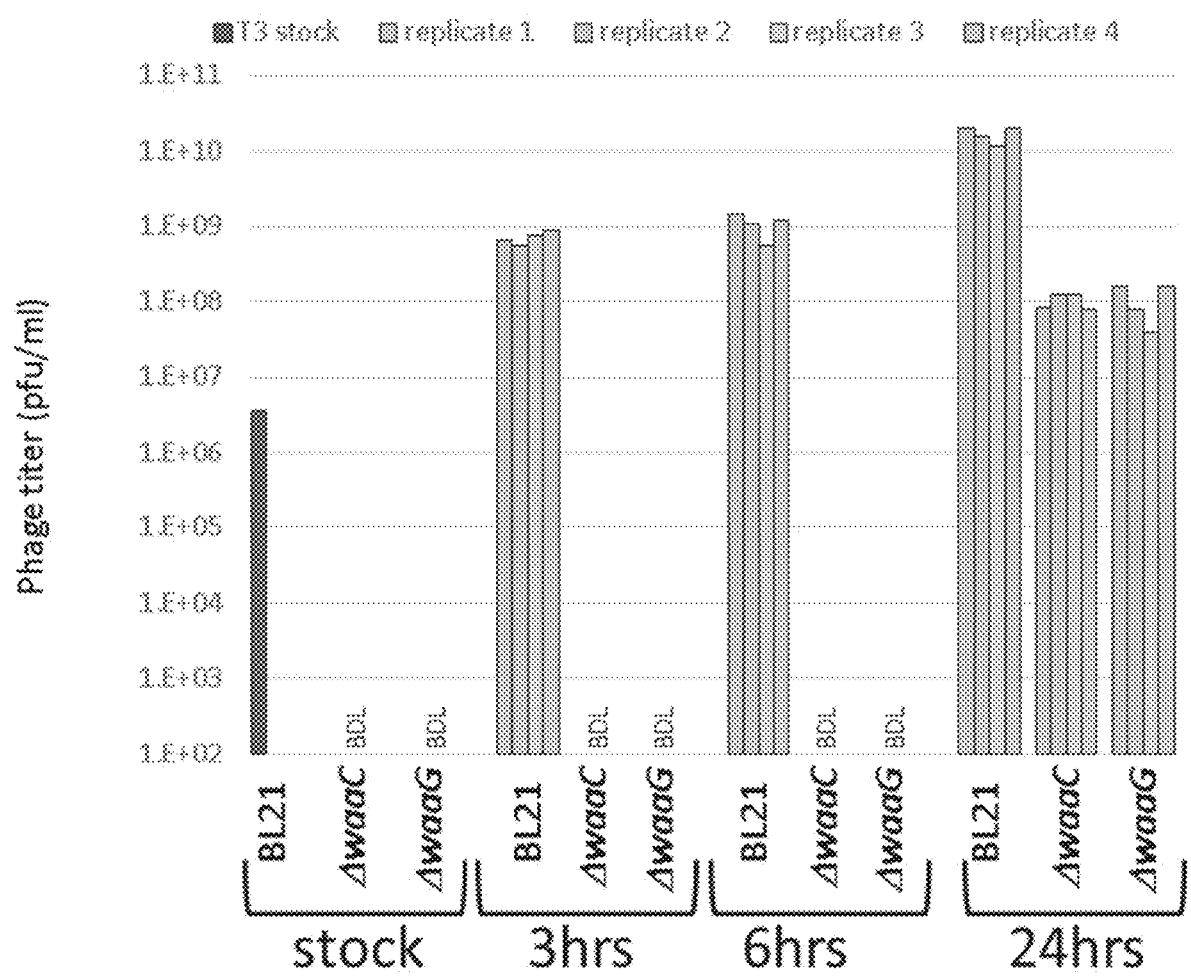
FIG. 3. T3 acquires LPS-mutant infectivity after extended incubation in batch cultures with E. coli BL21. Four independent late exponential cultures of E. coli BL21 were infected with T3 WT at an MOI~0.01 and the phage titers on WT E. coli BL21 and the two LPS mutants ΔwaaC and ΔwaaG followed along time of incubation. During the first day, samples from each culture were gathered at 3 hrs, 6 hrs and 24 hrs. The lysate were diluted 100-fold into fresh medium every 24 hrs. BDL: Below Detection Limit. For each time point, the set of bars, from left to right, represents: T3 stock, replicate 1, replicate 2, replicate 3, replicate 4.

The function of waaG was presented above but waaC was chosen as a second target because its mutant is stripped of its entire core LPS short of its two essential ketodeoxyoctulosonic acid moieties (KDO) (FIG. 1) and represents the absolute minimal LPS that bacteria can survive with under conditions relevant to natural systems (Klein et al. J. Biol. Chem. 284, 15369-89 (2009)). Both the ΔwaaG and ΔwaaC mutants of *E. coli* BL21 proved fully T3 resistant and naturally occurring mutations conferring infectivity to T3 were very rare (less than 1 in $10^{11}$ bacteriophages) only occurring after extensive co-culturing (>than 6 hours) of the phage and *E. coli* BL21 (FIG. 3). The 3' end of gene 17 of a few such mutants were sequenced and HI mutations were found similar to those described by previously: D547G, D547H or D547N (Perry et al. PLoS One 10, e0130639 (2015); Qimron et al. Proc. Natl. Acad. Sci. U.S.A. 103, 19039-44 (2006)).

Figure 4:
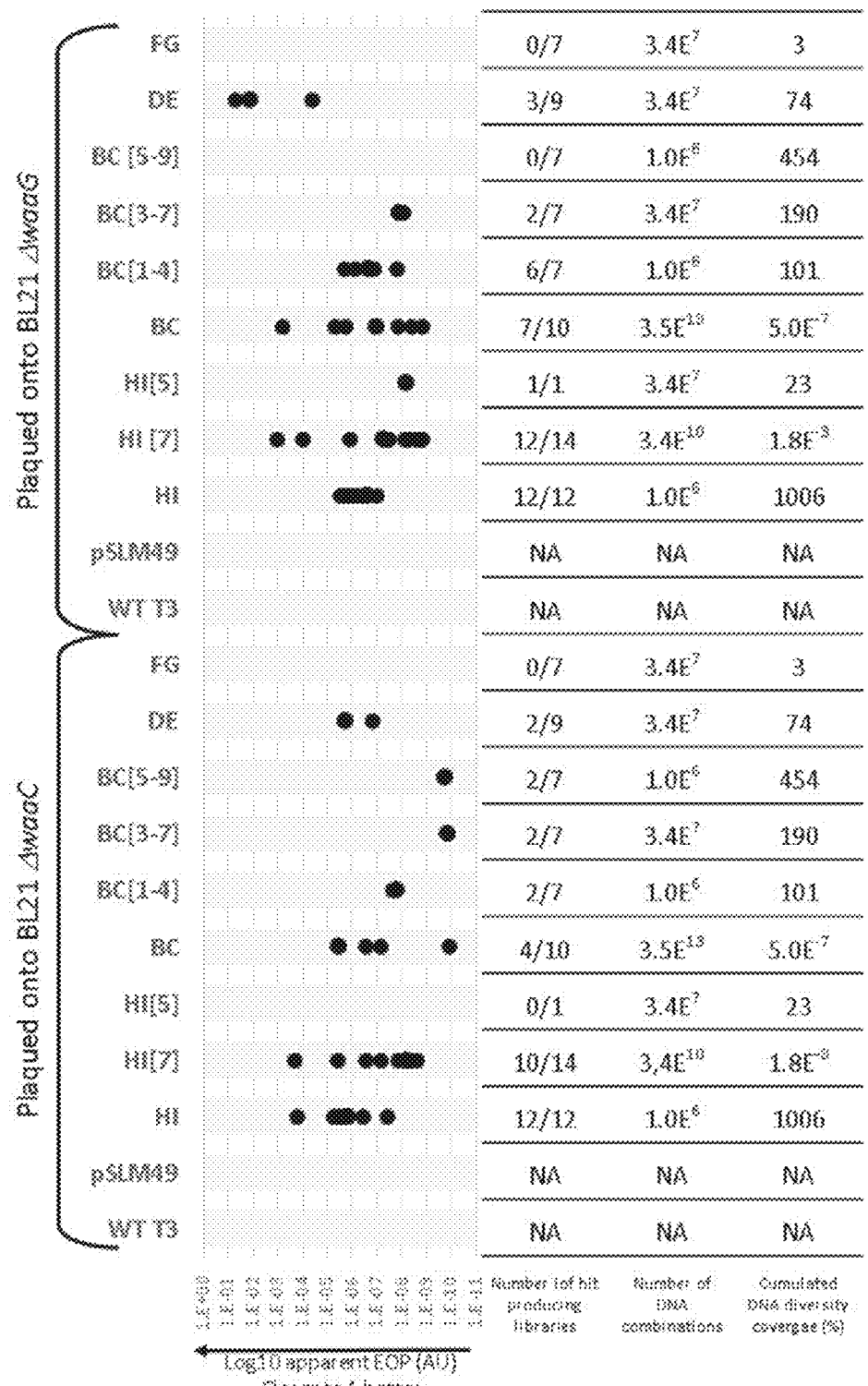
FIG. 4. Efficiency of Plating (EOP) of T3 lysates on two E. coli BL21 mutants, ΔwaaC and ΔwaaG. Lysates were grown on NEB5α carrying Gp17 plasmid libraries where independent loops were randomized, NEB5α with a non-mutated plasmid (pSLM49 or the normal T3 host, E. coli BL21 (T3 WT). Below the chart is the number of independent libraries that produced hits on either E. coli BL21 mutant and the theoretical cumulative percentage of the possible sequence space sampled for every type of loop modification. The theoretical coverage is calculated as the percentage of the possible diversity (4×4×2)n where n is the number of randomized codons in the remodeled loop with the assumption that libraries are completely independent and not redundant. NA: not applicable.
Figure 5A:
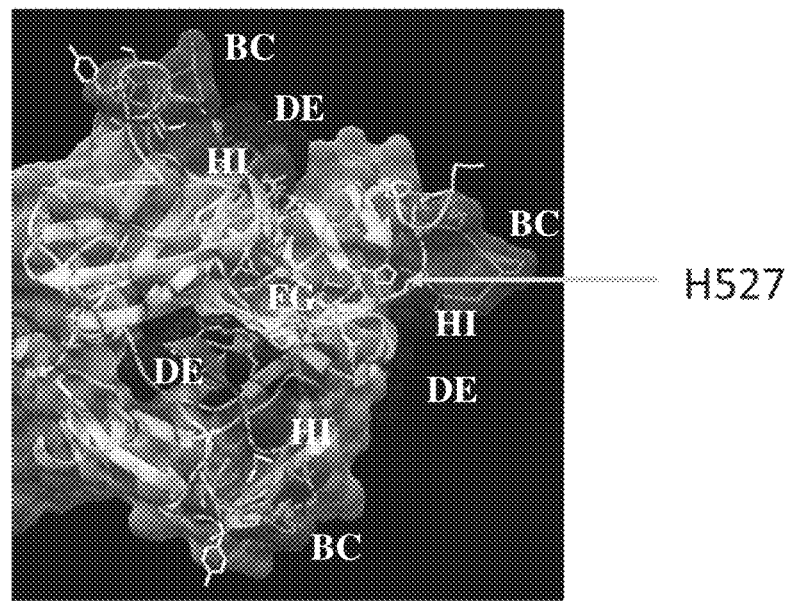
Figure 5B:
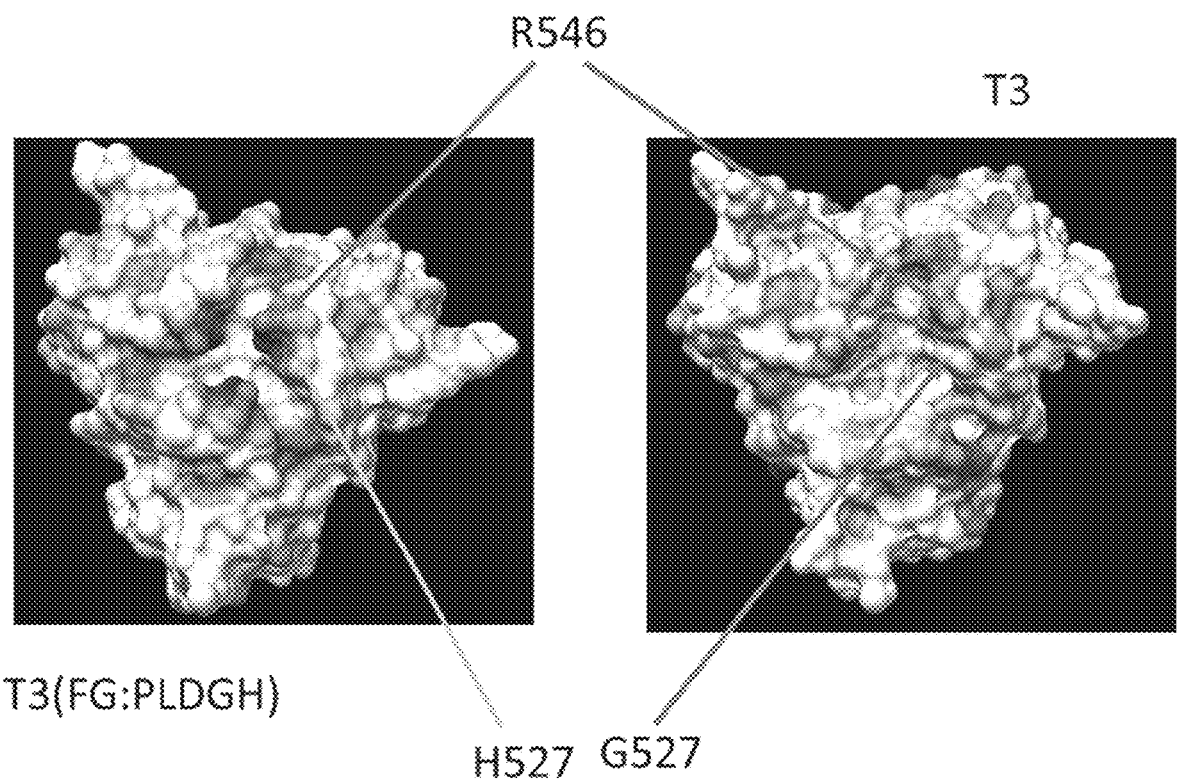

In order to sample as much diversity for each bank as possible, between 2 and 12 independent phage banks targeted at each of the BC, DE, FG and HI loops and their derivatives were generated and tested for their capacity to generate phages that plaque onto ΔwaaG and ΔwaaC. The result is expressed as the apparent efficiency of plating (EOP) of said bank which is the ratio of the phage titer on a test strain relative to the titer on the normal host, wild-type *E. coli* BL21. The results are plotted in FIG. 4. An apparent EOP close to 1 indicates that most viable phages in the lysate are equally capable at infecting WT BL21 as its LPS mutant(s). Each dot represents the apparent EOP of one plaque generating library. Given the fact some of the banks assessed had a very low diversity (~1000-$10^7$ different clones for a theoretical bank diversity), as can be expected from the low sequence coverage for some of the banks that were created, the results display stochasticity with some libraries targeting a given loop containing successful phages variants that can infect either or both test bacterial mutant while others do not with the exception of the HI targeting libraries that almost systematically contain successful mutants adsorbing to either LPS mutant (FIG. 5).

Example 4: Mutagenizing the DE or FG Loop does not Produce Many Host Range Altered Mutants Not all loops proved equal in participating in host range determination. As presented in FIG. 4, none of the libraries designed to target the FG loop generated detectable amounts of phages capable of targeting either test strain in the EOP assay. However, by co-culturing an FG bank with the ΔwaaG mutant repeatedly, one variant phage was obtained that was capable of reproducibly plaquing on it. The DE libraries also proved to have a poor yield of functional phage mutants, besides, none of the plaques picked from DE banks produced phages which grew robustly and they were eventually lost before they could be investigated any further. This suggested that the FG and DE loop might be more important to the structure of gp17 than initially envisaged.

Based on the modelled structure of T3 gp17, the DE loop residue side chains appear mostly surface accessible and display minimal contacts with other parts of the protein which would suggest that modifying it is unlikely to generate massive structural damage. A notable exception is T504 which is largely tucked underneath HI loops P548 and P549 and Y508 which stacks against I519 from the neighboring monomer while being pushed back by FG loop's E525. It is conceivable that by replacing one or both of these residues, the banks created a large fraction of inactive tail fiber mutants which contributes to the very low hit rate on either LPS mutants and general instability of the phages that did plaque on them (FIG. 13). As discussed above, E525 seems involved in an interaction with the DE loop tyrosine and while part of its side chain is surface exposed, its carboxyl group isn't hidden beneath DE loops N506 and N507 on the one hand and the neighboring gp17 monomer G beta strand's K530 side chain. E525 and K530 from the neighboring monomer are likely to be involved in a salt bridge which seems to be conserved in T7 gp17 structure although it is then operated by D520 and R525. This suggest an important structural role for those residues. A524's side chain is entirely buried inside the beta-sandwich structure and not accessible to the exterior solvent thus unlikely to have a great contribution to host range leaving only 5523, G526 and G527 as positions that may be mutated with limited risk.

In the only phagebody obtained from the FG libraries, T3(FG:PLDGH), the C-alpha trace of the FG loop is virtually indistinguishable from that of the WT gp17 protein despite a completely different primary structure highlighting the structural constraints exercised by the rest of the protein onto that sequence. To illustrate this, the average distance between the Ca residues of loop residues from aligned modelled T3 and T3(FG:PLDGH) tip domains was plotted (FIG. 5A). This shows that the BC loop undergoes tremendous remodeling in the phagebody compared to T3 but this loop is also intrinsically flexible due to its outward location whereas all residues of the FG loop are positioned less than half an Angstrom away between the two structures. The DE and HI loops are similarly conserved. FIG. 5B illustrates how the imidazole group of T3(FG:PLDGH)'s sticks out into the central crevice of the trimer by overlapping the computed surface of T3 gp17 trimer with the ribbon and side chain display of T3(FG:PLDGH)'s tail fiber model. This imidazole group makes a significant contribution to the electrostatic surface potential of T3(FG:PLDGH) compared to the wild-type protein (FIG. 5C) and may help the phage in making contact with the highly negatively charged KDO and/or phosphate residues residues at the very bottom of the LPS (FIG. 1). It is also interesting to see that an acidic residue was maintained at position 525 while an aliphatic one was selected at position 524 in light of the structural features described in the previous paragraph.

Example 5: The HI and BC Loops are Hot Spots for Host Range Determination

The two other loops, BC and particularly HI, proved extremely successful at generating host range altered phagebodies. At 9 aa, the BC loop is the longest of the 4 variable regions studied here. The amount of sequence diversity generated by NNK codons at each position largely exceeds library synthesis capability (~4×$10^{13}$ combinations at the DNA level, ~5×$10^{10}$ at the protein level) but successful hits were easily recorded despite a very minimal sequence coverage. Indeed, 4 out of 10 libraries generated ΔwaaC infecting variants and 7 out of 10 displayed ΔwaaG infectivity. Very surprisingly however, despite a 441% sequence space coverage, libraries targeted at the last 4 codons of the BC loop generated very few successful hits and only on ΔwaaC whereas the libraries aimed at randomizing the 4 first codons of that same loop generated hits on both target strains despite a much lower sequence space coverage. This is all the more puzzling that codons 6-9 of the BC loop are those most exposed to the basal side of the tail fiber tip and would therefore be expected to be heavily involved in host contact. The BC loop is also expected to be the most flexible part of the gp17 tip as it sits at the periphery of the structure and loop side chains appear largely free of interactions with the rest of the protein allowing them a great level of mobility.

Figure 14:
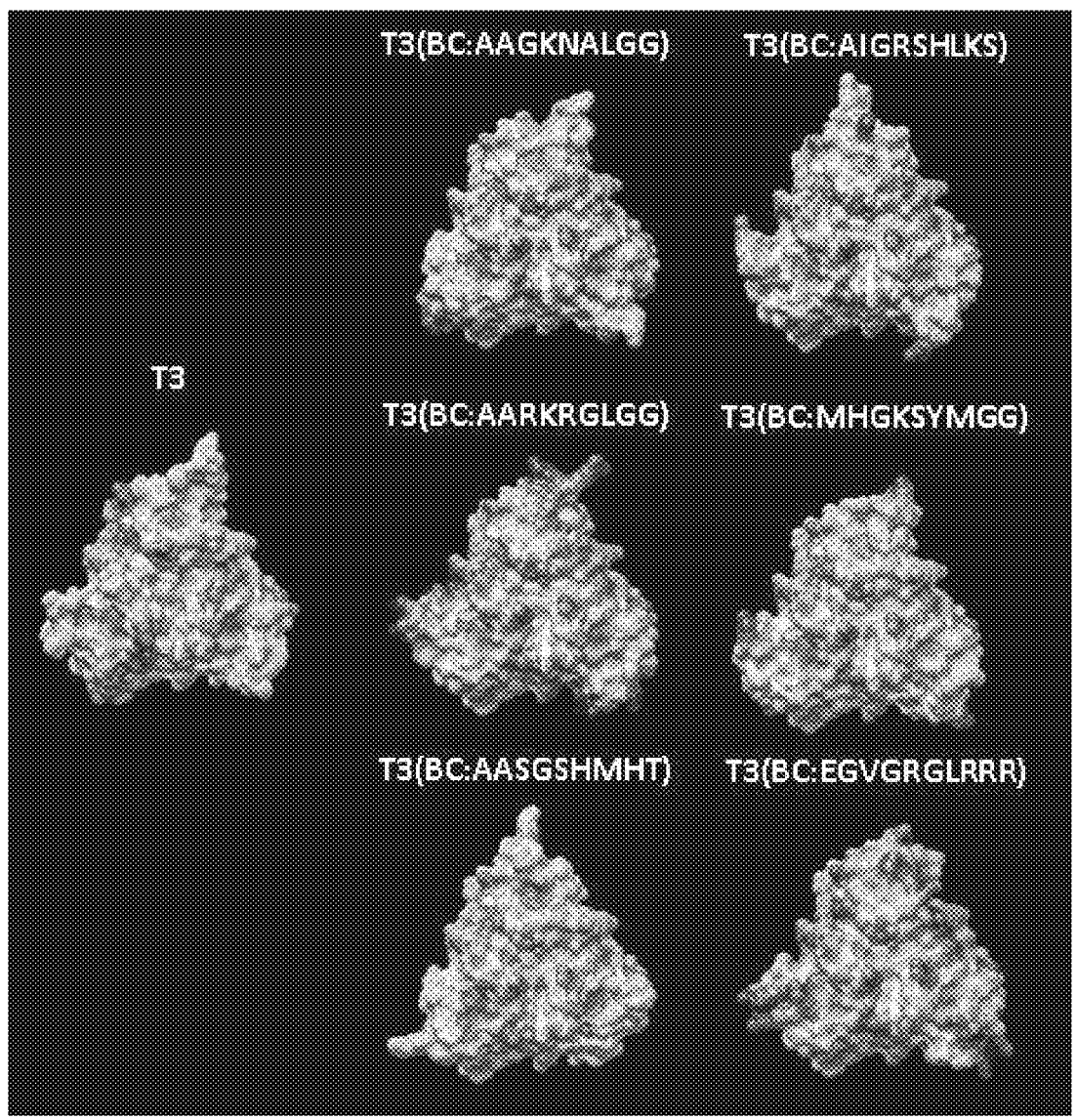
FIG. 14. Gp17 tip models from BC loop mutated phagebodies. Surface shaded according to electrostatic potential. White: neutral; Shaded: charged.

Experiments with the BC loop are a very good illustration of the usefulness of the approach which combines guided designs with empirical engineering strategies. Analyzing the sequence and structure of 7 phagebodies isolated from the various banks that were created did not reveal any clear structural rationale as to why they may have altered host recognition (TABLE 7). All mutants have positively charged amino acid within their mutations (R, K and/or H) but some of these residues appear not to change the electrostatic potential (FIG. 14) of the basal surface of the tail fiber as exemplified by T3(BC:AAGKNALGG) and T3(BC:AASGSHMHT), so it is unclear whether they are responsible for the host range change.

The HI loop at only 4 codons long is the one that was most exhaustively covered and because it was short to begin with, length was experimented with as well while maintaining libraries of sizes compatible with reasonably exhaustive screening (TABLE 6). HI targeting bank produced more hits more consistently than any other library. As for other LPS mutant infecting phagebodies, most mutants contain positively charged amino acids. Aligning all the mutants that were isolated and that have a normal length HI loop (4 codons) reveals that they sport positively charged amino acids at position 547 or 549 (FIG. 6A). Close inspection of the gp17 structures reveal that indeed, the entire surface contribution of the HI loop lies in residues 547 and 549 side chains (FIG. 6B) while 548 and 550 have their side chains buried inside the protein with no access to solvent. Once again it was hypothesized that the host range change stems from the positively charged amino acids helping to recognize negative charges (carboxylic acid on KDO or phosphate groups) in the lower LPS inner core.

Figure 7:
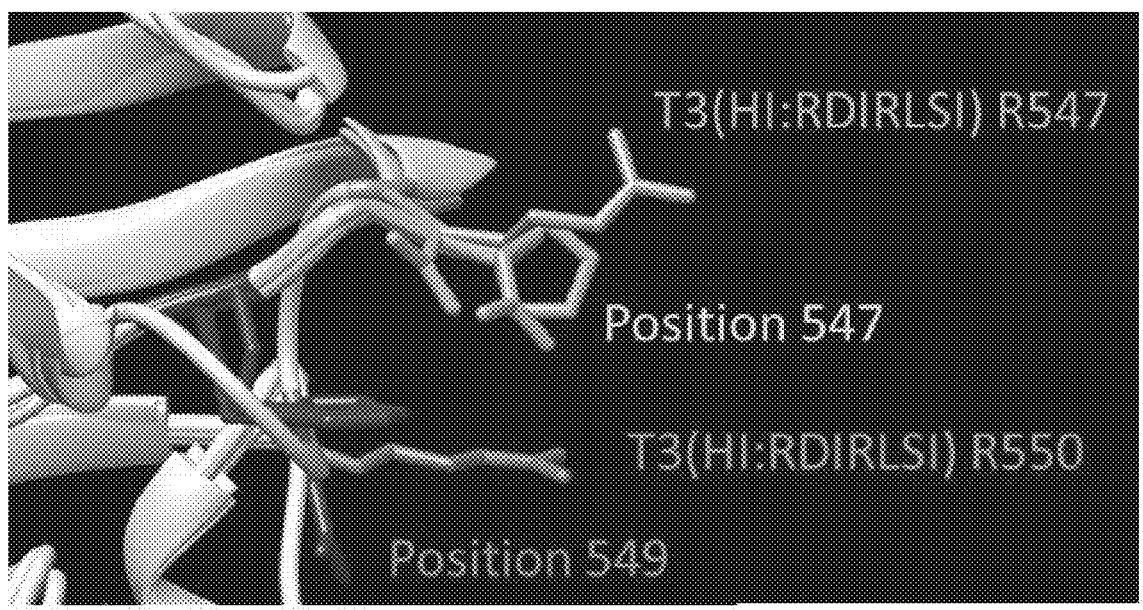
FIG. 7. Detail of the HI loops from 6 aa codon long HI phagebodies and T3(HI:RDIRLSI). The modelled structures of 7 phagebody gp17 tips with HI loop mutations were superimposed. Position 547 and 549 of the 6 phagebody with 4 codon long HI loops (ASRV, KLNI, HTHP, NCHV, RFFV and RTFI) are identified. T3(HI:RDIRLSI) R547 and R550 are also highlighted to show how similarly placed the side chains are.

T3(HI:RDIRLSR) is one of two phagebodies that have switched host range as opposed to expanded it and as a result a particularly interesting phage. Interestingly, the HI loop of this mutant took a much more helical conformation allowing the positioning of the two arginines in ways almost identical to the way positively charged side chains in other HI mutated phagebodies (FIG. 7) so it may be that the host range change emanates from the two arginines exacerbating the affinity towards negatively charged lower LPS.

TABLE 7

Phage strains constructed along this work with their known characteristics.

| Phagebody ID | Targeted loop | Loop DNA sequence | Loop protein sequence | Isolation method | Verified through recloning? | Part of coctail? |
|---|---|---|---|---|---|---|
| T3 | BC | GCTGCTAGTGGTAGTTACATGGGAGGAGGT (SEQ ID NO: 48) | AASGSYMGGG (SEQ ID NO: 76) | | | |
| T3 (BC:AAS GSHMHT) | BC | GCTGCTAGTGGTAGTCATATGCATACTGC (SEQ ID NO: 49) | AASGSHMHTG (SEQ ID NO: 77) | panning on D10 | | Yes |
| T3 (BC:AA GKNALGG) | BC + H | GCTGCTGTGTAAGAATGCGCTTGGAGGAGGT//C1631T (SEQ ID NO: 50) | AAGKNALGG//A544V (SEQ ID NO: 78) | direct plaque picking | Yes | |
| T3 (BC:AAR KRGLGG) | BC | GCTGCTAGGAAGCGGGGTCTGGGAGGAGGT (SEQ ID NO: 51) | AARKRGLGGG (SEQ ID NO: 79) | panning on D10 | | Yes |
| T3 (BC:MH GKSYMGG) | BC + FG | ATGCATGGTAAGAGTTACATGGGAGGAGGT//G1570A (SEQ ID NO: 52) | MHGKSYMGGG//A524T (SEQ ID NO: 80) | direct plaque picking | Yes | |
| T3 (BC:AIG RSHLKS) | BC | GCGATTGGTAGGTCTCATTTGAAGAGTGT (SEQ ID NO: 53) | AIGRSHLKSG (SEQ ID NO: 81) | direct plaque picking | | |
| T3 (HI:AAS GSKLRH) | BC | GCTGCTAGTGGTAGTAAGCTGAGGCATGC (SEQ ID NO: 54) | AASGSKLRHG (SEQ ID NO: 82) | panning on ΔwaaC | | Yes |
| T3 (HI:AAS GSHMHK) | BC | GCTGCTAGTGGTAGTCATATGCATACTCGC (SEQ ID NO: 55) | AASGSHMHKG (SEQ ID NO: 83) | panning on ΔwaaG | | Yes |
| T3 | FG | TCAGCCGAGGGCGGT (SEQ ID NO: 56) | SAEGG (SEQ ID NO: 84) | | | |
| T3 (FG:PLD GH) | FG | CCGTTGGATGGTCAT (SEQ ID NO: 57) | PLDGH (SEQ ID NO: 85) | panning on ΔwaaG and D10 | | yES |
| T3 | HI | AGAGATGCGCCTCCA--------ACA (SEQ ID NO: 580) | RDAPP---T (SEQ ID NO: 86) | | | |
| T3 (HI:GHL SL) | HI | AGACATGGGTTGTCTTG-----ACC (SEQ ID NO: 59) | RLGLAV--T (SEQ ID NO: 87) | panning on ΔwaaG | | Yes |
| T3 (HI:LGL AV) | HI | AGACTGGGGTCTTGCTGTT-----ACC (SEQ ID NO: 60) | RLGLAV--T (SEQ ID NO: 88) | panning on D10 | | Yes |
| T3 (HI:HSV V) | FG + HI | G1570A//AGACATTCGGTGGTT-------ACA (SEQ ID NO: 61) | A524T//RHSVV---T (SEQ ID NO: 89) | direct plaque picking | | |

TABLE 7-continued

Phage strains constructed along this work with their known characteristics.

| Phagebody ID | Targeted loop | Loop DNA sequence | Loop protein sequence | Isolation method | Verified through recloning? | Part of coctail? |
|---|---|---|---|---|---|---|
| T3 (HI:NCH V) | HI | AGAAATTGTCATGTG--------ACC (SEQ ID NO: 620) | RNCHV---T (SEQ ID NO: 90) | panning on D10 | Yes | Yes |
| T3 (HI:HTG I) | HI | AGACATACGGGTATT--------ACC (SEQ ID NO: 63) | RHTGI---T (SEQ ID NO: 91) | panning on ΔwaaG | | Yes |
| T3 (HI:AYA SP) | HI | AGAGCTTATGCGTCTCCA------ACA (SEQ ID NO: 64) | RAYASP--T (SEQ ID NO: 92) | direct plaque picking | | |
| T3 (HI:KSG V) | HI | AGAAAGAGTGGGGTG--------ACA (SEQ ID NO: 65) | RKSGV---T (SEQ ID NO: 93) | direct plaque picking | | |
| T3 (HI:R546 G KAGI) | HI | GGAAAGGCGGGGATT--------ACA (SEQ ID NO: 66) | GKAGI---T (SEQ ID NO: 94) | direct plaque picking | | |
| T3 (HI:HTH P) | HI | AGACATACTCATCCT--------ACC (SEQ ID NO: 67) | RHTHP---T (SEQ ID NO: 95) | panning on ΔwaaG | Yes | Yes |
| T3 (HI:HSQ P) | HI | AGACATTCTCAGCCG--------ACC (SEQ ID NO: 68) | RHSQP---T (SEQ ID NO: 96) | panning on D10 | | Yes |
| T3 (HI:KLN I) | HI | AGAAAGCTGAATATT--------ACA (SEQ ID NO: 69) | RKLNI---T (SEQ ID NO: 97) | direct plaque picking | Yes | |
| T3 (HI:GAR V) | HI | AGAGGGGCGAGGGTG--------ACA (SEQ ID NO: 70) | RGARV---T (SEQ ID NO: 98) | direct plaque picking | Yes | |
| T3 (HI:ASR V) | HI | AGAGCGAGTAGGGTG--------ACA (SEQ ID NO: 71) | RASRV---T (SEQ ID NO: 99) | direct plaque picking | Yes | |

TABLE 7-continued

Phage strains constructed along this work with their known characteristics.

| Phagebody ID | Targeted loop | Loop DNA sequence | Loop protein sequence | Isolation method | Verified through recloning? | Part of coctail? |
|---|---|---|---|---|---|---|
| T3 (HI:KAG I) | HI | AGAAAGGCGGGATT--------ACA (SEQ ID NO: 72) | RKAGI---T (SEQ ID NO: 100) | direct plaque picking | | |
| T3 (HI:RTF I) | HI | AGACGTACTTTTATT--------ACA (SEQ ID NO: 73) | RRTFI---T (SEQ ID NO: 101) | direct plaque picking | | |
| T3 (HI:RDIR LSI) | HI | AGACGGGATATAGGCTTAGTATTACA (SEQ ID NO: 74) | RRDIRLSIT (SEQ ID NO: 102) | direct plaque picking | Yes | |
| T3 (HI:RFF V) | HI | AGACGTTTTTTTGTT--------ACC (SEQ ID NO: 75) | RRFFV---T (SEQ ID NO: 103) | panning on ΔwaaC | Yes | Yes |

Example 6: Host Range of Isolated Phagebodies

Randomly selected plaques were picked, plaque purified and amplified from each banks using either ΔwaaC, ΔwaaG or a naturally occurring T3 resistant mutant named D10 (see material and methods) and those that grew robustly in liquid culture were studied. To evaluate the phenotypic diversity our library approach can provide, the EOP of all the above mentioned isolated phage samples was measured on the two isolation LPS mutants ΔwaaC and ΔwaaG along with 8 T3 resistant clones that were independently isolated across various experiments where WT T3 was plated onto WT BL21. Transformation of each of these isolates with a plasmid expressing waaG (pSLM173) restored T3 infectivity in 3 of the 8 strains (FSL 397, FSL401 and D10) suggesting they are waaG mutants (TABLE 8). This data provides a glimpse of the capacity of each phagebody to target resistance evolution during phage challenge and provide data about the phenotypic diversity that the different gp17 sequences create.

TABLE 8

Complementation of T3 resistant mutants of
E. coli BL21 by a plasmid expressing waaG.

| | pwaaG (pSLM173) | |
|---|---|---|
| | − | + |
| BL21 | 1 | 1 |
| waaC | 0 | 0 |
| waaG | 0 | 1 |
| FSL396 | 0 | 0 |
| FSL397 | 0 | 1 |
| FSL398 | 0 | 0 |
| FSL399 | 0 | 0 |
| FSL400 | 0 | 0 |
| FSL401 | 0 | 1 |
| FSL402 | 0 | 0 |
| D10 | 0 | 1 |

Figure 8:
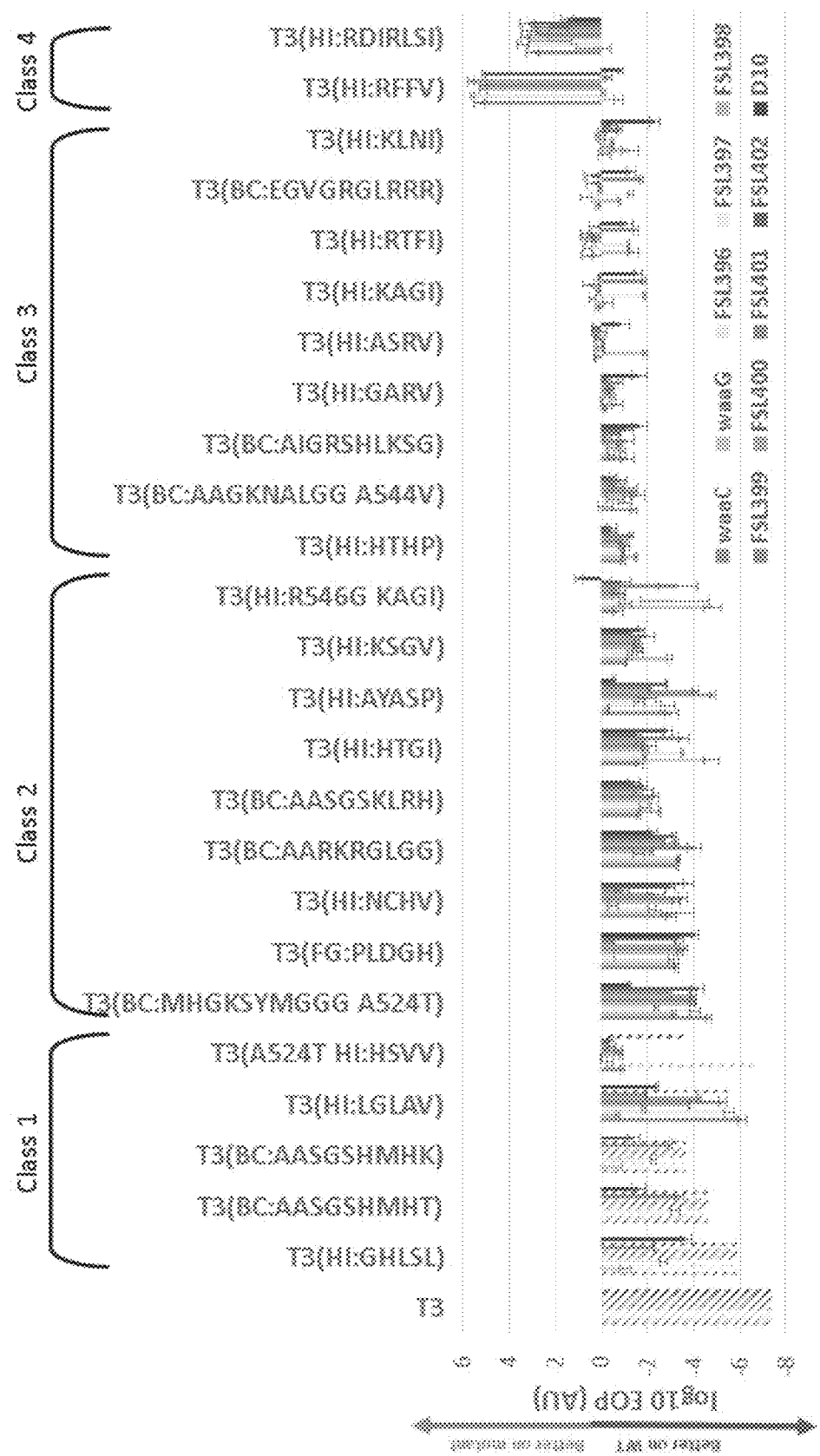
FIG. 8. Infectivity of bank isolates towards T3 resistant mutants of E. coli BL21. The infectivity of 27 independent selected phages isolated from various gp17 banks was on 8 naturally occurring T3 resistant mutants of E. coli BL21 as well as on the two constructed LPS mutants ΔwaaC and ΔwaaG was evaluated through EOP measurement which is plotted as its log 10 value. Stripe patterned data points are beyond detection limit (no plaques detected) which is calculated as the inverse of the WT E. coli BL21 number of pfus in the assessed volume. In each set of bars, the samples are (left to right): waaC, waaG, FSL396, FSL397, FSL398, FSL399, FSL400, FSL401, FSL402, D10.

In FIG. 8 the EOP of each phagebody is plotted as its log 10 value such that negative values indicate a phage that is poorer than wild-type at infecting the test strain while positive values indicate a phage which is better than wild-type and a log 10 EOP of 0 denotes a phage that plaques just as well on the mutant as on the wild-type E. coli BL21. Each test host is coded by a different shade for the respective bars shown in FIG. 8, wherein the samples are (left to right): waaC, waaG, FSL396, FSL397, FSL398, FSL399, FSL400, FSL401, FSL402, D10.

The different phagebody isolates could be roughly classified into 4 classes. Class 1 phages are phages which were only marginally better than T3, infecting only a small subset of bacterial mutants at very low EOPs. Class 2 are phages which infected the majority or all mutants but at low EOPs. Class 3 are phages that infected all T3 resistant mutant at an EOP>=0.01 (at least 1/100 pfu is infective towards mutant bacteria) and class 4 are phagebodies that actually switched host range instead of broadening it. They have become immensely better at infecting mutant bacteria than wild-type BL21. The large variety of phenotype within this small subset of randomly selected phages is a testament to the power of the method.

Example 7: Resistance Prevention from Phagebodies but not T3

Figure 9:
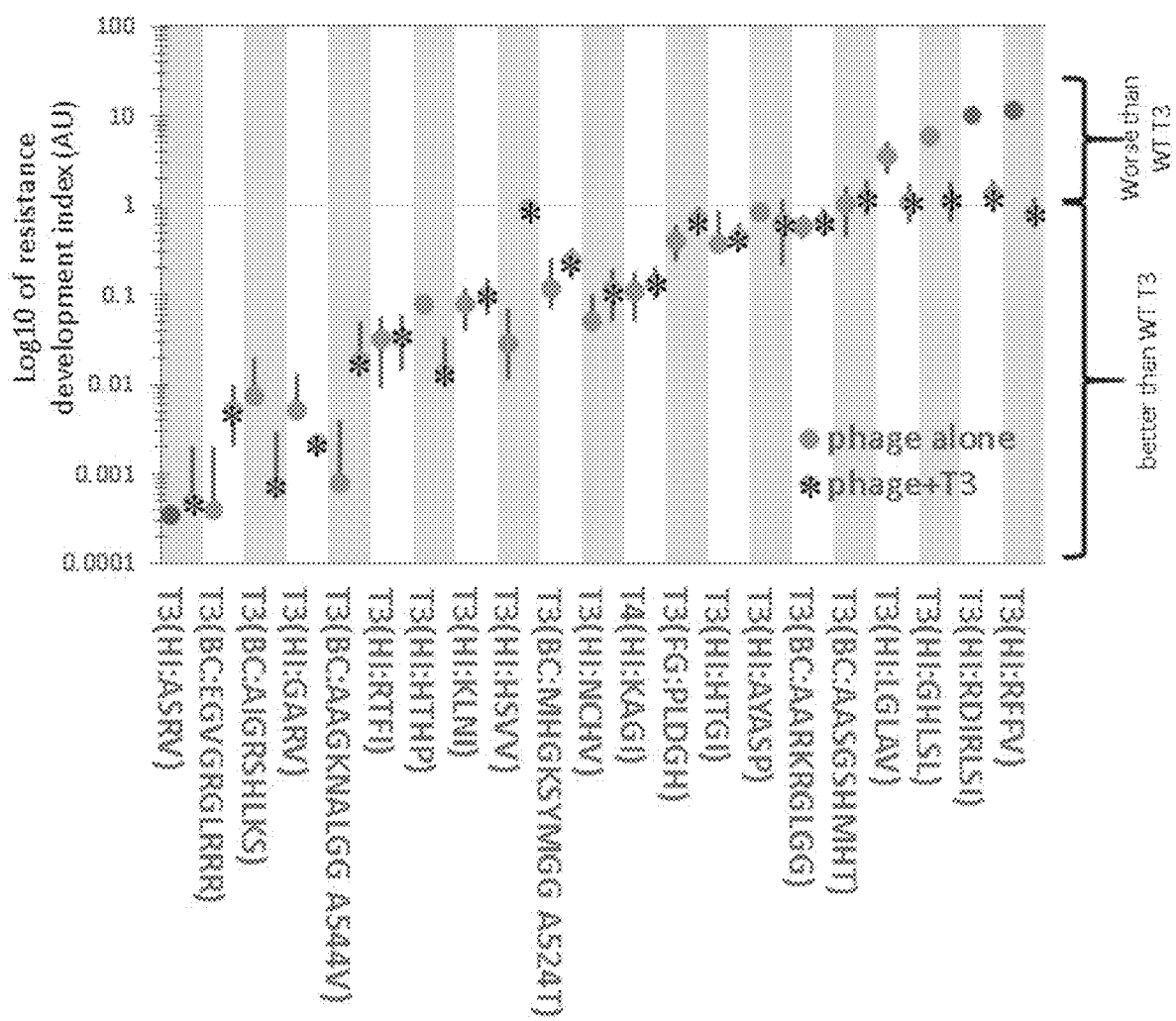
FIG. 9. Bacterial resistance development index. The capacity of a given T3 variant to eliminate resistance development in WT BL21 cultures was evaluated on plates seeded with about $10^5$ phages and $10^8$ bacteria. The resistance index for each variant was calculated by determining the ratio of the number of resistant colonies observed after 24 hrs to that obtained with WT T3. All experiments were done in triplicates. Expressed on a log 10 scale, a value below 1 indicates that the phage or cocktail prevents resistance better than WT T3 and conversely, a value above 1 indicates the phage or cocktail is worse. The first dot on the left represents a value below detection limits.

A simple test was devised consisting of mixing a phagebody and wild-type BL21 at an MOI of about $10^{-3}$ in top agar on a plate and counting the number of surviving colonies after 24 hrs. A resistance index was calculated for each phagebody by dividing the number of colonies from T3 infected plate by that of phagebody infected plates. Finally, it was also tested whether adding T3 to each phagebody infection in order to assess whether the cocktail could improve performance. Plotted in FIG. 9, plain dots represent the resistance index of a given phagebody assayed alone while dots with asterisks represent the resistance index of the corresponding minimalistic cocktail.

T3(HI:ASRV) showed the highest potency at preventing resistance appearance. Indeed, alone, no colonies even appeared. It represents an about 800-fold lower resistance level compared to wild-type T3. Surprisingly, adding T3 had a negative impact on T3(HI:ASRV) performance. All 9 class 3 phagebodies performed well in the resistance development assay and fell within the 12 phages that decreased resistance at least 10-fold (log 10 resistance index below 0.1). The 3 others were class 2 phagebodies T3(HI:HSVV), T3(HI:NCHV) and T3(BC:MHGKSYMGG A524T). Strangely enough, addition of T3 had no or limited effect on the outcome of the assay except for the two class 4 phagebodies T3(HI:RFFV) and T3(HI:RDIRLSI) but even then, the results were disappointing as the cocktail did not perform better than T3 alone despite those two phagebodies targeting LPS mutants very efficiently in EOP assays. This points out to the difficulty of transferring host range data from one assay to another in a predictive manner.

The plate system used in the initial resistance impeachment experiments does not register the effects of evolution over long period of times in the presence of the phage selective pressure. Therefore the capacity of those phagebodies to control bacterial population over 3 consecutive passages were examined using a high-throughput 96-well plate system with a starting bacterial population of ~$10^7$ cfu and a MOI of ~$10^{-4}$. Under these conditions, which were chosen to mimic conditions during of an actual phage therapy situation where few phages may reach a comparatively large bacterial population at the site of infection, it was observed that 3 out of 8 replicates infected with T3 developed resistance against phage infection (FIG. 15A). T3(HI:ASRV), as in the previous assay, decreased resistance development as only 1 of the 8 replicates managed to escape predation (FIG. 15D), however none of the other phagebodies performed significantly better than T3 (FIG. 15B-15C, 15E, 15F). More surprisingly, T3(HI:RDIRLSI) (FIG. 15F), one of the class 4 phagebody that infected wild-type BL21 very poorly in the EOP and resistance index assays, performed about on par with T3 in this assay suggesting that growth conditions on plates and liquid are sufficiently different that a receptor usable by T3(BC: RDIRLSI) is present under the latter but not the former conditions.

Figure 10:
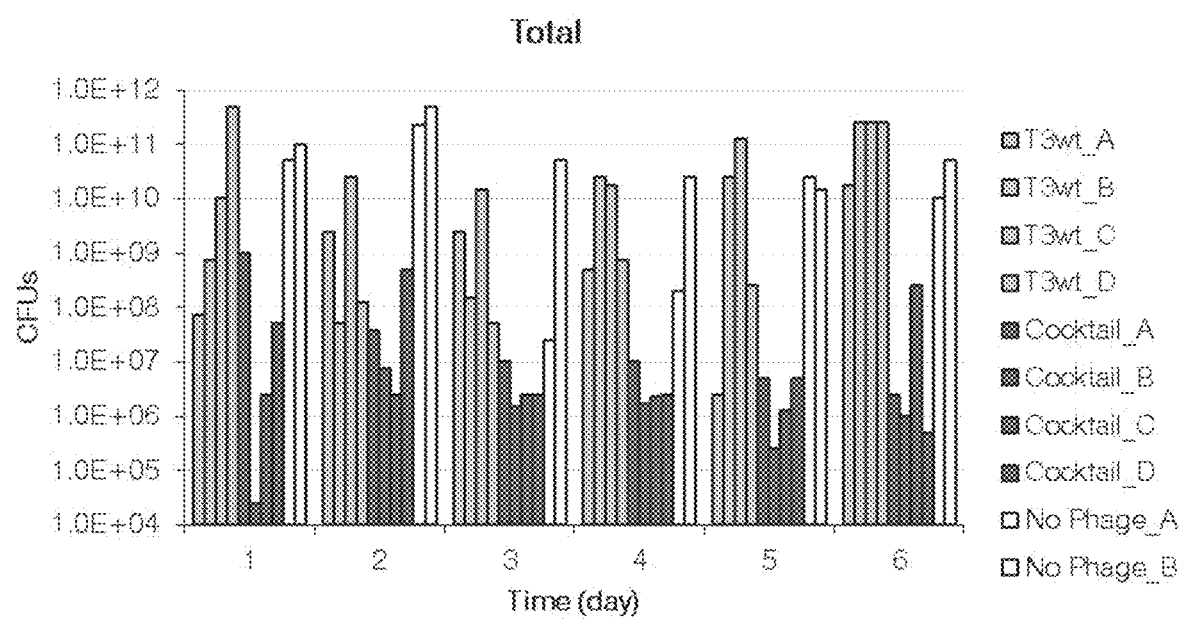
FIG. 10. Cocktail of chosen T3 variants prevents resistance development in large evolving populations of E. coli BL21. Infections were run in quadruplicate in 10 ml LB batch cultures subcultured every 24 hrs into fresh medium through 100-fold dilution with either WT T3 or a cocktail of 12 variants isolated from host range altered libraries. Bacterial counts in each of these microcosms was measured at each subculture steps and compared to that of 2 replicate cultures not infected with phage. For each time point, the set of bars, from left to right, represents: T3wt_A, T3wt_B, T3wt_C, T3wt_D, Cocktail_A, Cocktail_B, Cocktail_C, Cocktail_D, No Phage_A, No Phage_B.

Whether a cocktail of phagebodies could prevent resistance appearance better and suppress the growth and evolution of a large bacterial population was next determined. Some of the phagebodies described above originated from a phage enrichment protocol aimed at selecting those phage variants that are most adept at targeting bacterial mutants and bacteria growing in liquid cultures. Phagebody banks were repeatedly panned onto either ΔwaaG, ΔwaaC or D10 after 3 enrichment steps, individual plaques were picked, the gp17 gene sequenced and the phagebodies phenotypically characterized. A cocktail composed of 10 randomly selected phagebodies from this experiment was formulated and used to infect replicate liquid microcosms of 50 ml. Based on the fidelity of E. coli replication and data from the resistance index experiments, it was estimated that each such culture contained between 1000 and 10000 T3 resistant mutants at the time of phage addition and continued replication and evolution could of course generate new ones during the challenge. The ideal MOI was first assessed through titration. The effectiveness of the T3 phage application decreases with decreasing MOI whereas phage concentration seemed to have no impact on the phagebody cocktail capacity to kill bacteria (FIG. 8) even at an MOI of $10^{-7}$. To quantify the long-term effects of the phagebody cocktail at minimizing resistance, a kill assay was performed in which CFUs were measured over time (FIG. 10) at an MOI of $10^{-3}$. Impressively, the phagebody cocktail was able to prevent resistance for long term (greater than 6 days), whereas mutants quickly arose for a T3 wild type infection in less than 24 hours. Lastly, the phagebody cocktail was able to kill the resistant mutants at approximately three orders of magnitude better than T3.

As demonstrated herein, the host range of phage T3 can be altered efficiently by generating genetic diversity within host contacting regions chosen based on available structural data. This is a process reminiscent of the Diversity Generating Elements found in *Bordetella* phage BPP-1 (Guo, et al. Mircrobiol. Spectr. 2 (2014)). The distal fragment of BPP-1 tail fiber protein Mtd was also crystallized and although it adopts a completely different fold as the T3 gp17 tip, the general shape of the C-terminal fragment of both protein is not dissimilar and they both are trimeric and there are surprising resemblances between the location of the host range altering regions mutagenized as described herein and those which are targeted by BPP-1 DGR (McMahon et al. Nat. Struct. Mol. Biol. 12, 886-92 (2005)). In addition, BPP-1 DGR, just like the system described herein, generates diversity that can be used to counter-act resistance evolution in the host. These striking functional convergences between the naturally sourced DGRs and the synthetic approach described herein highlight the generalizable principle underlying the approach described herein. As the repertoire of phage host binding protein for which structural data is available increases, the value of this host range alteration method will increase and it will be a transformative step in how phages and possibly any virus are isolated for therapeutic and biotechnological applications.

Example 8: Primer Based Randomization of Gp17 Loops pSLM22 is a plasmid that carries the last 294 last base pairs of T7 gp17 surrounded by 50 bp on each side of homology to the corresponding region of phage T3. This plasmid recombines with a frequency of about 1-5% into T3 to create a T3 phage with the host range of T7. This plasmid was used as the basis to introduce variability in 17 loops via PCR with primers carrying randomization (NNK codons) in the regions corresponding to the loops.

All primers were purchased from IDT. All randomization primers were PAGE purified. Other primers were simply desalted. Randomization of loop coding regions was achieved using NNK for each of the codons of those areas. NNK was chosen because it limits introduction of stop codons while still generating all possible amino acid changes.

PCR amplification of pSLM22 with ppAY15 and ppAY16 results in introduction of random amino acids at all positions of loops DE and FG but not in loops BC and HI. PCR amplification of pSLM22 with ppAY17 and ppAY18 followed by a second amplification with ppAYC15 and ppAY16 allows randomization of loops AB, BC, DE, FG and HI simultaneously. PCR amplification of pSLM22 with ppAY37 and ppAY18 followed by a second amplification with ppAYC15 and ppAY16 allows randomization of loops BC, DE, FG and HI simultaneously. Sequence of primers used are provided TABLE 2.

The PCR products were circularized using an ApaI restriction site generated on each end of the PCR product via a conservative point mutation in the sequence of the T7 gp17 sequence. The circularized PCR products were then transformed into highly competent DH10B cells by electroporation. Plasmids were recovered by miniprep and transformed into electrocompetent FSL71/pACY22. After 2 hrs of recovery in SOCS, the resulting transformants were diluted into 30 mL of LB kanamycin/carbenicillin and grown overnight to eliminate non transformed cells. This is referred to as the bank. The bank may contain up to ~$10^9$ different clones (gp17 fragments with non-natural sequences). A fraction of the bank is then diluted into fresh medium, infected at a multiplicity of infection (MOI) of 3 with wild-type T3 and the growth pursued for about 2 hrs at which point almost all cells are lysed. The lysate is sterilized with chloroform, spun down to remove the solvent and debris and saved at 4° C. until testing. This is referred to as the bank lysate.

Testing was done in either of two ways: 1) direct plaque formation assay of the bank lysate onto confluent lawns of a strain normally poorly or not susceptible at all to T3 infection looking for plaques indicative of a phage now capable of sustaining infection of that strain; or 2) bank lysate amplification on the target host followed by plaquing of this amplification step onto the same target cells. Amplification is often necessary to detect rare mutants or those that have poor adsorption properties and therefore do not grow very robustly.

To help identify positive bank lysate amplification cultures where phages have been growing, a bacterial lysis indicator was used. Chlorophenol red β-D-galactopyranoside (CPRG) is a yellow compound that releases a dark red/pink pigment upon hydrolysis by lacZ, the beta-galactosidase. LacZ is an intracellular activity that only gets to the medium if cells lyse and CPRG cannot diffuse through bacterial membrane so that contact between the indicator CPRG and LacZ requires phage mediated lysis of the cells. CPRG was used to test the presence of lacZ in the supernatants of bank lysate amplifications on various *E. coli* strains (which are all lac$^+$) as an initial screening. A final CPRG concentration of 0.35 mM CPRG was used into cell free culture supernatants where lacZ expression was induced before bank lysate addition with 0.4 mM IPTG. A threshold for detection was set at 30 minutes as the compound will naturally hydrolyze over time and baseline levels of lacZ are present in any culture. This method allowed detection of as few as 10-100 phage particles in a 1.5 mL culture and may be made more sensitive with careful optimization.

Figure 18:
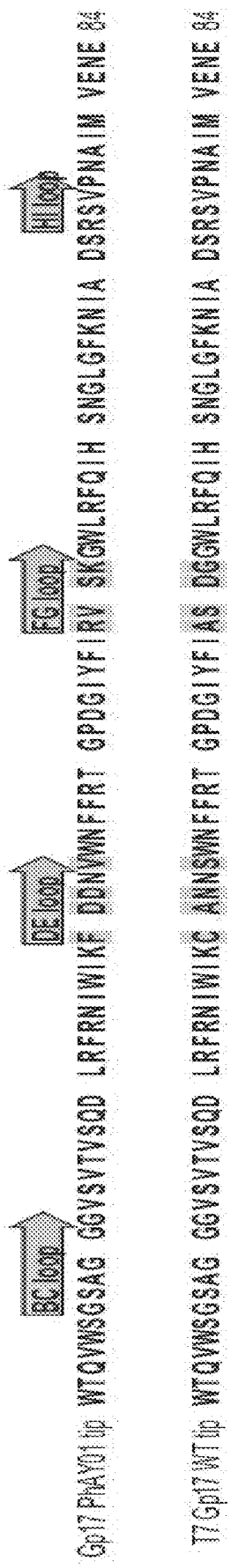
FIG. 18. Alignment of the tip sequences of phages PhAY01 and T7 (top to bottom: SEQ ID NOs: 181-182).

The first banks were screened against *E. coli* MG1655, various mutants in the lipopolysaccharide biosynthesis pathway of *E. coli* K-12, part of the ECOR collection (www.shigatox.net/new/reference-strains/ecor.html), a few different Salmonellae and Shigellae, *Yersinia pseudotuberculosis* YPIII and IP2666, a few different *Pseudomonas aeruginosa* and *putida* and *Klebsiella* sp.390. This randomization proved useful in generating a mutant of T3, PhAY01, that infects strains MG1655 efficiently and has unnatural sequences in loops DE and FG as illustrated in FIG. 18. Alignment is made to the T7 tail fiber protein sequence because this is what T3 recombines with when infecting pSLM22 containing strains.

Example 9: Randomization of Single or Multiple Loops

To circumvent some of the shortcomings of the strategy described above in Example 8, a new PCR based strategy was designed that modifies a single loop at a time but can be used iteratively to generate pools of mutants with modification in several loops.

As a template plasmid pSLM49 was used which has the entire T3 gp17 gene cloned inside of it and some fragments of genes upstream and downstream of it. This plasmid greatly increases the amount of homology available for recombination with the phage on each side of the modified loops. To introduce variability, the entire plasmid is PCR amplified with a pair of primers that initiate polymerization on each side of the loop sequence to modify. One of the primers is long and contains the randomized loop sequence along with 20-30 nucleotide homology to the other end of the full plasmid amplicon. The overlapping primers allow for circularization of the final plasmid upon transformation into bacteria. The amplification therefore results in a product that spans the full length of the plasmid, with random sequences within the targeted loop sequence and about 20-30 bp of redundancy at the ends. The product may be transformed into cells after DpnI digestion and silica column clean up and concentration (Zymo research clean-and-concentrator-5). This method is analogous to QUICK-CHANGE®. For a slightly higher transformation efficiency, circularization by Gibson assembly followed by clean up and concentration on silica columns (Zymo research clean-and-concentrator-5) can be used.

Iterative loop mutagenesis can be performed either from Gibson circularized plasmids or from plasmids extracted after transformation into cells. Each iteration can be done with a different primer thus generating diversity in several loops or with the same primer set thus increasing diversity in that particular loop.

For controls, banks were generated in that same manner in each beta-sheet and in each inward facing loops. Following analysis, the general trend is that inward loops have no implication in host range, beta-sheets occasionally impact host range and the AB loop, that forming the hinge between the pyramidal stem of the Gp17 tip and the globular domain is very involved in host range.

Certain primers used are listed in TABLE 9 along with comments on which primers target which tip structure.

CRISPR-cas9 system targeting the wild-type phage were designed but provided little added benefit and are not further described here although CRISPR counter-selection of the wild-type virus could increase the efficiency of the method.

Phages that infect *E. coli* MG1655, EMG2 and BW25113, *Yersinia pseudotuberculosis* also were obtained. Phages active against LPS mutants of *E. coli* K-12 BW25113 (ΔwaaC::kan; deep rough strain) that are normally completely resistant to both T3 and T7 and for which it was difficult to obtain naturally occurring phage infective mutants also were obtained, as were phages infect ECOR63 and ECOR4, strains which are normally infected very poorly by T3.

There are other phages with similar tail fibers such as, but not limited to, 285P, FE44, BA14, for which the technique is applicable although the exact precise location of the loops and beta-sheets is not known with absolute certainty as the 3-dimensional structure of the tail tip has not been determined.

Example 10: Random Mutagenesis of the Tip Encoding Fragment of T3 gp17

In this method, variability was introduced via random mutagenesis using the Jena biosciences dNTP mutagenesis kit.

The tip portion of T3 gp17 was amplified with primers PST691/PST692 or PST703/PST704 from pSLM49 in the presence of the mutagenic base analogs dPTP and 8-oxo-dGTP as advised by the manufacturer with non-proofreading polymerases. Mutagenesis was performed for 10, 20 or 30 amplification rounds and the resulting amplicon was diluted 50-fold into a mutagen free PCR reaction with the same primer pairs in order to settle the changes. After DpnI digestion to eliminate background, the resulting amplicons were cloned into a PCR product corresponding to the rest of pSLM49 by Gibson assembly. For the PST691/692 amplicon, the complement product was generated with primers PST693/PST694. For the PST703/704 amplicon, the complement PCR product was generated with primers PST705/PST706. The resulting DNA was cleaned up and concentrated before transformation into DH10B. Such banks have generated mutants of T3 active towards MG1655, EMG2, BW25113 and its LPS mutants, and *Yersinia pseudotuberculosis*.

Example 11: Other Methods and their Limitations: Golden Gate Approach pSLM22 is a plasmid that harbors the 294 bp long C-terminal tip of T7 gp17 surrounded by 50 bp of homology on each side to the corresponding gp17 tip region of T3. Recombination between pSLM22 and T3 yields to functional T3/T7 hybrids with the host range of T7. Starting from this plasmid, various approaches were tried to create diversity in the AB, BC, DE, FG and HI loops of the T7 Gp17 tip.

Figure 19:
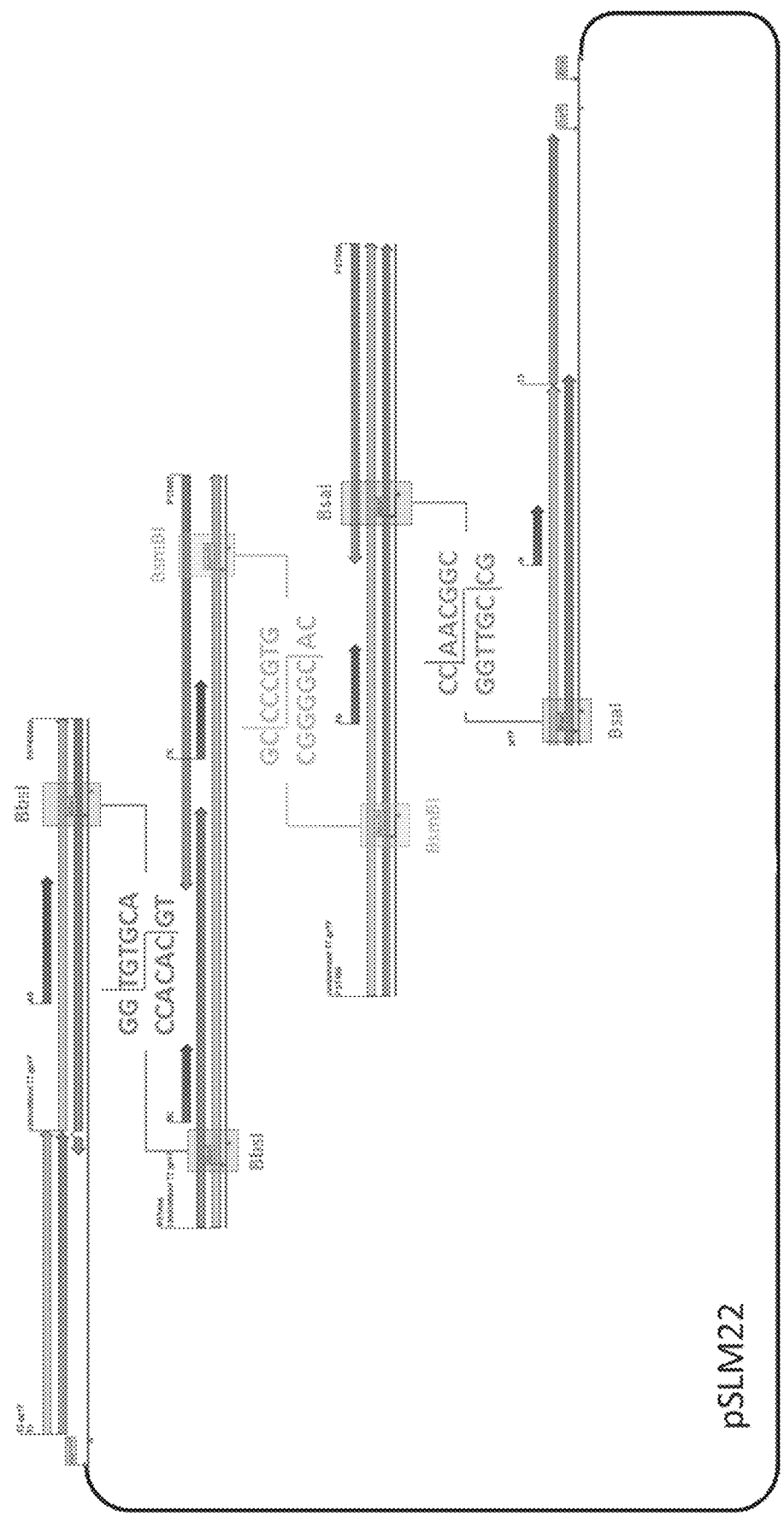
FIG. 19. Schematic illustration of the first gp17 randomized bank assembly method. Highlighted in between each of the 3 pieces that are ligated together are the overhangs generated by type IIs restriction enzymes.

One attempt at creating a diversified bank of Gp17 used a GOLDEN GATE® assembly system. The backbone and T3 homology regions of pSLM22 were amplified with primers PST494 and PST495. These long oligonucleotides also introduced NNN in place of each codon of loops AB and HI respectively. Finally PST494 and 495 also introduced a restriction site for the type IIs enzyme BbsI and BsaI. These sites were introduced in such a way that restriction digestion would cleave off the restriction recognition site and allow scarless cloning of fragments in place of the gp17 tip sequence. The remainder of the gp17 tip sequence was provided by two template less PCR product obtained by annealing and filling in of primers PST496/PST497 and PST498/PST499. These primers introduce NNN codons in loops BC and DE for the first one and FG for the second one. PST496/497 had a BbsI site on one side and BsmBI site on the other while PST498/499 had a BsmBI and a BsaI site. Restriction sites were chosen in such a way that they would generate overhangs that allow the PST496/497 product to anneal and ligate with the BbsI restricted pSLM22 PST494/495 product on one hand and the BsmBI restricted PST498/499 on the other hand. Similarly the BsaI site of PST498/499 was chosen to allow annealing and ligation with the BsaI restricted pSLM22 PST494/495. This assembly procedure is depicted in FIG. 19.

This bank assembly method proved disappointing. First of all, transformation efficiency proved low, generally generating only in the range of $10^3$ to $10^4$ clones. On top of that, out of about 50 clones picked from ligation plates and analyzed by sequencing, hardly any actually had the correctly assembled tail fiber module. In most cases, stop codons appeared in frame with the gp17 coding sequence and in some cases the randomization created unexpected BsaI, BbsI or BsmBI sites that would lead to truncated gp17 sequences. It was also clear that BbsI and/or BsmBI did not cut completely and it was realized there was no need to go through the complication of three type IIs restriction enzymes as the overhang depend on the location of the enzyme recognition site and can therefore be chosen at will.

Example 12: Other Methods and their Limitations: Nested Template

Figure 20:
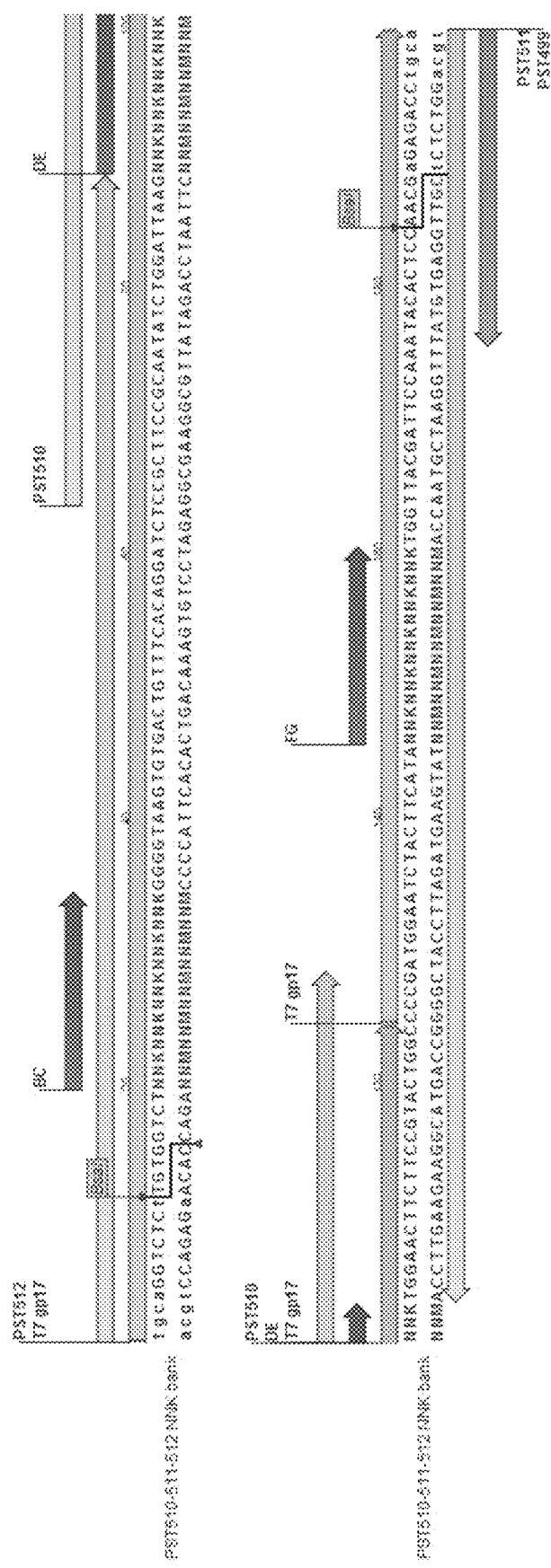
FIG. 20. Sequence of the PST510-511-512 PCR product before BsaI restriction (top to bottom: SEQ ID NOs: 183-184).
Figure 21A:
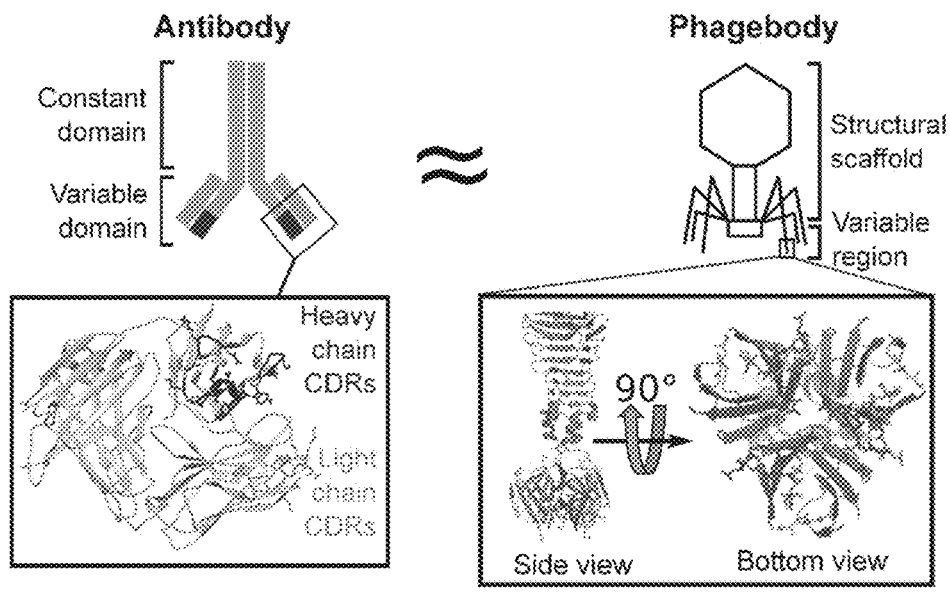
FIGS. 21A-21B. Schematic illustrating the similarities between antibodies and phage tail fibers and how phagebody libraries can be used to reduce bacterial resistance to phages.
Figure 21B:
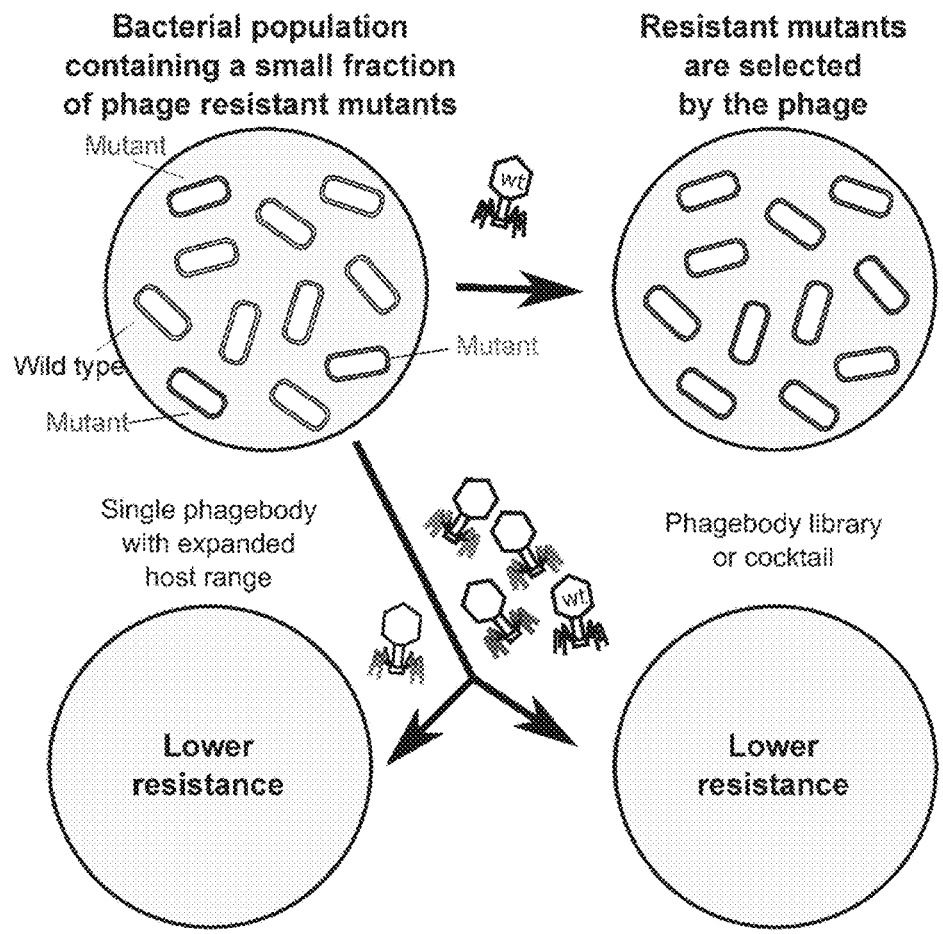

Nested template less PCR was also used to generate the whole randomized gp17 insert as one product instead of two on order to increase ligation efficiency. In order to limit stop codon appearance, randomization no longer was the result of NNN codons but of NNK codons which cannot encode TAA or TGA stop codons. In this method, pSLM22 was amplified with PST494bis and PST495bis which are identical to the original PST494/495 except for the NNK codons and the BbsI site of PST494 replaced by BsaI. To generate the randomized insert, PST510, PST511 and PST512 were mixed in equimolar amounts and PCRed together. The resulting product was expected to be a 199 bp long fragment with BsaI sites on each end placed in such a way as to ensure faithful reconstruction of a Gp17 tip gene fragment after cloning into BsaI digested pSLM22 PST494bis/PST495bis. The 199 bp band was gel purified after BsaI restriction and cloned into the appropriate vector. Ligation efficiency increased 10-100 fold compared to the previous method but was not high enough yet. Stop codons plagued only about half of the clones (vs close to 100% previously) and there were less abnormal ligation products but still only about 10% of the clones had a useful gp17 tip, that is full length without any stop codon. Most of the abnormal ligation product was eliminated by running the template less PCR in two steps and by careful optimization of annealing temperature. First PST510 and PST511 were annealed and amplified together. The product was gel purified and submitted to a second PCR using only PST511 and PST512 resulting in a full length 199 bp fragment. Mispriming between PST511 and PST512 may have occurred at the annealing temperature required to get a product when all three primers are mixed together. The expected product of the PST510-PST511-PST512 template less PCR is depicted in FIG. 20.

TABLE 9

Primer sequences

| | | | |
|---|---|---|---|
| ppAY15 | CCATCGGGGCCCGTACGGAAGAAGTT CCAMNNMNNMNNMNNMNNCTTANTCC AGATATTGCGGAAGCGGAGATCCTGT GAAACAGTCACACTTACCCC | randomize DE and FG | SEQ ID NO: 104 |
| ppAY16 | CCGTACGGCCCCGATGGAATCTACT TCATANNKNNKNNKNNKNNKTGGTTA CGATTCCAAATACACTCCAACGGCCT CGGATTC | randomize DE and FG | SEQ ID NO: 105 |
| ppAY17 | CTGTGAAACAGTCACACTTACCCCMN NMNNMNNMNNMNNAGACCACACCTGA GTCCAMNNMNNMNNMNNMNNMNNMNN GCTGTCCGTAGGMAGCATCA | randomize AB, BC and HI | SEQ ID NO: 106 |
| ppAY18 | CTCCAACGGCCTCGGATTCAAGAATA TTGCAGACAGTNNKNNKNNKNNKAAT GCAATCTGGTCGAGAACGAG | randomize AB, BC and HI | SEQ ID NO: 107 |
| PST494 | agacGAAGACtgCACACCTGAGTCCA NNNNNNNNNNNNNNNNNNNNNNCCTGT CACGTAGGTAAGCATCCAGC | create a T7 tip with randomization in each loop | SEQ ID NO: 108 |
| PST494bis | TGCAGGTCTCTCACACCTGAGTCCAM NNMNNMNNMNNMNNMNNMNNGCTGTC ACGTAGGTAAGCATCAAGC | create a T7 tip with randomization in each loop | SEQ ID NO: 109 |
| PST495 | tgcaGGTCTCtAACGGcCTCGGATTC AAGAATATTGCAGACAGTNNNNNNNN NNNNAATGCAATCATGGTGGAGAACG ACTA | create a T7 tip with randomization in each loop | SEQ ID NO: 110 |
| PST495bis | tgcaGGTCTCtAACGGcCTCGGATTC AAGAATATTGCAGACAGTNNKNNKNN KNNKAATGCAATCATGGTGGAGAACG AGTA | create a T7 tip with randomization in each loop | SEQ ID NO: 111 |
| PST496 | gtctGAAGACtgTGTGGTCTNNNNNN NNNNNNNNNGGGGTAAGTGTGACTGT TTCACAGGATCTCCGCTTCCGCAATA TCTGGATTAAG | create a T7 tip with randomization in each loop | SEQ ID NO: 112 |
| PST497 | GAGACGCCGTCTCaCGGGGCCAGTAC GGAAGAAGTTCCANNNNNNNNNNNNN NNCTTAATCCAGATATTGCGGAAGCG G | create a T7 tip with randomization in each loop | SEQ ID NO: 113 |

TABLE 9-continued

| | | | |
|---|---|---|---|
| PST498 | CGGCGTCTCaCCCGATGGAATCTACT TCATANNNNNNNNNNNNNNNNTGGTTA CGATTCCAAATACACTCCAACGaGAG ACCtgca | create a T7 tip with randomization in each loop | SEQ ID NO: 114 |
| PST499 | tgcaGGTCTCtCGTTGGAGTGTAT | create a T7 tip with randomization in each loop | SEQ ID NO: 115 |
| PST510 | CCGCTTCCGCAATATCTGGATTAAGN NKNNKNNKNNKNNKTGGAACTTCTTC CGTACTGGCCCCG | create a T7 tip with randomization in each loop | SEQ ID NO: 116 |
| PST511 | tgcaGGTCTCtCGTTGGAGTGTATTT GGAATCGTAACCAMNNMNNMNNMNNM NNTATCAAGTAGATTCCATCGCGGCC AGTACCGAAGAAGTTCCA | create a T7 tip with and in each loop | SEQ ID NO: 117 |
| PST512 | tgcaGGTCTCtTGTGGTCTNNKNNKN NKNNKNNKGGGGTAAGTGTGACTGTT TCACAGGATCTCCGCTTCCGCAATAT CTGGATTAAG | create a T7 tip with randomization in each loop | SEQ ID NO: 118 |
| PST69 | GTACTAAGTGGGGAGGTAAGTGGCTT | amplify pSLM49 constant region | SEQ ID NO: 5 |
| PST692 | GTGTGATAGTCCATCCGTGGACTTAA AGTA | amplify pSLM49 constant region (mutagenize BC-HI) | SEQ ID NO: 6 |
| PST693 | AAGCCACTTACCTCCCCACTTAGTAC | amplify T3 17 tip (BC to HI) for error prone PCR | SEQ ID NO: 7 |
| PST694 | TACTTTAAGTCCACGGATGGACTATC ACAC | amplify T3 17 tip for error prone PCR | SEQ ID NO: 8 |
| PST695 | CCIGIGGGAGAGTATCAGTCTGAGAA CCMNNMNNMNNMNNMNNMNNMNNMNN MNNAGCCCATACTTGAGTCCAGGCC | randomize BC | SEQ ID NO: 21 |
| PST696 | GGTTCTCAGACTGATACTCTCCCACA GG | randomize BC | SEQ ID NO: 22 |
| PST699 | GGCAGGGTATTTAAGAACATAGCGGA TAGANNKNNKNNKNNKACAGCAATAG CCGTAGAGGACGTG | randomize PG | SEQ ID NO: 23 |
| PT700 | TCTATCCGCTATGTTCTTAAATACCC TGCC | randomize PG | SEQ ID NO: 24 |
| PST701 | AACTGGTCCTGACCGTATCTACTTCC TTNNKNNKNNKNNKNNKTGGCTAAAA TTCCAGATACACTCTAATGGC | randomize HI | SEQ ID NO: 25 |
| PST702 | AAGGAAGTAGATACCGTCAGGACCAG TT | randomize HI | SEQ ID NO: 26 |
| PST703 | GGCCTCGACTCAAGTATGGGCT | amplify pSLM49 constant region | SEQ ID NO: 119 |
| PST704 | CACGTCCTCTACCGCTATTGCTGT | amplify T3 17 tip (AB to HI) for error prone PCR | SEQ ID NO: 120 |
| PST705 | AGCCCATACTIGAGTCCAGGCC | amplify T3 17 tip (AB to HI) for error prone PCR | SEQ ID NO: 121 |
| PST706 | ACAGCAATAGCCCTAGAGGACGTG | amplify pSLM49 constant region (mutagenize AS to HI) | SEQ ID NO: 122 |
| PST767 | GTACTAAGTGGGGAGGTAAGTGGCTT NNKNNKNNKNNKNNKNNKTACGT TAAGAAGACAATGGCCTGGACTCAA | randomize A in pSLM49 | SEQ ID NO: 123 |

TABLE 9-continued

| | | | |
|---|---|---|---|
| PST768 | GGCCATTGTCTTCTTAACGTAAGTATCGTT | randomize B | SEQ ID NO: 124 |
| PST769 | AACGATACTTACGTTAAGAAGACAATGGCCNNKNNKNNKNNKNNKNNKGCTGCTAGTGGTAGTTACATGGCAGG | randomize B | SEQ ID NO: 125 |
| PST770 | TCCTCCCATGTAACTACCACTAGCAGC | randomize C | SEQ ID NO: 126 |
| PST771 | GCTCCTAGTGGTAGTTACATCGGAGGANNKNNKNNKNNKNNKNNKCCACAGGACTTGCGATTCCGCAACATATGG | randomize C | SEQ ID NO: 127 |
| PST772 | GCGGAATCGCAAGTCCTGTCCGAGAG | randomize D | SEQ ID NO: 128 |
| PST773 | CTCTCCCACAGGACTTGCGATTCCGCNNKNNKNNKNNKNNKACCAGAAACAACTATTGGAACTCTTCCGA | randomize D | SEQ ID NO: 129 |
| PST774 | ATAGTTGTTTCTGGTCTTAATCCATATGTT | randomize E | SEQ ID NO: 130 |
| PST775 | AACATATGGATTAAGACCAGAAACAACTATNNKNNKNNKNNKNNKNNKGGTCCTGACGGTATCTACTTCCTTCAG | randomize E | SEQ ID NO: 131 |
| PST776 | GTCAGGACCAGTTCGGAAGAAGTTCC | randomize F | SEQ ID NO: 132 |
| PST777 | GGAACTTCTTCCGAACTGGTCCTGACNNKNNKNNKNNKNNKTCACCCGAGGGCGGTTGGCTAAAATTCCAG | randomize F | SEQ ID NO: 133 |
| PST778 | ACCGCCCTCGGCTGAAAGGAAGTAGATACC | randomize G | SEQ ID NO: 134 |
| PST779 | GGTATCTACTTCCTTTCAGCCGAGGGCGGTNNKNNKNNKNNKNNKNNKNNKTCTAATGGCAGGGTATTTAAGAACATAGCG | randomize G | SEQ ID NO: 135 |
| PST780 | GCCATTAGAGTGTATCTGGAATTTTAGCCAACC | randomize H | SEQ ID NO: 136 |
| PST781 | GGCTAAAATTCCAGATACACTCTAATGGCNNKNNKNNKNNKNNKNNKNNKNNKNNKGATGCGCCTCCAACAGCAATAGC | randomize H | SEQ ID NO: 137 |
| PST782 | TGGAGGCGCATCTCTATCCGCTATGTTC | randomize I | SEQ ID NO: 138 |
| PST783 | AAGAACATAGCGGATAGAGATGCGCCTCCANNKNNKNNKNNKNNKNNKCACCTGTAATAAGCATCAAAGGAACTACTT | randomize I | SEQ ID NO: 139 |
| PST784 | GAGAGTATCAGTCTGAGAACCTCCTCCC | randomize CD | SEQ ID NO: 140 |
| PST785 | GGGAGGAGGTTCTCAGACTGATACTCTCNNKNNKNNKNNKNNKNNKNNKAACATATGGATTAAGACCAGAAACAACTATTGG | randomize CD | SEQ ID NO: 141 |
| PST766 | AGTTCGGAAGAAGTTCCAATAGTTGTTTCTGG | randomize HE | SEQ ID NO: 142 |
| PST787 | CCAGAAACAACTATTGGAACTTCTTCCGAACTNNKNNKNNKGGTATCTACTTCCTTTCAGCCCGAGG | randomize FE | SEQ ID NO: 143 |
| PST788 | GTGTATCTGGAATTTTAGCCAACCG | randomize GH | SEQ ID NO: 144 |
| PST789 | CGGTTGGCTAAAATTCCAGATACACNNKNNKNNKNNKAGGGTATTTAAGAACATAGCGGATAGAC | randomize GH | SEQ ID NO: 145 |

TABLE 9-continued

| | | | |
|---|---|---|---|
| PST792 | AGTATCGTTTAGGTAAGCATCAAGCC | randomize AB | SEQ ID NO: 146 |
| PST793 | GGCTTGATGCTTACCTAAACGATACT NNKNNKNNKNNKNNKNNKNNKTGGAC TCAAGTATGGGCTGCTGCTAG | randomize AB | SEQ ID NO: 147 |
| PST794 | CTTAATCCATATGTTGCGGAATCGC | randomize DE | SEQ ID NO: 27 |
| PST795 | GCGATTCCGCAACATATGGATTAAGN NKNNKNNKNNKNNKTGGAACTTCTTC CGAACTTGGTCCTGACG | randomize DE | SEQ ID NO: 28 |
| PST800 | GACAATGGCCTGGACTCAAGTATGGG CTNNKNNKNNKNNKNNKNNKNNKNNK NNKNNKGGTTCTCAGACTGATACTCT CCCAC | random BC + 3 | SEQ ID NO: 29 |
| PST801 | GACAATGGCCTGGACTCAAGTATGGG CTNNKNNKNNKNNKGGTTCTCAGACT GATACTCTCCCAC | random BC - 3 | SEQ ID NO: 148 |
| PST802 | AGCCCATACTTGAGTCCAGGCCATTG TC | rev for random BC | SEQ ID NO: |
| PST803 | GGGTATTTAAGAACATAGCGGATAGA NNKNNKNNKNNKNNKNNKNNKACAGC AATAGCCGTACAGGCGTC | random HI + 3 | SEQ ID NO: 31 |
| PST804 | GGGTATTTAAGAACATAGCGGATAGA NNKNNKNNKNNKNNKNNKACAGC AATAGCCGTACAGGCGTC | random HI - 3 | SEQ ID NO: 149 |
| TPS805 | TCTATCCGCTATGTTCTTAAATACCC | reverse for random HI | SEQ ID NO: 32 |

Example 13: Phagebody Scaffold Choice and Structure Informed Tail Fiber Library Engineering Design Principles Perry and co-workers showed that evolution of phage T3 co-cultured with its host *E. coli* BL21 (BL21) proceeds through a limited number of pathways and is therefore predictable (Perry et al. PLoS One 10, e0130639 (2015)). The host initially develops resistance through mutations in the lipopolysaccharide (LPS) synthesis gene waaG, resulting in a truncated LPS. The phage responds by acquiring either one of two mutations in its tail fiber gene (gene 17)—D547G or D547N—which enables recognition of the truncated LPS. Subsequently, these evolved phages apply additional selection pressure for modifications to the host's LPS, resulting in mutations in the waaO and waaP genes, or in the trxA gene, which is essential for phage replication and gene expression. Consequently, T3 is unable to adapt naturally to maintain infectivity of these secondary mutations.

The tail fiber of T3 is responsible for initial host recognition through binding to the LPS. Each tail fiber is composed of a homotrimer of the gene 17 product, gp17. Previous work identified the carboxy-terminal ~450-553 amino acid globular domain, or the "tip", as a determinant for host specificity (Ando et al. Cell Syst. 1, 187-196 (2015)). Homology modeling (Swiss-model (Arnold et al., Bioinformatics 22, 195-201 (2006)) was used to generate the structure of the tip of T3 gp17 (residues 454-558) (FIG. 22A). The distal 104 a.a. portion of gp17 forms an intertwined globular domain shaped by an eight-stranded beta barrel (strands labeled B to I), where the strands are connected by random coils. Three of these coils, CD, EF and GH, are oriented towards the tail fiber shaft (inward loops). The four other coils, BC, DE, FG and HI, are displayed on the opposite side of the tip and point outwards away from the tail fiber (outward loops, highlighted in FIGS. 22A-22B). These structures suggested that these regions are likely to make contact with the host's surface and are important for receptor recognition.

Figure 28:
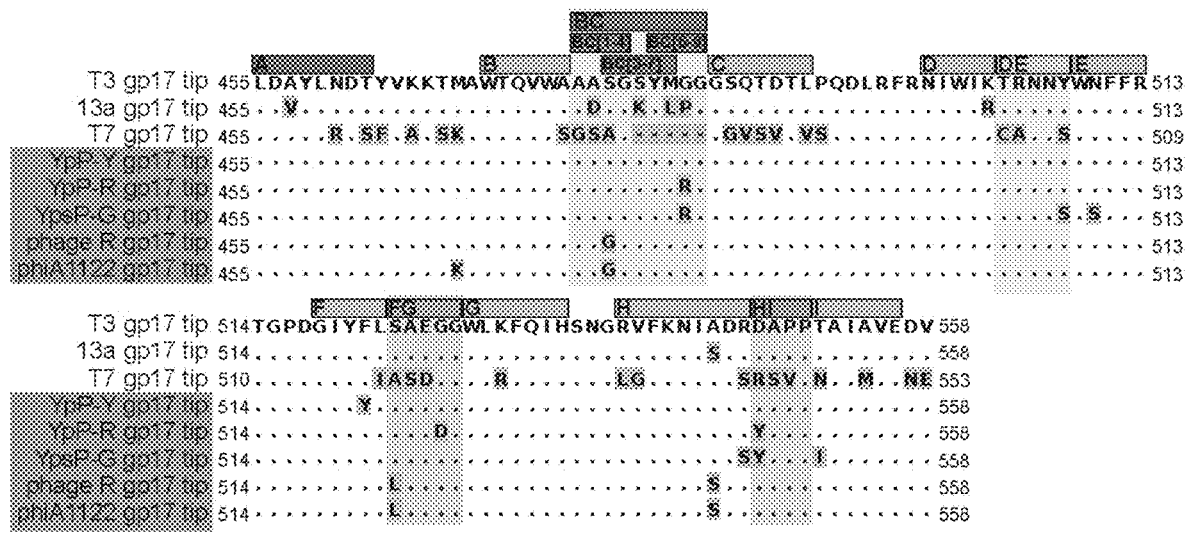
FIG. 28. Related to FIG. 22: Alignment of gp17 tip sequences (top to bottom: SEQ ID NOs: 170, 175, 186, 173, 176, 174, 172, 171). The T3 gp17 tip was aligned to the corresponding regions of tail fibers from other related wild-type phages, illustrating the enrichment of mutations in outward loops between related phages targeting different hosts. Identical residues are displayed as dots. The location of loops BC, DE, FG and HI are highlighted as in FIG. 22. The partial BC loop regions targeted for library designs (BC[1-4], BC[3-7] and BC[6-9]) are also shown. The highlighted gp17 proteins (on the left) indicate those originating from phages isolated on *Yersinia* species. Protein sequences from phages isolated on *E. coli* are not highlighted. Note that some of these phages may grow on both *E. coli* and *Yersinia* (T7 for example) while others may be specific to either strain (such as T3 that only grows on *E. coli*). The shaded boxes with bolded residues inside indicate amino acids that differ from the T3 gp17 sequence.

An alignment of a limited set of the gp17 tip region of T3-like phages indicated an enrichment of mutations within the loop sequences (FIG. 28). Wild-type T3 (T3 phage maintained on wild-type BL21) does not infect *E. coli* K-12 MG1655, but approximately 1 in $10^6$ to $10^7$ T3 phage acquires a mutation that allows it to efficiently plaque on MG1655. These plaques were picked, purified and grown on MG1655 to analyze the mutations that led to this host range change. In total, 66 individual mutants were isolated and studied to confirm the hypothesis that loops are important for host range determination. Sequencing of gene 17 revealed that 25 of the T3 mutants acquired mutations in the BC loop, 25 contained mutations in the HI loop, 2 had point mutations in the H or I n-sheet, and 14 had a combination of mutations throughout the tip region, including the outward facing loops. However, none of the isolated phages had mutations in the ~200 bp upstream or downstream of the tip or in the inward loops (TABLE 4), thus supporting the association between outward loops and host range determination. Collectively, these results suggested that targeting the outward loops for mutagenesis should modify T3's host range.

Because each of these loops are relatively small (4-9 a.a. long), experiments were performed to generate large diversity by replacing each codon within each targeted loop with NNK codons. This was accomplished by cloning the tail fiber gene 17 into a plasmid, which was then entirely PCR amplified with degenerate oligonucleotides designed to replace a single loop with a random sequence of a predetermined number of NNK codons (see methods and materials). The resulting plasmid libraries containing mutations in gene 17 were transformed into E. coli NEB5α, and the mutated regions were recombined into the T3 genome (1-5% of progeny phage acquired the plasmid-borne sequence) (Bull and Molineux, Heredity 100, 453-63 (2008); Bull et al., J. Mol. Evol. 53, 47-54 (2001); Springman et al., G3 (Bethesda) 2, 205-10 (2012)). Each loop size dictates the total theoretical sequence space of possible mutations. For the smaller HI loop, there are ~$10^6$ unique DNA sequences, while for the longest loop, BC, there are $10^{13}$ unique sequences. However, the theoretical protein sequence space is approximately 10-100 fold lower due to redundancy of the genetic code (TABLE 5). Since it is not feasible to exhaustively sample the entire sequence space of the full length BC loop, partially randomized BC loops were designed where only the first 4 codons (BC[1-4]), the central 5 codons (BC[3-7]), or the last 4 codons (BC[6-9]) were randomized, where the bracketed numbering indicates codon positioning within the loop (FIG. 22B). In addition, phagebody libraries were generated that contained elongated HI loops compared to wild-type T3 with either one extra codon (HI[+1]) or three extra codons (HI[+3]). FIG. 23A illustrates this pipeline.

Example 14: Phagebody Pipeline Validation

In order to quantify library diversity and to identify potential sequence biases, HiSeq was performed at each step of library synthesis. Rarefaction curves were plotted for each sequenced library (FIGS. 23C-23I). These results show that libraries targeting 4 codons saturated the theoretical sequence space. Although libraries targeting 5 codons were not fully saturating at the DNA sequence level, they covered a large majority of the potential protein sequence space when accounting for codon redundancy in the genetic code. Libraries designed against loops longer than 5 codons were not saturating at either the DNA or protein level. Comparing the diversity differences between each stage in library construction ("Plasmid" compared to "Transformed plasmid" and "Transformed Plasmid" compared to "Phage" in FIG. 23) suggested that the limiting step for library diversity is the transformation yield, while minimum loss in diversity can be attributed to the recombination efficiency. Thus, transformation yield was used as a measure to gauge library diversity.

To validate our hypothesis that loop randomization creates functional diversity, the libraries were screened for phagebodies that infect LPS mutants of BL21 and assayed whether they performed better than wild-type T3 at suppressing resistance evolution. Because LPS mutations are the main evolutionary pathway for bacterial resistance against wild-type T3 (Perry et al. PLoS One 10, e0130639 (2015)), two LPS synthesis genes were replaced independently with an apramycin resistance cassette to create BL21 ΔwaaG::apra (referred to as ΔwaaG) and BL21 ΔwaaC::apra (referred to as ΔwaaC). BL21ΔwaaG mutants lack the outer core of its LPS, including the glucose moiety that wild-type T3 uses as a receptor (FIG. 24A) (Heinrichs et al., Mol. Microbiol. 30, 221-32 (1998)). BL21ΔwaaC mutants are rougher LPS mutants that are almost completely devoid of LPS (FIG. 24A) (Heinrichs et al., Mol. Microbiol. 30, 221-32 (1998)). As expected, wild-type T3 displayed an efficiency of plating (EOP) below $10^{-12}$ on both strains. The EOP is the ratio between the phage titer on a test bacterium (in this case, the LPS mutants) and the titer on a reference bacterium routinely used to maintain a particular phage (in this case, wild-type BL21). It serves as a measure of a phage's capacity to productively infect the alternative test bacterium as a host.

Figure 29:
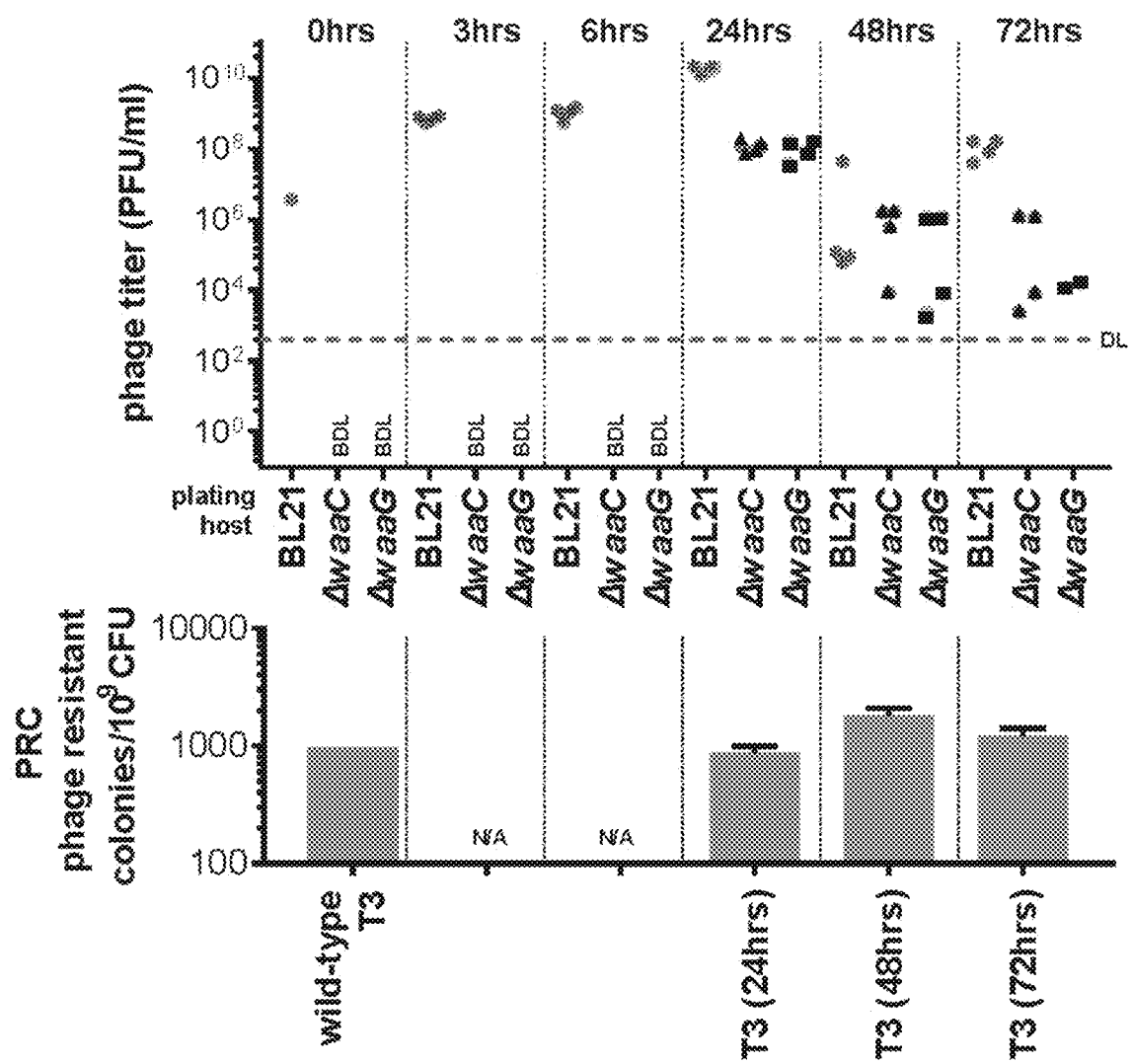
FIG. 29. Related to FIG. 24: Co-evolution of wild-type T3 with wild-type BL21 selects for phage mutants that can infect T3-resistant mutants ΔwaaG and ΔwaaC but that are unable to improve the control of phage-resistant bacterial mutants. Three replicate wild-type BL21 cultures were infected with wild-type T3 and reseeded every 24 hrs into fresh LB medium. At 3, 6, 24, 48 and 72 hours, phage titers of the evolved T3 lysates on the parental host (dots with asterisk) as well as on ΔwaaG (dots with rectangle) and ΔwaaC (dots with triangle) were measured. At times 0, 24, 48 and 72 hours, ~$10^5$ phage forming units (PFUs) of the corresponding evolved T3 lysates were also used to infect a lawn of ~$10^9$ wild-type BL21 colony forming units (CFUs) and obtain the number of T3 phage-resistant colonies (PRC) that arose after 24 hrs (bars bottom plot; results presented as mean+/−standard deviation). DL: detection limit of the assay. BDL: below detection limit. N/A: not available. While T3 mutants that can infect ΔwaaG and ΔwaaC do appear during co-evolution with wild-type BL21, these mutants do not appear capable of preventing resistant colonies from appearing in the plate resistance assay.

Though very rare, T3 mutants capable of infecting either ΔwaaG, ΔwaaC, or both arise if wild-type BL21 is co-cultured with wild-type T3 over extended periods of time. This is because wild-type T3 eliminates most wild-type bacteria and selects for resistant mutants, among which are LPS mutants. This in turn selects for phage mutants that can infect them (Perry et al. PLoS One 10, e0130639 (2015)). Phage mutants that infect either ΔwaaG or ΔwaaC arise in wild-type T3/wild-type BL21 co-cultures were verified but were only observed after at least 24 hrs of co-incubation (FIG. 29). Whether these naturally occurring mutants of T3 might be sufficient at decreasing resistance in BL21 cultures compared to wild-type T3 was also investigated. To test this, a simple co-plating selection assay was carried out where $10^9$ colony forming units (CFU) of wild-type BL21 were challenged with wild-type T3 or the evolved T3 lineages described above, and the number of mutant colonies surviving after 24 hrs were counted (hereafter referred to as phage-resistant colonies, or PRC). Surprisingly, the evolved T3 lysates (lysates of T3 co-cultured with BL21 for 24, 48 or 72 hrs) did not perform any better than wild-type T3 (FIG. 29; bottom plot) despite significant numbers of T3 mutants capable of plaquing on ΔwaaG or ΔwaaC (FIG. 29; top plot). This suggests that the mutant T3 phages obtained from this natural evolution experiment either fail to infect many of the different T3-resistant BL21 mutants that arose during the co-culture, adsorb to all but very slowly, suffer from a decreased fitness as a result of the mutation(s) they acquired, or a combination of all the above. Importantly, this also corroborates previous work (Perry et al. PLoS One 10, e0130639 (2015)) that indicates that T3 is limited in its potential to overcome resistance through natural evolution. Based on these results, all stock lysates of isolated phages or phagebody libraries were generated by limiting infection to 3 hours to prevent natural phage evolution.

Each phagebody library was serially diluted and arrayed on both ΔwaaG and ΔwaaC to quantify the number of PFU and gauge the success of each library (FIGS. 24B-24C). To ascertain the reproducibility of bank construction, library synthesis was repeated up to 21 times. A summary of all libraries constructed is available in TABLE 6.

Every library mutagenizing the HI loop yielded phagebodies active against both ΔwaaG and ΔwaaC. Even when elongated to 5 (HI[+1]) or 7 amino acids (HI[+3]), HI loop libraries were productive (FIG. 24B, HI[+1] data set on ΔwaaG and ΔwaaC; TABLE 6, [HI+1] and HI[+3] lines, last three columns). This is despite the fact that some of these libraries were far from saturating (TABLE 6, HI[+3] line) and loop elongation may have unpredictable consequences on tail fiber structure. Contrarily, DE and FG phagebodies rarely demonstrated infectivity against ΔwaaG or ΔwaaC LPS mutants (FIG. 24B, DE and FG datasets on ΔwaaG and ΔwaaC; TABLE 6, DE and FG lines last three columns), while about half of the libraries aimed at all or parts of the BC loop produced hits on ΔwaaG or ΔwaaC (FIG. 24B, BC[1-4], BC[3-7] and BC[6-9] datasets on ΔwaaG and ΔwaaC; TABLE 6, BC, BC[1-4], BC[3-7] and BC[6-9] lines last three columns). Therefore, not all loops are equal when it comes to receptor recognition. The HI and BC loops appear particularly critical for host binding and are able to tolerate mutagenesis, while the DE and FG loops seem to have a negligible role in receptor recognition or are particularly constrained in sequence by the tail-fiber structure, or a combination of the two.

Example 15: Phagebody with Broadened Host Range and Long-Term Suppression of Resistance From the direct plating of phagebody libraries described above in Example 14, 14 different phagebodies were isolated on ΔwaaG or ΔwaaC. However, some libraries failed to produce functional phagebodies (TABLE 6), so it was unclear if a serial panning amplification would uncover rare or poorly growing phagebodies. To implement this, three different host strains were used, ΔwaaG, ΔwaaC, and a natural T3-resistant BL21 mutant that was experimentally isolated and referred to as D10. The panning experiment consisted of infecting a fresh culture of the desired T3-resistant bacterial mutant with a particular phagebody library at a high multiplicity of infection (MOI=0.4), then recovering the progeny phages and repeating the cycle 3 times.

All of the libraries passed through the panning regimen yielded phagebodies capable of infecting at least one of the above mentioned T3-resistant bacteria, with the exception of the BC[3-7] and DE libraries (FIG. 30B). The FG library also performed poorly, requiring panning at a MOI of 40 instead of 0.4 to identify successful phagebodies that could plaque on ΔwaaG (FIG. 30B). Interestingly, FG libraries were also the most difficult to build, as they consistently yielded lower transformation (TABLE 6). The remaining phagebody libraries easily produced large titers of phagebodies that could infect T3-resistant strains with limited to no enrichment needed (FIG. 30B).

In total, 26 distinct phagebodies were isolated and characterized, 14 from direct isolation on LPS mutants and 12 from the panning experiments (TABLE 7). The gp17 tip of all isolated phagebodies was sequenced which identified mutations within the expected loop region, although these were sometimes accompanied by spontaneous point mutations elsewhere in the tip sequence. Some libraries were also designed to harbor silent mutations to help track acquisition of plasmid material by the phage via sequencing. Some of these mutant gp17 tip sequences were recloned into a wild-type gene 17 plasmid and recombined into T3 to confirm that they were responsible for the expanded host range (TABLE 7). The resulting lysates were spotted onto BL21 LPS mutants and 4 to 8 plaques were purified, isolated, and Sanger sequenced. 100% of the isolated phagebodies able to infect LPS mutants carried the gene 17 mutation introduced via our plasmids. Moreover, control phagebody libraries grown on a strain containing the unmutated gene 17 plasmid did not plaque on LPS mutants, thus strengthening the conclusion that no other mutations present in the phage were responsible for the observed phenotypes (FIG. 24B, WT gene 17 dataset on ΔwaaG and ΔwaaC). Isolated and sequenced phagebodies were named using the following nomenclature: "name of the seed phage (loop mutated:new protein sequence for that particular loop)".

Figure 24D:
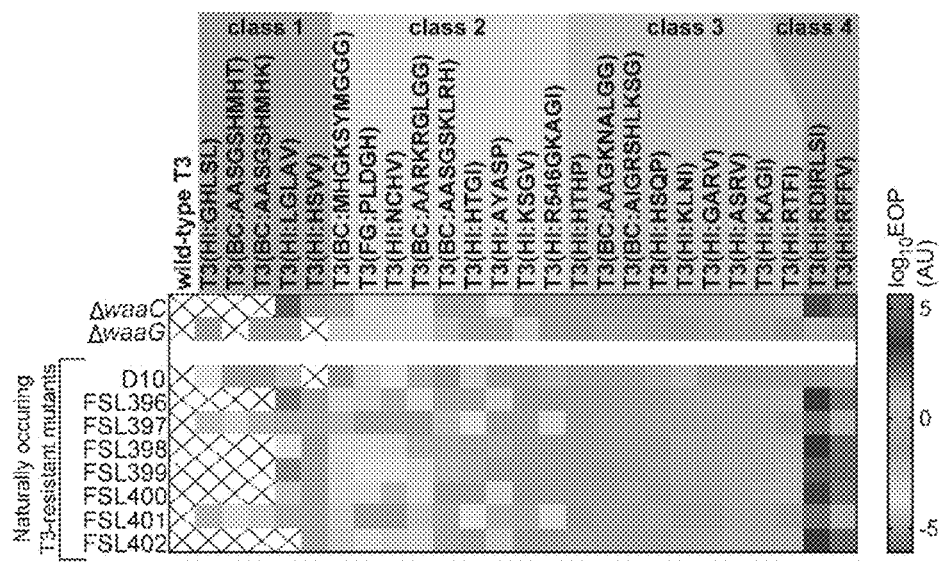

To characterize the relevance of these phagebodies to the development of T3 resistance by E. coli BL21, seven additional T3-resistant bacterial mutants (FSL397-402) were randomly isolated and the EOP of each isolated phagebody was measured on these BL21 mutants along with ΔwaaG, ΔwaaC, and D10 mutants. Based on the EOP and the number of bacterial mutants that the phagebodies were able to infect, the individual phagebodies were assigned to a particular class (1 to 4). As can be seen in FIG. 24D, some of the phagebodies failed to infect some or even the majority of the T3 resistant mutants and often did so at a very low EOP. These phagebodies were grouped into class 1. Class 2 contained phagebodies that infected all test strains but at relatively poor EOP ($\log_{10}$ EOP≤−2). Class 3 phagebodies infected all bacterial variants at similar efficiency to wild-type BL21 (−2≤EOP≤2) and therefore had vastly broadened host ranges that included a large variety of naturally occurring T3 resistant mutants. Two phages, T3(HI:RFFV) and T3(HI:RDIRLSI), constituted class 4 phagebodies. Both had almost completely lost the capacity to infect wild-type BL21 (hence their very high EOP) but grew robustly on T3-resistant strains. While class 1, 2 and 3 phagebodies expanded on the starting host range of T3, class 4 phagebodies changed their preferred host, which is remarkable considering an extremely small percentage of phagebodies that were synthesized were sampled. Interestingly, there was no obvious correlation between the class that a phagebody belonged to and the loop that contained the mutations.

Example 15: Loop Diversification in Phagebodies can Delay or Prevent Bacterial Resistance When a wild-type BL21 culture is infected with T3, it follows a relatively predictable growth pattern. Within one to two hours, the culture clears and remains visibly clear for 6-12 hours. However, if incubated further, T3-resistant bacterial mutants will grow and eventually colonize the medium. A $10^9$ CFU BL21 population is expected to contain ~$10^3$ T3-resistant mutants (FIG. 29).

Figure 25A:
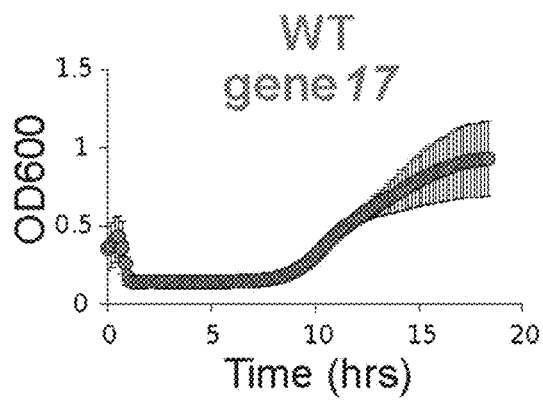
FIGS. 25A-25H. Phagebody libraries can prevent the onset of resistance.
Figure 25B:
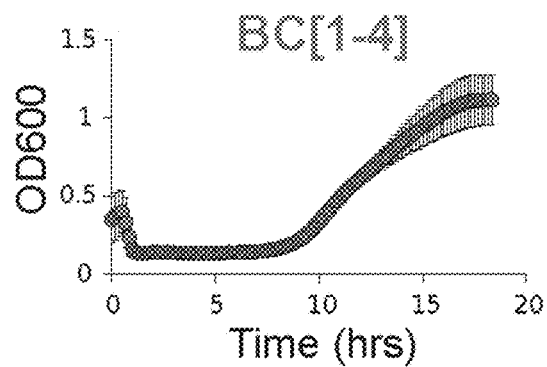
Figure 25C:
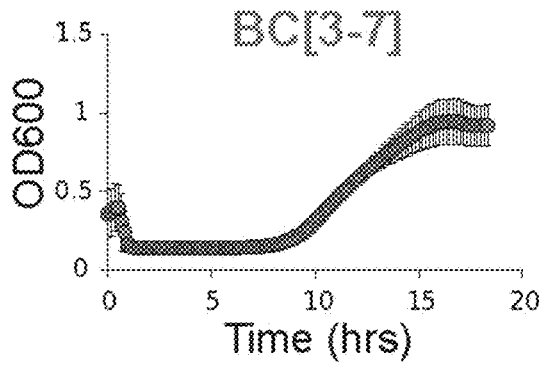
Figure 25D:
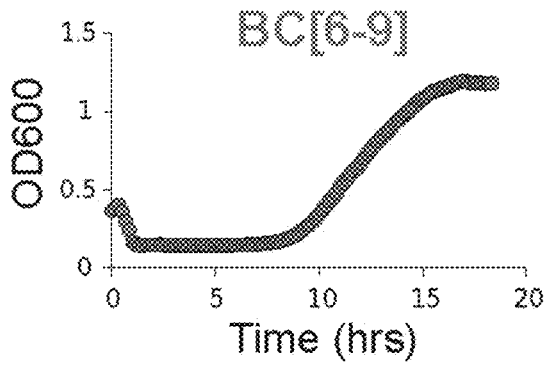
Figure 25E:
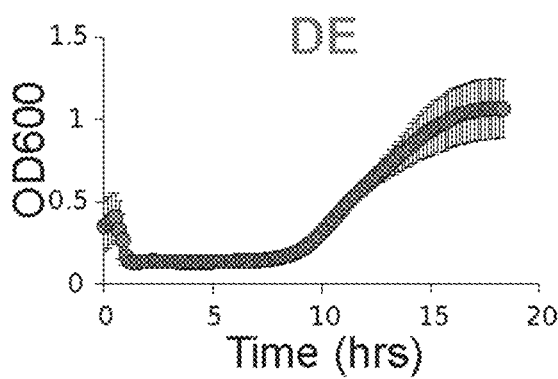
Figure 25F:
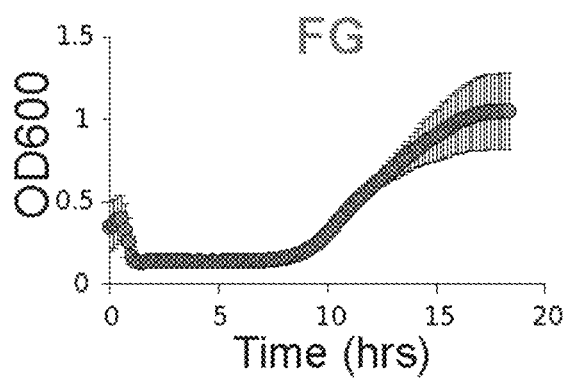
Figure 25G:
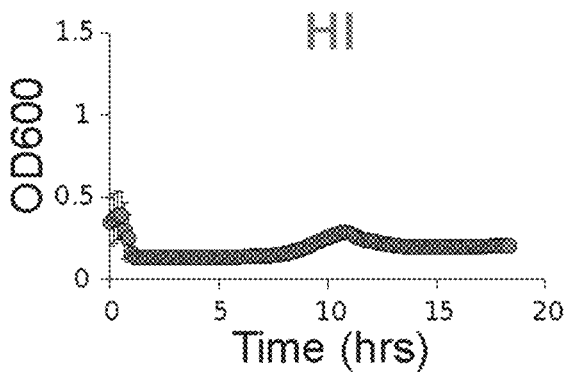
Figure 25H:
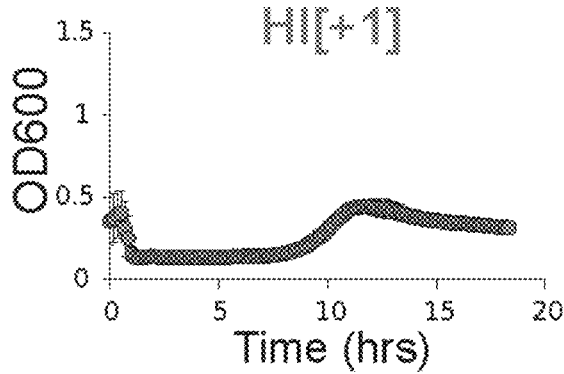

It was previously shown that phagebodies can plaque on and infect bacterial LPS mutants known to evolve from prolonged T3 infection (Perry et al. PLoS One 10, e0130639 (2015)). Thus, it was expected that these phage libraries would be able to curb resistance compared to wild-type T3. As an initial screen, bacterial growth kinetics were measured upon phage infection at a starting MOI of ~0.01. Only the HI loop libraries prevented bacterial resistance at 24 hours post infection (FIGS. 25G-25H compared to FIG. 25A). Surprisingly, the BC loop libraries did not curb resistance (FIGS. 25B-25D) despite the demonstrated presence of host-range-altered phagebodies (FIG. 24B; TABLE 6).

Phagebody libraries contain a large diversity of different phagebodies (~$10^5$-$10^7$ unique phage mutants) such that each individual phagebody is at a low concentration (~100-1000 PFU/ml). Additionally, some phagebodies may have low EOP against bacterial mutants and may not be very useful. To alleviate this potential problem, experiments were performed to formulate a defined cocktail composed of a limited number of phagebodies, each at high concentrations. As an initial cocktail formulation, 12 isolated phagebodies were mixed together in equal amounts (TABLE 7). Replicate cultures of wild-type BL21 were infected with wild-type T3 or the cocktail at an MOI of $10^{-3}$ (total phage concentration). Every 24 hrs, each culture was diluted two-fold into fresh 2× concentrated LB medium. The low dilution rate was used to avoid dilution of cocktail members that may not be necessary early in the evolutionary path of the bacterial population but may become important later on.

Figure 26:
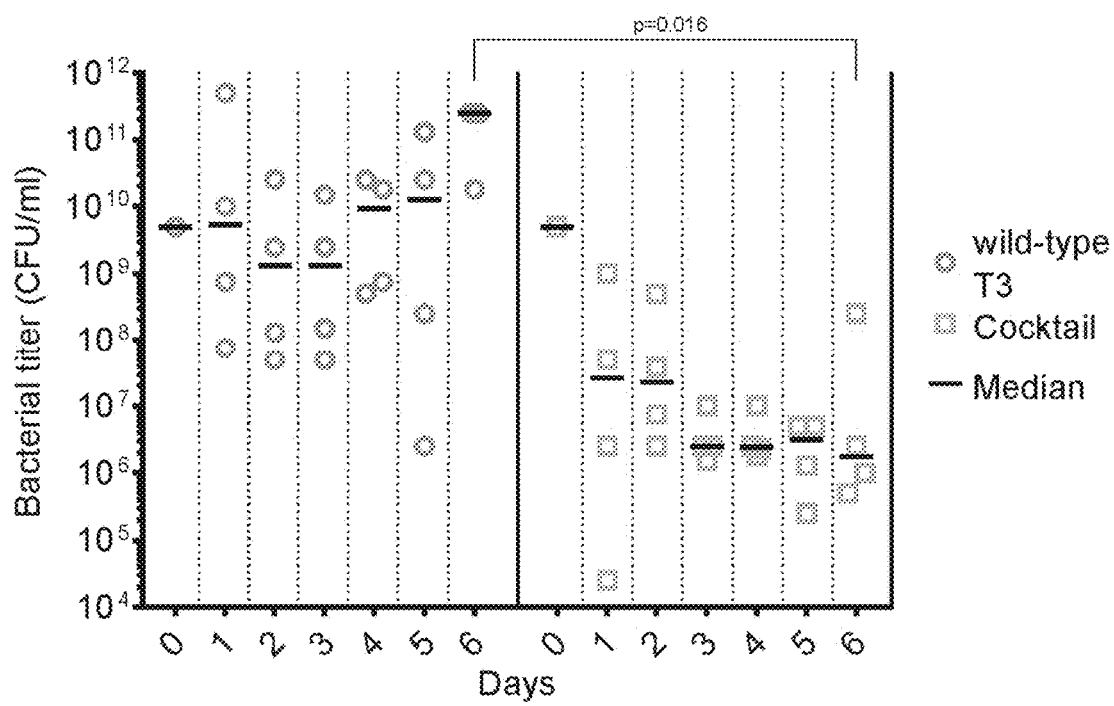
FIG. 26. Cocktail of 12 individual phagebodies inhibits the development of phage resistance in populations of E. coli BL21. Replicates of four 50 ml cultures were inoculated with wild-type T3 (circles) or a cocktail of 12 phagebodies (squares) obtained from the enrichment experiment presented in FIG. 30. Each culture was serially passaged every day with a 2-fold dilution into 2×-concentrated LB media for 6 consecutive days and the bacterial titer was measured at each time (see methods and materials below for details). The day 0 titer corresponds to that of the starter culture before phage addition. All data points are represented with the median as a black horizontal bar. Only the day 6 data showed statistically significant differences between the bacterial titers for cultures treated with the cocktail versus wild-type T3 (t-testp=0.016). The black bar represents the median value for each day. The limit of detection is ~300 CFU/ml, which is below the lowest data point on the graph.

At day 1 and 2, there was no statistically relevant difference between the T3-treated and cocktail-treated cultures, although there was a trend for T3-treated cultures to have higher bacterial titers compared to cocktail-treated cultures (FIG. 26, circles versus squares). Beyond day 2, the bacterial titer of the cocktail-infected populations (FIG. 26, squares) tended to decrease, while in the wild-type-T3 infected control, they increased. At day 6, the phagebody cocktail decreased bacterial titers by approximately 5 orders of magnitude more than wild-type T3 (FIG. 26, circles versus squares). Most importantly, the phagebody cocktail was able to prevent regrowth of the bacterial culture for approximately a week, whereas wild-type T3 incurred visible resistance from the very first day and therefore only afforded transient control of the bacterial population. Assuming a 60-minute doubling time, which is slow for *E. coli* but reasonable considering that phage predation keeps populations low and fresh medium is brought in regularly, this equates to suppression of phage resistance for ~150 bacterial generations by the phagebody cocktail.

Example 16: Individual Phagebodies can Prevent Resistance and Eradicate Bacterial Populations Since a small cocktail was able to suppress bacterial resistance very well, experiments were performed to determine whether this property could be recapitulated by individual phagebodies. To provide a quantitative measurement for the anti-resistance potential for each phagebody, a simple co-plating assay similar to that described earlier was conducted to determine the number of PRC per ~$10^9$ CFU of BL21 after 24 hrs of plating. The resistance index was defined as the $\log_{10}$ of the ratio between the phagebody-resistant PRC to the number of wild-type-T3-resistant PRC. A resistance index above 1 means the tested phage is worse than wild-type T3, while a score below 1 indicates the phage is better than wild-type T3.

The two worst phagebodies, T3(HI:RDIRLSI) and T3(HI:RFFV) (FIG. 27A), were not surprising based on their host range measurements. Indeed, neither phagebody infected wild-type BL21 efficiently (FIG. 24D), which led to poor clearing of BL21 cultures and high numbers of PRC when plated.

Figure 27A:
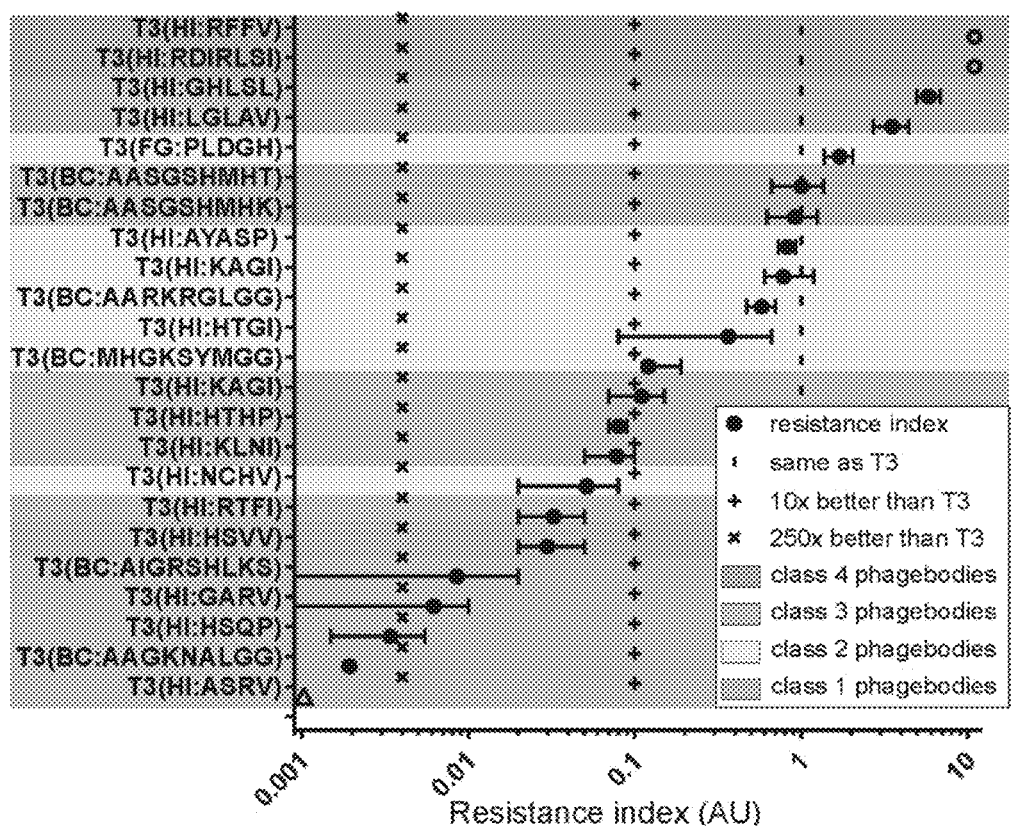
FIGS. 27A-27B. Isolated phagebodies inhibit the development of phage resistance in populations of E. coli BL21.

There was a strong correlation between a phagebody's performance in the resistance index test and the class to which it belonged (see boxes around a phagebody's name in FIG. 27A). Class 1 and 2 phagebodies (FIG. 27A) generally performed about the same or worse than wild-type T3 (resistance index between 0.5 and 5) with the notable exception of T3(HI:HSVV), which was among the top performing phagebodies (FIG. 27A). Class 1 and 2 phagebodies are phages that either failed to infect all T3-resistant mutants of our panel or did so at a low efficiency. T3(HI:HSVV) is a class 1 phagebody because it failed to produce plaques on ΔwaaG and D10 but it displayed excellent infectivity towards all other strains tested (FIG. 24D).

On the other end of the spectrum, T3(HI:ASRV) showed the highest potency at preventing resistance, as it did not allow a single colony to grow on any of the three replicate plates. This corresponds to ~750-times less bacterial resistance than observed when treating bacteria with wild-type T3. Class 3 phagebodies exhibited excellent suppression of bacterial resistance, which is expected given that this class efficiently infected all T3-resistant bacterial mutants tested and wild-type BL21 (FIG. 24D). It is particularly remarkable that class 3 phagebodies were obtained from all three isolation hosts (ΔwaaC, ΔwaaG and D10 (TABLE 7)). It is also noteworthy that no phagebody library or our 12-phagebody cocktail managed to contain bacterial resistance as completely as T3(HI:GARV) did. Importantly, these results show that a single phagebody can perform as well or even better than a cocktail.

Seven of the best performing phagebodies were selected and assessed for their efficiencies at preventing bacterial resistance in a larger population and over a longer period. Four replicate wild-type BL21 cultures were inoculated at an MOI of $10^4$ with each phagebody (~$10^6$ phages and ~$10^{10}$ bacteria). Every 24 hours, bacterial CFU and phage PFU were determined by plaquing on BL21, ΔwaaG, and ΔwaaC and the cultures were diluted 100-fold into fresh medium to allow for ample time for bacterial and phage growth and co-evolution.

Figure 27B:
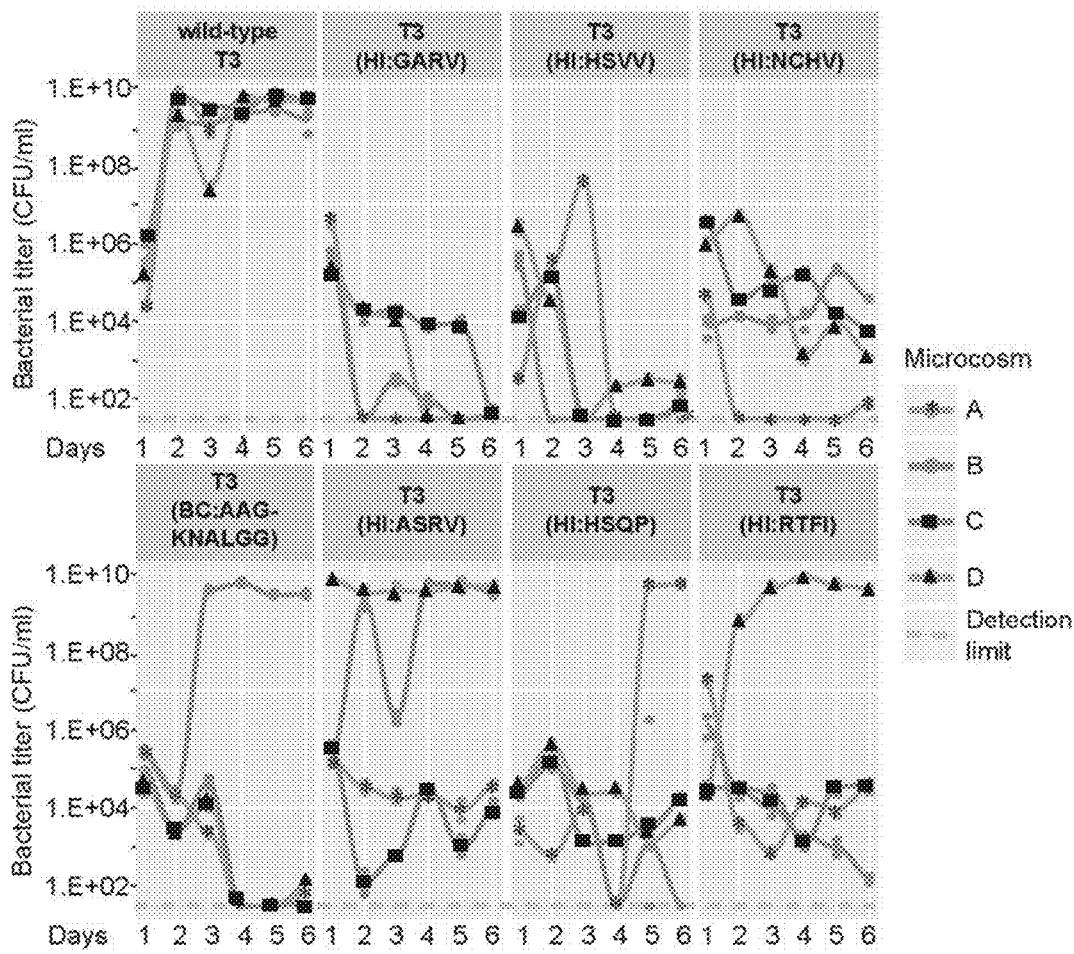
Figure 31:
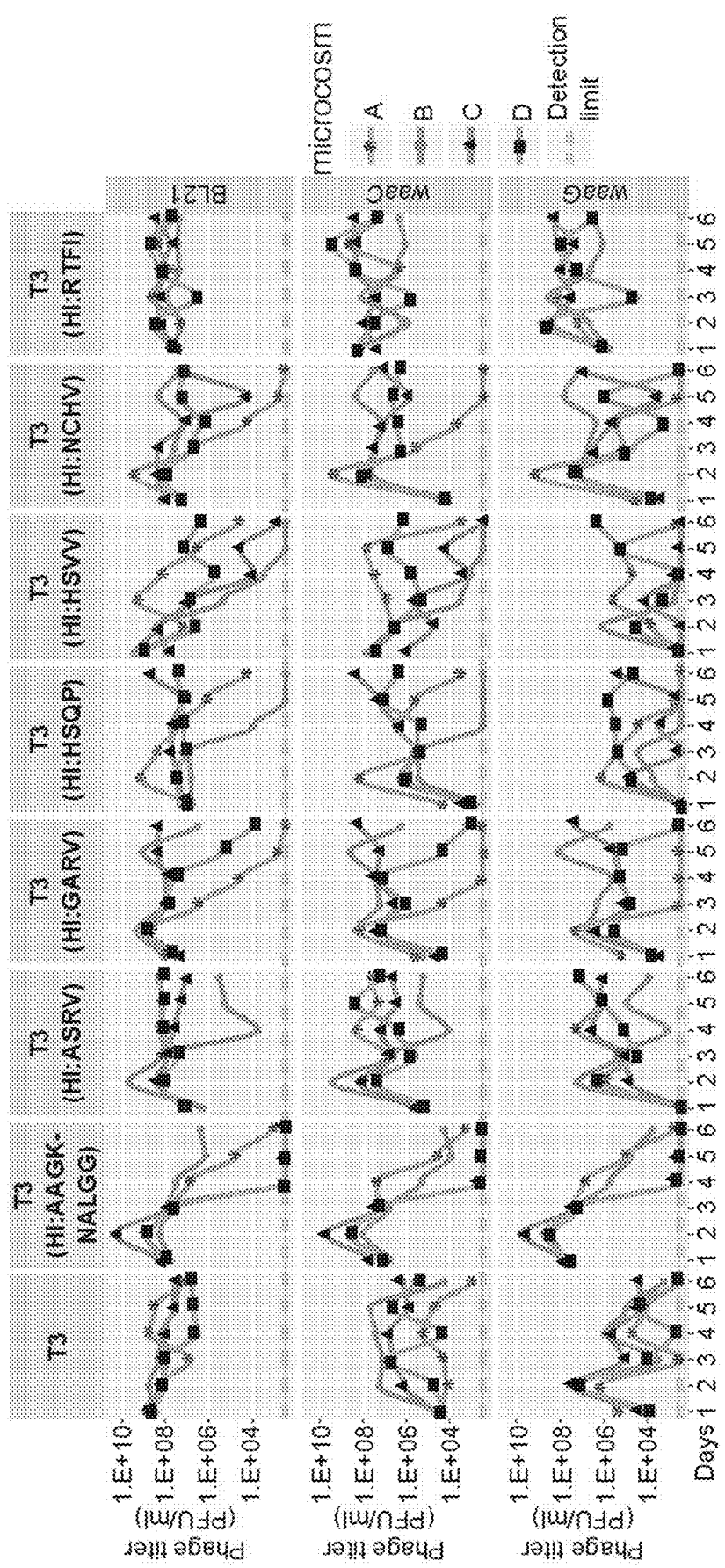
FIG. 31. Related to FIG. 27B: Phage titer of parallel cultures infected with wild-type T3 or select phagebodies in long-term resistance suppression assays. Four parallel phage/wild-type BL21 10 ml co-cultures for each phage (listed at the top) were set up and incubated for 6 days with daily reseeding at 100-fold dilution into fresh media. Before each reseed, phage titers on wild-type BL21, ΔwaaC, and ΔwaaG were measured.

In all four wild-type T3 control samples, bacterial levels remained low throughout day 1 but then rose to saturating levels ($10^9$-$10^{10}$ CFU/ml) composed of T3-resistant bacterial mutants, and remained high until the end of the experiment (FIG. 27B, top left panel). As wild-type T3 reproduced on the starting bacterial pool, the titer rose from a starting concentration of ~$10^5$ PFU/ml to ~$10^9$ PFU/ml within the first day. Although the phage titer showed a slight tendency to decrease over the rest of the experiment, it remained at or above $10^7$ PFU/ml thereafter (FIG. 31, first line, first column), suggesting that the phage reproduced on available bacteria. Despite the appearance of a substantial titer of phage variants capable of plaquing on ΔwaaC and ΔwaaG (up to $10^8$ PFU/ml in one culture; FIG. 31, first column, second and third lines), wild-type T3 failed to control resistance development and bacterial growth in a strikingly repeatable fashion. This observation corroborates data presented in FIG. 25A and literature (Perry et al. PLoS One 10, e0130639 (2015); Qimron et al. Proc. Natl. Acad. Sci. U.S.A. 103, 19039-44(2006)).

All of the selected phagebodies performed better than wild-type T3 in this long-term resistance prevention assay. Four of the seven phagebodies kept the bacterial titer below $10^6$ CFU/ml in most, but not all, replicate cultures (FIG. 27B, bottom line). The other three phagebodies (T3:HI:GARV, T3(HI:HSVV) and T3(HI:NCHV)) maintained bacterial titers several orders of magnitude lower than the starting titer (~$10^9$ CFU/ml) for all 4 microcosms over the entire length of the experiment (FIG. 27B, first line, last three columns).

T3(HI:GARV) was particularly remarkable because it was capable of reducing bacterial CFU below the detection limit for the last time point in all four cultures tested (~300 CFU in the entire 10 ml microcosm; FIG. 27B dotted line). In at least two of the four cultures, not only did the CFU drop below detectability, but the T3(HI:GARV) PFU also decreased about 100-fold every day. This decrease corresponds to the dilution factor applied upon reseeding cultures (FIG. 31, fourth column). This suggests that T3(HI:GARV) did not reproduce after the first day in those two microcosms and was passively diluted away with subsequent passages. This observation was unlikely to be due to any remaining bacteria being resistant to T3(HI:ASRV) since no bacterial growth was observed; this suggests that the bacteria may have been completely wiped out. A similar situation was observed in some but not all of the cultures infected with T3(HI:HSVV), T3(HI:NCHV), and T3(BC:AAGKN-ALGG) (FIG. 27B and FIG. 31).

On the other hand, PFU of all four T3(HI:RTFI) infected cultures hovered around $10^8$ PFU/ml throughout the experiment (FIG. 31), despite the bacterial titer dropping to ~$10^4$ CFU/ml in three of the four cultures (FIG. 27B). Thus, it seemed that the T3(HI:RTFI) phagebody entered a steady-state equilibrium with its host bacterium instead of driving it to extinction. Together, these experiments demonstrate that engineered phagebodies perform better than wild-type T3 at controlling the long-term evolution of bacterial resistance in response to phage predation but that phagebodies differ in their individual behavior. This feature may enable phage-based therapies with the ability to achieve long-term control over target bacterial populations without resorting to cocktails.

Plasmids pSLM22

SEQ ID NO: 150

```
   1 TCAGAAGAAC TCGTCAAGAA GGCGATAGAA GGCGATGCGC GAGCGGCGAT TGCGAATCGG
  61 ACCGTAAAGC ACGAGGAAGC GGTCAGCCCA TTCGCCGCCA ACCTCTTCAG CAATATCACG
 121 GGTAGCCAAC GCTATGTCCT GATAGCGGTC CGCCACACCC AGCCGGCCAC AGTCGATGAA
 181 TCCAGAAAAG CGGCCATTTT CCACCATGAT ATTCGGCAAG CAGGCATCGC CATGGGTCAC
 241 GACGAGATCC TCGCCGTCGG GCATGCGCGC CTTGAGCCTG GCGAACAGTT CGGCTGGCGC
 301 GAGCCCCTGA TGCTCTTCGT CCAGATCATC CTGATCGACA AGACCGGCTT CCATCCGAGT
 361 ACGTGCTCGC TCGATGCGAT GTTTCGCTTG GTGGTCGAAT GGGCAGGTAG CCGGATCAAG
 421 CGTATGCAGC CGCCGCATTG CATCAGCCAT GATGGATACT TTCTCGGCAG GAGCAAGGTG
 481 AGATGACAGG AGATCCTGCC CCGGCACTTC GCCCAATAGC AGCCAGTCCC TTCCCGCTTC
 541 AGTGACAACG TCGAGCACAG CTGCGCAAGG AACGCCCGTC GTGGCCAGCC ACGATAGCCG
 601 CGCTGCCTCG TCCTGCAGTT CATTCAGGGC ACCGGACAGG TCGGTCTTGA CAAAAAGAAC
 661 CGGGCGCCCC TGCGCTGACA GCCGGAACAC GGCGGCATCA GAGCAGCCGA TTGTCTGTTG
 721 TGCCCAGTCA TAGCCGAATA GCCTCTCCAC CCAAGCGGCC GGAGAACCTG CGTGCAATCC
 781 ATCTTGTTCA ATCATGCGAA ACGATCCTCA TCCTGTCTCT TGATCAGATC TTGATCCCCT
 841 GCGCCATCAG ATCCTTGGCG GCAAGAAAGC CATCCAGTTT ACTTTGCAGG GCTTCCGAAC
 901 CTTACCAGAG GGCGCCCCAG CTGGCTATTC CGACGTCTAA GAAACCATTA TTATCATGAC
 961 ATTAACCTAT AAAAATAGGC GTATCACGAG GCCCTTTCGT CTTCACCTCG AGTCCCTATC
1021 AGTGATAGAG ATTGACATCC CTATCAGTGA TAGAGATACT GAGCACATCA GCAGGACGCA
1081 CTGACCTTAA TTAAATGCGC ACCCTTAGCG AGAGGTTTAT CATTAAGGTC AACCTCTGGA
1141 TGTTGTTTCG GCATCCTGCA TTGAATCTGA GTTACTGTCT GTTTTCCTGA ATTCTAGCCA
1201 CTGATGGTAA TATTCAAGGT ACTAAGTGGG GAGGTAAGTG GCTTGATGCT TACCTACGTG
1261 ACAGCTTCGT TGCGAAGTCC AAGGCGTGGA CTCAGGTGTG GTCTGGTAGT GCTGGCGGTG
1321 GGGTAAGTGT GACTGTTTCA CAGGATCTCC GCTTCCGCAA TATCTGGATT AAGTGTGCCA
1381 ACAACTCTTG GAACTTCTTC CGTACTGGCC CCGATGGAAT CTACTTCATA GCCTCTGATG
1441 GTGGATGGTT ACGATTCCAA ATACACTCCA ACGGTCTCGG ATTAAAGAAT ATTGCAGACA
1501 GTCGTTCAGT ACCTAATGCA ATCATGGTGG AGAACGAGTA ATAAGCATCA AAGGAACTAC
1561 TTTAAGTCCA CGGATGGACT ATCACACTGA ATTCAGGAAA CCCGTTTTTT CTGACGTAAG
1621 GGTGCGCAAC TTTCATGAAA TCCGCTGAAT ATTTGAACAC TTTTAGATTG AGAAATCTCG
1681 GCCTACCTGT CATGAACAAT TTGCATGACA TGTCTAAGGC GACTCGCATA TCTGTTGAAA
1741 CACTTCGGTT GTTAATCTAT ACAGCTGATT TTCGCTATAG GATCTACACT GTAGAAAAGA
1801 AAGGCCCAGA GAAGAGAATG AGAACCATTT ACCAACCTTC TCGAGAACTT AAAGCCTTAC
1861 AAGGATGGGT TCTACGTAAC ATTTTAGATA AACTGTCGTC ATCTCCTTTT TCTATTGGAT
1921 TTGAAAAGCA CCAATCTATT TTGAATAATG CTACCCCGCA TATTGGGCA AACTTTATAC
1981 TGAATATTGA TTTGGAGGAT TTTTTCCCAA GTTTAACTGC TAACAAAGTT TTTGGAGTGT
2041 TCCATTCTCT TGGTTATAAT CGACTAATAT CTTCAGTTTT GACAAAAATA TGTTGTTATA
2101 AAAATCTGCT ACCACAAGGT GCTCCATCAT CACCTAAATT AGCTAATCTA ATATGTTCTA
2161 AACTTGATTA TCGTATTCAG GGTTATGCAG GTAGTCGGGG CTTGATATAT ACGAGATATG
2221 CCGATGATCT CACCTTATCT GCACAGTCTA TGAAAAGGT TGTTAAAGCA CGTGATTTTT
2281 TATTTTCTAT AATCCCAAGT GAAGGATTGG TTATTAACTC AAAAAAAACT TGTATTAGTG
```

-continued

```
2341    GGCCTCGTAG TCAGAGGAAA GTTACAGGTT TAGTTATTTC ACAAGAGAAA GTTGGGATAG
2401    GTAGAGAAAA ATATAAAGAA ATTAGAGCAA AGATACATCA TATATTTTGC GGTAAGTCTT
2461    CTGAGATAGA AAACGTTAGG GGATGGTTGT CATTTATTTT AAGTGTGGAT TCAAAAAGCC
2521    ATAGGAGATT AATAACTTAT ATTAGCAAAT TAGAAAAAAA ATATGGAPAG AACCCTTTAA
2581    ATAAAGCGAA GACCTAAGGA TCCGGTTGAT ATTATTCAGA GGTATAAAAC GAATGAGTAC
2641    TGCACTCGCA ACGCTGGCTG GGAAGCTGGC TGAACGTGTC GGCATGGATT CTGTCGACCC
2701    ACAGGAACTG ATCACCACTC TTCGCCAGAC GGCATTTAAA GGTGATGCCA GCGATGCGCA
2761    GTTCATCGCA TTACTGATCG TTGCCAACCA GTACGGCCTT AATCCGTGGA CGAAAGAAAT
2821    TTACGCCTTT CCTGATAAGC AGAATGGCAT CGTTCCGGTG GTGGGCGTTG ATGGCTGGTC
2881    CCGCATCATC AATGAAAACC AGCAGTTTGA TGGCATGGAC TTTGAGCAGG ACAATGAATC
2941    CTGTACATGC CGGATTTACC GCAAGGACCG TAATCATCCG ATCTGCGTTA CCGAATGGAT
3001    GGATGAATGC CGCCGCGAAC CATTCAAAAC TCGCGAAGGC AGAGAAATCA CGGGGCCGTG
3061    GCAGTCGCAT CCCAAACGGA TGTTACGTCA TAAAGCCATG ATTCAGTGTG CCCGTCTGGC
3121    CTTCGGATTT GCTGGTATCT ATGACAAGGA TGAAGCCGAG CGCATTGTCG AAAATACTGC
3181    ATACACTGCA GAACGTCAGC CGGAACGCGA CATCACTCCG GTTAACGATG AAACCATGCA
3241    GGAGATTAAC ACTCTGCTGA TCGCCCTGGA TAAAACATGG GATGACGACT TATTGCCGCT
3301    CTGTTCCCAG ATATTTCGCC GCGACATTCG TGCATCGTCA GAACTGACAC AGGCCGAAGG
3361    AGTAAAAGCT CTTGGATTCC TGAAACAGAA AGCCGCAGAG CAGAAGGTGG CAGCATGAAC
3421    GCGTGCTAGA GGCATCAAAT AAAACGAAAG GCTCAGTCGA AAGACTGGGC CTTTCGTTTT
3481    ATCTGTTGTT TGTCGGTGAA CGCTCTCCTG AGTAGGACAA ATCCGCCGCC CTAGACCTAG
3541    GGGATATATT CCGCTTCCTC GCTCACTGAC TCCTAACGCT CGGTCGTTCG ACTGCGGCGA
3601    GCGGAAATGG CTTACGTACG GGGCGGAGAT TTCCTGGAAG ATGCCAGGAA GATACTTAAC
3661    AGGGAAGTGA GAGGGCCGCG GCAAAGCCGT TTTTCCATAG GCTCCGCCCC CCTGACAAGC
3721    ATCACGAAAT CTGACGCTCA AATCAGTGGT GGCGAAACCC GACAGGACTA TAAAGATACC
3781    AGGCGTTTGC CCCTGGCGGC TCCCTCGTGC GCTCTCCTGT TCCTGCCTTT CGGTTTACCG
3841    GTGTCATTTC GCTGTTATGG CCGCGTTTGT CTTATTCTAC GCCTGACACT CAGTTCCGGG
3901    TAGGAAGTTC GCTCCAAGCT GGACTGTATG CACGAACCCC CCGTTCAGTC CGACCGCTGC
3961    GCCTTATCCG GTAACTATCG TCTTGAGTCC AACCCGGAAA GACATGCAAA AGCACCACTG
4021    GCAGCAGCCA CTGGTAATTG ATTTAGAGGA GTTAGTCTTG AAGTCATGCG CCGGTTAAGG
4081    CTAAACTGAA AGGACAAGTT TTGGTGACTG CGCTCCTCCA AGCCAGTTAC CTCGGTTCAA
4141    AGAGTTGGTA GCTCAGAGAA CCTTCGAAAA ACCGCCCTGC AAGGCGGTTT TTTCGTTTTC
4201    AGAGCAAGAG ATTACGCGCA GACCAAAACG ATCTCAAGAA GATCATCTTA TTAATCAGAT
4261    AAAATATTTC TAGATTTCAG TGCAATTTAT CTCTTCAAAT GTAGCACCTG AAGTCAGCCC
4321    CATACGATAT AAGTTGTTAC TAGTGCTTGG ATTCTCACCA ATAAAAAACG CCCGGCGGCA
4381    ACCGAGCGTT CTGAACAAAT CCAGATGGAG TTCTGAGGTC ATTACTGGAT CTATCAACAG
4441    GAGTCCAAGC GAGCTCTCGA ACCCCAGAGT CCCGC
``` pSLM49

SEQ ID NO: 151

```
  1    ATGATTGAAC AAGATGGATT GCACGCAGGT TCTCCGGCCG CTTGGGTGGA GAGGCTATTC
 61    GGCTATGACT GGGCACAACA GACAATCGGC TGCTCTGATG CCGCCGTGTT CCGGCTGTCA
121    GCGCAGGGGC GCCCGGTTCT TTTTGTCAAG ACCGACCTGT CCGGTGCCCT GAATGAACTG
```

-continued

```
 181   CAGGACGAGG CAGCGCGGTT ATTGTGGCTG GCTACGATGG GCGTTCCTTG CGCAGCTGTG
 241   CTCGACGTTG TCACTGAAGC GGGAAGGGAC TGGCTGCTAT TGGGGGAAGT GCCGGGGCAG
 301   GATCTCCTGT CATCTCACCT TGCTCCTGCC GAGAAAGTAT CCATCATGGC TGATGCAATG
 361   CGGCGGCTGC ATACGCTTGA TCCGGCTACC TGCCCATTCG ACCACCAAGC GAAACATCGC
 421   ATCGAGCGAG CACGTACTCG GATGGAAGCC GGTCTTGTCG ATCAGGATGA TCTGGACGAA
 481   GAGCATCAGG GGCTCGCGCC AGCCGAACTG TTCGCCAGGC TCAAGGCGCG CATGCCCGAC
 541   GGCGAGGATC TCGTCGTGAC CCATGGCGAT GCCTGCTTGC CGAATATCAT GGTGGAAAAT
 601   GGCCGCTTTT CTGGATTCAT CGACTGTGGC CGGCTGGGTG TGGCGGACCG CTATCAGGAC
 661   ATAGCGTTGG CTACCCGTGA TATTGCTGAA GAGCTTGGCG GCGAATGGGC TGACCGCTTC
 721   CTCGTGCTTT ACGGTATCGC CGCTCCCGAT TCGCAGCGCA TCGCCTTCTA TGGCCTTCTT
 781   GACGAGTTCT TCTGAGCGGG ACTCTGGGGT TCGAGAGCTC GCTTGGACTC CTGTTGATAG
 841   ATCCAGTAAT GACCTCAGAA CTCCATCTGG ATTTGTTCAG AACGCTCGGT GCCGCCGGG
 901   CGTTTTTAT TGGTGAGAAT CCAAGCACTA GTAACAACTT ATATCGTATG GGGCTGACTT
 961   CAGGTGCTAC ATTTGAAGAG ATAAATTGCA CTGAAATCTA GAAATATTTT ATCTGATTAA
1021   TAAGATGATC TTCTTGAGAT CGTTTTGGTC TGCGCGTAAT CTCTTGCTCT GAAAACGAAA
1081   AAACCGCCTT GCAGGGCGGT TTTTCGAAGG TTCTCTGAGC TACCAACTCT TTGAACCGAG
1141   GTAACTGGCT TGGAGGAGCG CAGTCACCAA AACTTGTCCT TTCAGTTTAG CCTTAACCGG
1201   CGCATGACTT CAAGACTAAC TCCTCTAAAT CAATTACCAG TGGCTGCTGC CAGTGGTGCT
1261   TTTGCATGTC TTTCCGGGTT GGACTCAAGA CGATAGTTAC CGGATAAGGC GCAGCGGTCG
1321   GACTGAACGG GGGGTTCGTG CATACAGTCC AGCTTGGAGC GAACTGCCTA CCCGGAACTG
1381   AGTGTCAGGC GTGGAATGAG ACAAACGCGG CCATAACAGC GGAATGACAC CGGTAAACCG
1441   AAAGGCAGGA ACAGGAGAGC GCACGAGGGA GCCGCCAGGG GGAAACGCGT GGTATCTTTA
1501   TAGTCCTGTC GGGTTTCGCC ACCACTGATT TGAGCGTGAG ATTTCGTGAT GCTTGTCAGG
1561   GGGGCGGAGC CTATGGAAPA ACGGCTTTGC CGCGGCCCTC TCACTTCCCT GTTAAGTATC
1621   TTCCTGGCAT CTTCCAGGAA ATCTCCGCCC CGTTCGTAAG CCATTTCCGC TCGCCGCAGT
1681   CGAACGACCG AGCGTAGCGA GTGAGTGAGC GAGGAAGGGG AATATATCCC CTAGGTCTGG
1741   ATCCTGAAGG AACGTGACCC AAACAAACCG TACACCTCTA GAGAGGTAAT GGGAGCTATG
1801   GGTTCGAACC TTCTGGAGCA GATGCCTTCC GCTGGCTTTG TGGCTAACGT AGGGGCTACC
1861   TTAATGAATG CTGCTGGTGT GGTTAACTCA CCTAACAAAG CAACCCAGCA GGACTTCATG
1921   ACTGGATTGA TGAACTCTAC CAAAGAGTTA GTGCCTAACG ACCCTCTTAC TCAACAGCTT
1981   GTGGTTAAGA TTTATGAGGC GAACGGTGTT AACCTGAGGG AGCGTAAGAA ATAATACGAC
2041   TCACTATAGG GAGAGGCGAA ATAATCTTCT CCCTGTAGTC TCTTAGATTT ACTTTAAGGA
2101   GGTCAAATGG CTAACGTAAT TAAAACCGTT TTGACTTACC AGTTAGATGG CTCCAATCGT
2161   GATTTTAATA TCCCGTTTGA GTATCTAGCC CGTAAGTTCG TAGTAGTAAC CCTTATTGGC
2221   GTAGACCGCA AGGTCCTTAC GATTAATGCA GACTACCGTT TTGCTACGCG TACTACCATC
2281   TCACTTACCA AGGCTTGGGG TCCAGCGGAT GGATACACTA CCATCGAGTT ACGCCGAGTA
2341   ACCTCCACAA CCGACCGATT GGTTGACTTT ACGGATGGTT CAATCCTCCG TGCGTATGAC
2401   CTTAACGTCG CTCAGATTCA AACGATGCAC GTAGCGGAAG AGGCCCGTGA CCTCACTGCT
2461   GATACCATAG GTGTCAATAA TGATGGTCAT TTGGATGCTC GTGGTCGTCG AATTGTTAAC
2521   CTAGCGAACG CTGTGGATGA CCGCGACGCT GTTCCGTTTG GTCAACTTAA GACCATGAAC
2581   CAGAACTCGT GGCAGGCGCG TAATGAGGCA CTACAGTTCC GTAATGAGGC TGAGACTTTC
```

-continued

```
2641  AGAAATCAAA CGGAGGTTTT TAAGAATGAG TCCGGTACTA ACGCTACGAA CACAAAGCAG
2701  TGGCGAGATG AGGCTAATGG GTCCCGAGAT GAAGCCGAGC AGTTCAAGAA TACGGCTGGT
2761  CAATACGCTA CATCTGCTGG GAACTCTGCT ACTGCTGCGC ATCAATCTGA GGTAAACGCT
2821  GAGAACTCCG CTACAGCAGC AGCGAACTCT GCGAATTTGG CAGAACAACA CGCAGACCGT
2881  GCGGAACGTG AAGCAGACAA GCTGGGGAAT TTTAATGGAC TGGCTGGTGC AATTGACAGG
2941  GTGGATGGAA CCAATGTGTA CTGGAAAGGA GGTATCCATG CGAACGGACG CCTTTACCTT
3001  ACCTCAGATG GTTTCGACTG TGGTCAGTAT CAACAGTTCT TTGGTGGTTC TGCTGGTCGT
3061  TACTCTGTCA TGGAGTGGGG TGATGAGAAC GGATGGCTGA TGCATGTTCA ACGTAGAGAG
3121  TGGACAACAG CGATAGGTGA TAACATCCAG CTAGTAGTAA ACGGACATAT CATCGCCCAA
3181  GGTGGAGACA TGACTGGTCC GCTGAAATTG CAGAATGGAC ATGCCCTTTA CTTAGAGTCC
3241  GCATCCGACA AGGCGCAATA TATTCTATCT AAAGATGGTA ACAGAAACAA CTGGTACATT
3301  GGTAGAGGAT CAGATAACAA CAATGACTGT ACCTTCCACT CCTATGTGTA TGGTACGAAC
3361  TTAACACTCA AGCCGGACTA TGCAGTAGTT AACAAACGCT TCCACGTAGG TCAGGCAGTT
3421  GTAGCCACTG ATGGTAATAT TCAAGGTACT AAGTGGGGAG GTAAGTGGCT TGATGCTTAC
3481  CTAAACGATA CTTACGTTAA GAAGACAATG GCCTGGACTC AAGTATGGGC TGCTGCTAGT
3541  GGTAGTTACA TGGGAGGAGG TTCTCAGACT GATACTCTCC CACAGGACTT GCGATTCCGC
3601  AACATATGGA TTAAGACCAG AAACAACTAT TGGAACTTCT TCCGAACTGG TCCTGACGGT
3661  ATCTACTTCC TTTCAGCCGA GGGCGGTTGG CTAAAATTCC AGATACACTC TAATGGCAGG
3721  GTATTTAAGA ACATAGCGGA TAGAGATGCG CCTCCAACAG CAATAGCCGT AGAGGACGTG
3781  TAATAAGCAT CAAAGGAACT ACTTTAAGTC CACGGATGGA CTATCACACT AAGGAGGACA
3841  CATGTTGTCA TTGGATTTTA ACAACGAACT AATTAAAGCG GCACCGATTG TAGGTACAGG
3901  TGTTGCAGAT GTTAGTGCAA GACTGTTCTT CGGGCTAAGC CTGAATGAAT GGTTCTATGT
3961  GGCTGCTATC GCCTACACAG TGGTTCAGAT TGGTGCCAAG GTAGTCGATA AGATCCCGGG
4021  tgcaAACCTT GACGTCGGAA TTGCCAGCTG GGGCGCCCTC TGGTAAGGTT GGGAAGCCCT
4081  GCAAAGTAAA CTGGATGGCT TTCTTGCCGC CAAGGATCTG ATGGCGCAGG GGATCAAGAT
4141  CTGATCAAGA GACAGGATGA GGATCGTTTC GC
```

REFERENCES

1. Alexander M., Why Microbial Predators and Parasites do not Eliminate their Prey and Hosts. Annu. Rev. Microbiol., 1981. 35: p. 113-33.
2. Ando H., Lemire S., Pires D. P., Lu T. K., Engineering Modular Viral Scaffolds for Targeted Bacterial Population Editing. Cell Syst., 2015. 1(3): p. 187-196.
3. Arnold K., Bordoli L., Kopp J., Schwede T., The SWISS-MODEL workspace: a web-based environment for protein structure homology modelling. Bioinformatics., 2006. 22(2): p. 195-201.
4. Beck A., Wurch T., Bailly C., and Corvaia N., Strategies and challenges for the next generation of therapeutic antibodies. Nat. Rev. Immunol., 2010. 10(5): p. 345-52.
5. Bierman M., Logan R., O'Brien K., Seno E. T., Rao R. N., and Schoner B. E., Plasmid cloning vectors for the conjugal transfer of DNA from *Escherichia coli* to *Streptomyces* spp., Gene. 1992. 116(1): p. 43-9.
6. Bikard D., Euler C. W., Jiang W., Nussenzweig P. M., Goldberg G. W., Duportet X., Fischetti V. A., Marraffini L. A., Exploiting CRISPR-Cas nucleases to produce sequence-specific antimicrobials. Nat. Biotechnol., 2014. 32(11): p. 1146-50.
7. Le Bourgeois P., Lautier M., Mata M., and Ritzenthaler P., New tools for the physical and genetic mapping of *Lactococcus* strains. Gene, 1992. 111(1): 109-14.
8. Bull J. J., and Molineux I. J., Predicting evolution from genomics: experimental evolution of bacteriophage T7. Heredity (Edinb)., 2008. 100(5): p. 453-63.
9. Bull J. J., Badgett M. R., Molineux I. J., A General Mechanism for Viral Resistance to Suicide Gene Expression, J. Mol. Evol., 2001. 53(1): p. 47-54.
10. Bull J. J., Vegge C. S., Schmerer M., Chaudhry W. N., and Levin B. R., Phenotypic resistance and the dynamics of bacterial escape from phage control. PLoS One., 2014. 9(4): e94690.
11. Calendar R., The Bacteriophages, Oxford Univ. Press 2005. 2nd edition.
12. Chen M., Zhang L., Xin S., Yao H. Lu C., and Zhang W., Inducible Prophage Mutant of *Escherichia coli* Can Lyse New Host and the Key Sites of Receptor Recognition Identification, Front. Microbiol., 2017. 8: p. 147.

13. Chen Z., Guo L., Zhang Y., Walzem R. L., Pendergast J. S., Printz R. L., Morris L. C., Matafonova E., Stien X., Kang L., Coulon D., McGuinness O.P., Niswender K. D., and Davies S. S., Incorporation of therapeutically modified bacteria into gut microbiota inhibits obesity, J. Clin. Invest., 2014. 124(8): p. 3391-406.
14. Citorik R. J., Mimee M., Lu T. K., Sequence-specific antimicrobials using efficiently delivered RNA-guided nucleases. Nat. Biotechnol., 2014. 32(11): p. 1141-45.
15. Cooper C. J., Khan Mirzaei M., Nilsson A. S., Adapting Drug Approval Pathways for Bacteriophage-Based Therapeutics. Front. Microbiol., 2016. 3(7): p. 1209.
16. Datsenko K. Z. and Wanner B. L., One-step inactivation of chromosomal genes in Escherichia coli K-12 using PCR products, Proc. Natl. Acad. Sci. U.S.A., 2000. 97(12): p. 6640-45.
17. Datta S., Costantino N., and Court D. L. A set of recombineering plasmids for gram-negative bacteria, Gene. 2006. 379: p. 109-15.
18. Devlin AS., Marcobal A., Dodd D., Nayfach S., Plummer N., Meyer T., Pollard K. S., Sonnenburg J. L., and Fischbach M. A., Modulation of a Circulating Uremic Solute via Rational Genetic Manipulation of the Gut Microbiota. Cell Host Microbe., 2016. 20(6): p. 709-15.
19. Ducancel F. and Muller B. H. Molecular engineering of antibodies for therapeutic and diagnostic purposes, MAbs., 2012. 4: p. 445-57.
20. Farzadfard F. and Lu T. K., Genomically encoded analog memory with precise in vivo DNA writing in living cell populations, Science, 2014. 346(6211): p. 1256272.
21. Fieller E., The biological standardization of Insulin, Suppl. to J. R. Stat. Soc., 1940. p. 1-64.
22. Foltz I. N., Karow M., and Wasserman S. M., Evolution and Emergence of Therapeutic Monoclonal Antibodies: What Cardiologists Need to Know, Circulation, 2013. 127(22): p. 2222-30.
23. Galtier M., De Sordi L., Maura D., Arachchi H., Volant S., Dillies M. A., Debarbieux L., Bacteriophages to reduce gut carriage of antibiotic resistant uropathogens with low impact on microbiota composition. Environ. Microbiol., 2016. 18(7): p. 2237-45.
24. Garcia-Doval C., Van Raaij M. J., Structure of the receptor-binding carboxy-terminal domain of bacteriophage T7 tail fibers. Proc. Natl. Acad. Sci. U.S.A., 109 (24): p. 2390-95.
25. Gebhart D., Williams S. R., and Scholl D., Bacteriophage SP6 encodes a second tailspike protein that recognizes Salmonella enterica serogroups C2 and C3, Virology, 2017. 507: p. 263-66.
26. Gladstone E., Molineux I., and Bull J., Evolutionary principles and synthetic biology: avoiding a molecular tragedy of the commons with an engineered phage, J. Biol. Eng., 2012. 6(1): p. 13.
27. Guo H., Arambula D., Ghosh P., Miller J. F., Diversity-generating Retroelements in Phage and Bacterial Genomes. Microbiol. Spectr., 2014. 2(6): doi:10.1128/microbiolspec.MDNA3-0029-2014.
28. Gupte G., Woodward C., and Stout V., Isolation and characterization of rcsB mutations that affect colanic acid capsule synthesis in Escherichia coli K-12, J. Bacteriol., 1997. 179(13): p. 4328-35.
29. Hawkins S. A., Layton A. C., Ripp S., Williams D., and Sayler G. S., Genome sequence of the Bacteroides fragilis phage ATCC 51477-B1, Virol. J., 2008. 5: p. 97.
30. Heilpern A. J., and Waldor M. K., pIII CTX, a Predicted CTX φ Minor Coat Protein, Can Expand the Host Range of Coliphage fd To Include Vibrio cholerae pIII CTX, a Predicted CTX Minor Coat Protein, Can Expand the Host Range of Coliphage fd To Include Vibrio cholerae, J. Bacteriol., 2003. 185(3): p. 1037-44.
31. Heinrichs D. E., Yethon J. A., and Whitfield C., Molecular basis for structural diversity in the core regions of the lipopolysaccharides of Escherichia coli and Salmonella enterica, Mol. Microbiol., 1998. 30(2): p. 221-32.
32. Hsu C. R., Lin T. L., Pan Y. J., Hsieh P. F., and Wang J. T., Isolation of a Bacteriophage Specific for a New Capsular Type of Klebsiella pneumoniae and Characterization of Its Polysaccharide Depolymerase, PLoS One, 2013. 8(8): e70092.
33. Igawa T., Tsunoda H., Kuramochi T., Sampei Z., Ishii S., and Hattori K., Engineering the variable region of therapeutic IgG antibodies, MAbs, 2011. 3(3): p. 243-52.
34. Kim M. S., Kim Y. D., Hong S. S., Park K., Ko K. S., and Myung H., Phage Encoded Colanic Acid-Degrading Enzyme Permits Lytic Phage Infection of a Capsule-Forming Resistant Mutant Escherichia coli Strain, Appl. Environ. Microbiol., 2014. 81(3): p. 900-09.
35. Klein G., Lindner B., Brabetz W., Brade H., Raina S., Escherichia coli K-12 Suppressor-free Mutants Lacking Early Glycosyltransferases and Late Acyltransferases: minimal lipopolysaccharide structure and induction of envelope stress response. J. Biol. Chem., 2009. 284(23): p. 15369-89.
36. Kutateladze M., Adamia R., Bacteriophages as potential new therapeutics to replace or supplement antibiotics. Trends Biotechnol., 2010. 28(12): p. 591-95.
37. Kutter E., De Vos D., Gvasalia G., Alavidze Z., Gogokhia L., Kuhl S., Abedon S. T., Phage therapy in clinical practice: treatment of human infections. Curr. Pharm. Biotechnol., 2010. 11(1): p. 69-86.
38. Kutter E. M., Kuhl S. J., Abedon S. T., Re-establishing a place for phage therapy in western medicine. Future Microbiol., 2015. 10(5): p. 685-8.
39. Labrie S. J., Samson J. E., Moineau S., Bacteriophage resistance mechanisms. Nat. Rev. Microbiol., 2010. 8(5): p. 317-27.
40. Leiman P. G., Battisti A. J., Bowman V. D., Stummeyer K., Malenhoff M., Gerardy-Schahn R., Scholl D., and Molineux I. J., The structures of bacteriophages K1E and K1-5 explain processive degradation of polysaccharide capsules and evolution of new host specificities, J. Mol. Biol., 2007. 371(3): p. 836-49.
41. Levin B. R. and Bull J. J., Population and evolutionary dynamics of phage therapy, Nat. Rev. Microbiol., 2004. 2(2): p. 166-73.
42. Lin T. L., Hsieh P. F., Huang Y. T., Lee W. C., Tsai Y. T., Su P. A., Pan Y. J., Hsu C. R., Wu M. C., and Wang J. T., Isolation of a bacteriophage and its depolymerase specific for K1 capsule of Klebsiella pneumoniae: implication in typing and treatment, J. Infect. Dis., 2014. 210(11): p. 1734-44.
43. Lin T. Y., Lo Y. H., Tseng P. W., Chang S. F., Lin Y. T., and Chen T. S., A T3 and T7 recombinant phage acquires efficient adsorption and a broader host range, PLoS One, 2012. 7(2): e30954.
44. Lu T. K., Collins J. J., Dispersing biofilms with engineered enzymatic bacteriophage. Proc. Natl. Acad. Sci. U.S.A., 2007. 104(27): p. 11197-202.
45. Lu T. K., Collins J. J., Engineered bacteriophage targeting gene networks as adjuvants for antibiotic therapy. Proc. Natl. Acad. Sci. U.S.A., 2009. 106(12): p. 4629-34.
46. May T. B. and Chakrabarty A. M. (1994). *Pseudomonas aeruginosa*: genes and enzymes of alginate synthesis. Trends Microbiol. 2, 151-157.

47. Maynard N. D., Birch E. W., Sanghvi J. C., Chen L., Gutschow M. V., Covert M. W., A forward-genetic screen and dynamic analysis of lambda phage host-dependencies reveals an extensive interaction network and a new antiviral strategy. PLoS Genet., 2010. 6(7): e1001017.
48. McMahon S. A., Miller J. L., Lawton J. A., Kerkow D. E., Hodes A., Marti-Renom M. A., Doulatov S., Narayanan E., Sali A., Miller J. F., Ghosh P., The C-type lectin fold as an evolutionary solution for massive sequence variation. Nat. Struct. Mol. Biol., 2005. 12(10): p. 886-92.
49. Meyer J. R., Dobias D. T., Weitz J. S., Barrick J. E., Quick R. T., and Lenski R. E., Repeatability and Contingency in the Evolution of a Key Innovation in Phage Lambda, Science, 2012. 335(6067): p. 428-32.
50. Międzybrodzki R., Borysowski J., Weber-Dąbrowska B., Fortuna W., Letkiewicz S., Szufnarowski K., Pawelczyk Z., Rogóż P., Klak M., Wojtasik E., Górski A., Clinical aspects of phage therapy. Adv. Virus Res., 2012. 83: p. 73-121.
51. Montag D., Riede I., Eschbach M. L., Degen M., and Henning U., Receptor-recognizing proteins of T-even type bacteriophages. Constant and hypervariable regions and an unusual case of evolution, J. Mol. Biol., 1987. 196(1): p. 165-74.
52. Nguyen A. H., Molineux I. J., Springman R., and Bull J. J., Multiple genetic pathways to similar fitness limits during viral adaptation to a new host, Evolution, 2012. 66(2): p. 363-74.
53. Pawluk, A., Staals, R. H. J., Taylor, C., Watson, B. N. J., Saha, S., Fineran, P. C., Maxwell, K. L., Davidson, A. R., Inactivation of CRISPR-Cas systems by anti-CRISPR proteins in diverse bacterial species, Nat. Microbiol., 2016. 1(8): 16085.
54. Perry E. B., Barrick J. E., Bohannan B. J., The Molecular and Genetic Basis of Repeatable Coevolution between *Escherichia coli* and Bacteriophage T3 in a Laboratory Microcosm., PLoS One. 2009. 10(6): e0130639.
55. Pickard D., Thomson N. R., Baker S., Wain J., Pardo M., Goulding D., Hamlin N., Choudhary J., Threfall J., and Dougan G., Molecular characterization of the *Salmonella enterica* serovar *Typhi* Vi-typing bacteriophage E1, J. Bacteriol., 2008. 190(7): p. 2580-87.
56. Pouillot F., Blois H., and Iris F., Genetically Engineered Virulent Phage Banks in the Detection and Control of Emergent Pathogenic Bacteria, Biosecur. Bioterror., 2010. 8(2): p. 155-69.
57. Qimron U., Marintcheva B., Tabor S., Richardson C. C., Genomewide screens for *Escherichia coli* genes affecting growth of T7 bacteriophage. Proc. Natl. Acad. Sci. U.S.A., 2006. 103(50): p. 19039-44.
58. Ross A., Ward S., and Hyman P., More Is Better: Selecting for Broad Host Range Bacteriophages, Front. Microbiol., 2016. 7: p. 1352.
59. Scholl D., Adhya S., and Merril C., *Escherichia coli* K1's Capsule Is a Barrier to *Escherichia coli* K1's Capsule Is a Barrier to Bacteriophage T7, Appl. Eviron. Microbiol., 2005. 71(8): p. 4872-74.
60. Scholl D., Cooley M., Williams S. R., Gebhart D., Martin D., Bates A., and Mandrell R., An engineered R-type pyocin is a highly specific and sensitive bactericidal agent for the food-borne pathogen *Escherichia coli* O157:H7, Antimicrob. Agents Chemother., 2009. 53(7): p. 3074-80.
61. Shen T. C., Albenberg L., Bittinger K., Chehoud C., Chen Y. Y., Judge C. A., Chau L., Ni J., Sheng M., Lin A., Wilkins B. J., Buza F. L., Lewis J. D., Daikhin Y., Nissim I., Yudokoff M., Bushman F. D., and Wu G. D., Engineering the gut microbiota to treat hyperammonemia, J. Clin. Invest., 2015. 125(7): p. 2841-50.
62. Silva J. B., Storms Z., and Sauvageau D., Host receptors for bacteriophage adsorption, FEMS Microbiol. Lett., 2016, 363(4): pii: fnw002.
63. Springman R., Keller T., Molineux I. J., and Bull J. J., Evolution at a high imposed mutation rate: adaptation obscures the load in phage T7, Genetics, 2010. 184(1): p. 221-32.
64. Springman R., Kapadia-Desai D. S., Molineux I. J., Bull J. J., Evolutionary recovery of a recombinant viral genome. G3 (Bethesda)., 2012. 2(7): p. 825-30.
65. Strom A. R. and Kaasen I., Trehalose metabolism in *Escherichia coli*: stress protection and stress regulation of gene expression, Mol. Microbiol., 1993. 8(2): p. 205-10.
66. Studier F. W., Daegelen P., Lenski R. E., Maslov S., and Kim J. F., Understanding the differences between genome sequences of *Escherichia coli* B strains REL606 and BL21(DE3) and comparison of the *E. coli* B and K-12 genomes, J. Mol. Biol., 2009. 394(4): p. 653-80.
67. Tétart F., Repoila F., Monod C., and Krisch H. M., Bacteriophage T4 host range is expanded by duplications of a small domain of the tail fiber adhesin, J. Mol. Biol., 1996. 258(5): p. 726-31.
68. Trojet S. N., Caumont-Sarcos A., Perrody E., Comeau A. M., and Krisch H. M., The gp38 adhesins of the T4 superfamily: a complex modular determinant of the phage's host specificity, Genome Biol. Evol., 2011. 3: p. 674-86.
69. Willis L. M. and Whitfield C., Structure, biosynthesis, and function of bacterial capsular polysaccharides synthesized by ABC transporter-dependent pathways, Carbohydr. Res., 2013. 378: p. 35-44.
70. Yoichi M., Abe M., Miyanaga K., Unno H., and Tanji Y., Alteration of tail fiber protein gp38 enables T2 phage to infect *Escherichia coli* O157:H7, J. Biotechnol., 2005. 115(1) p. 101-7.
71. Yosef I., Goren M. G., Globus R., Molshanski-Mor S., and Qimron U., Extending the Host Range of Bacteriophage Particles for DNA Transduction, Mol. Cell, 2017. 66(5): p. 721-28.
72. Yu P., Mathieu J., Li M., Dai Z., and Alvarez P. J. J., Isolation of Polyvalent Bacteriophages by Sequential Multiple-Host Approaches, Appl. Environ. Microbiol., 2015. 82(3): p. 808-15.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A synthetic bacteriophage comprising mutations in a tail fiber tip protein, wherein the mutations: (i) are engineered in one or more binding loops of the tail fiber tip protein, wherein the binding loops face the basal or apex side of the tail fiber; and (ii) cause the bacteriophage to have a different host range than the corresponding bacteriophage lacking the mutations in the tail fiber tip protein.

2. The synthetic bacteriophage of claim 1, wherein the mutations are in one or more of loops BC, DE, FG and/or HI.

3. The synthetic bacteriophage of claim 1, wherein the bacteriophage is a T3 bacteriophage, a T7 bacteriophage, or a bacteriophage having a tail fiber tip protein that has 90% or greater amino acid identity to a T3 bacteriophage gp17 tail fiber tip protein or a T7 bacteriophage gp17 tail fiber tip protein.

4. The synthetic bacteriophage of claim 1, wherein the tail fiber tip protein is gp17.

5. A pharmaceutical composition comprising the synthetic bacteriophage as claimed in claim 1, and a pharmaceutically-acceptable carrier.

6. A pharmaceutical composition comprising two or more types of synthetic bacteriophages as claimed in claim 1, wherein each of the two or more types of bacteriophages has different mutations in the tail fiber tip protein, and a pharmaceutically acceptable carrier.

7. The composition of claim 6, wherein the two or more types of bacteriophages have different host ranges.

8. A method for treating a bacterial infection comprising administering to a subject having a bacterial infection in need of treatment the pharmaceutical composition as claimed in claim 5.

9. A method of producing one or more synthetic bacteriophages comprising mutating a tail fiber protein of a bacteriophage wherein the mutations: (i) are engineered in one or more binding loops of the tail fiber tip protein, wherein the binding loops face the basal or apex side of the tail fiber; and (ii) cause the bacteriophage to have a different host range than the corresponding bacteriophage lacking the mutations in the tail fiber tip protein.

10. The method of claim 9, wherein the bacteriophage is a T3 bacteriophage, a T7 bacteriophage, or a bacteriophage having a tail fiber tip protein that has 90% or greater amino acid identity to a T3 bacteriophage gp17 tail fiber tip protein or a T7 bacteriophage gp17 tail fiber tip protein.

11. The method of claim 9, wherein the tail fiber tip protein is gp17.

12. The method of claim 9 comprising replacing one or more codons within at least one binding loop of a tail fiber protein with the degenerate codon NNK to introduce amino acid variability in the at least one loop.

13. The method of claim 12, wherein the step of replacing one or more codons comprises amplifying a sequence comprising a bacteriophage gp17 gene region to produce an amplification product.

14. The method of claim 13, further comprising:
circularizing the amplification product;
introducing the circularized amplification product into bacteriophage susceptible bacterial cells;
infecting the bacterial cells with wild-type bacteriophages, wherein said infection facilitates the recombination of the wild-type bacteriophage with the amplification product; and
isolating recombinant synthetic bacteriophages comprising the amplification product.

15. The method of claim 11, wherein the amino acid variability is introduced in any one or more of the BC, DE, FG, and/or HI loops of the gp17 tail fiber protein.

16. The method of claim 9, wherein the mutation in the one or more binding loops comprises one or more amino acid substitutions.

17. The method of claim 9, wherein the mutation in the one or more binding loops shortens or lengthens the one or more binding loops by at least one amino acid.

18. The synthetic bacteriophage of claim 1, wherein the bacteriophage is a bacteriophage having a tail fiber tip protein that has 90% or greater amino acid identity to the C-terminal 104 amino acids of T3 bacteriophage gp17 tail fiber tip protein or the C-terminal 99 amino acids of T7 gp17 tail fiber tip protein.

* * * * *